(12) United States Patent
Dübel et al.

(10) Patent No.: US 10,730,922 B2
(45) Date of Patent: Aug. 4, 2020

(54) COMPOSITION AND METHOD FOR AFFECTING THE BINDING OF ANTIGEN-BINDING POLYPEPTIDES TO ANTIGENS

(71) Applicants: Miltenyi Biotec GmbH, Bergisch Gladbach (DE); Stefan Dübel, Braunschweig (DE)

(72) Inventors: Stefan Dübel, Braunschweig (DE); Sarah-Jane Kellmann, Gummersbach (DE); Holger Thie, Biberach an der Riss (DE)

(73) Assignee: Miltenyi Biotech B.V. & Co. KG, Bergisch Gladbach (DE)

( * ) Notice: Subject to any disclaimer, the term of this patent is extended or adjusted under 35 U.S.C. 154(b) by 139 days.

(21) Appl. No.: 15/650,724

(22) Filed: Jul. 14, 2017

(65) Prior Publication Data
US 2018/0030104 A1 Feb. 1, 2018

(30) Foreign Application Priority Data
Jul. 29, 2016 (EP) ..................................... 16181971

(51) Int. Cl.
*C07K 14/47* (2006.01)
*C07K 16/40* (2006.01)
*C12N 9/12* (2006.01)

(52) U.S. Cl.
CPC .......... *C07K 14/4728* (2013.01); *C07K 16/40* (2013.01); *C12N 9/12* (2013.01); *C12Y 207/11018* (2013.01); *C07K 2317/56* (2013.01); *C07K 2317/622* (2013.01); *C07K 2319/02* (2013.01); *C07K 2319/03* (2013.01)

(58) Field of Classification Search
CPC combination set(s) only.
See application file for complete search history.

(56) References Cited

U.S. PATENT DOCUMENTS

2005/0054000 A1   3/2005   Dubel
2006/0275822 A1*  12/2006  Miyawaki ........ C07K 14/43595
                                                      435/7.1

FOREIGN PATENT DOCUMENTS

WO   WO-02/014371 A1   2/2002
WO   WO-03/078575 A2   9/2003
WO   WO-2005/072392 A2 8/2005

OTHER PUBLICATIONS

Jensen et al., Current Opin. Immunol., 33:9-15. (Year: 2015).*
Baird, G.S. et al. (Sep. 1999). "Circular Permutation and Receptor Insertion Within Green Fluorescent Proteins," *PNAS* 96:11241-11246.
Chattopadhyaya, R. et al. (1992)."Calmodulin Structure Refined at 1.7 Å Resolution," *J Mol Biol* 228:1177-1192.
Galán, A et al. (Jun. 16, 2016). "Library-Based Display Technologies: Where Do We Stand?," *Mol. Biosyst.* 12:2342-2358.
Guntas, G. et al. (Nov. 2004). "A Molecular Switch Created by In Vitro Recombination of Nonhomologous Genes," *Chemistry & Biology* 11:1483-1487.
Hultschig, C. et al. (2004). "Systematic Delineation of a Calmodulin Peptide Interaction," *J. Mol. Biol.* 343:559-568.
Ikura, M. et al. (May 1, 1992). "Solution Structure of a Calmodulin-Target Peptide Complex by Multidimensional NMR," *Science* 256:632-638.
Jeong, W.H. et al. (Mar. 30, 2016). "Fusion Protein of Human Calmodulin and B4 Domain of Protein A From *Staphylococcal aureus*," located at <http://www.rcsb.org/pdb/explore.do?structureID-5coc>, last visited on Sep. 15, 2016, 2 pages.
Keitel, T. et al. (Dec. 12, 1997). "Crystallographic Analysis of Anti-p24 (HIV-1) Monoclonal Antibody Cross-Reactivity and Polyspecificity," *Cell* 91(6):811-820.
Kobatake, E. et al. (Jun. 2012; epublished on Feb. 21, 2012). "Construction of Affinity Changeable Antibody in Response to $Ca^{2+}$," *Biotechnology Letters* 34(6):1019-1023.
Kuboniwa, H. et al. (Sep. 1995). "Solution Structure of Calcium-Free Calmodulin," *Nat Struct Biol.* 2(9):768-776.
Maruani, A et al. (Jul. 14, 2016). "Dual Modification of Biomolecules," *Org. Biomol. Chem.* 14(26):6165-6178.
Megeed, Z. et al. (Apr. 2006). "Modulation of Single-Chain Antibody Affinity with Temperature-Responsive Elastin-Like Polypeptide Linkers," *Biomacromolecules* 7(4):999-1004.
Meister, G. E. et al. (2013). "An Engineered Calmodulin-Based Allosteric Switch for Peptide Biosensing," *ChemBioChem* 14:1460-1467.
Meister, G.E. et al. (2009). "Circular Permutation of Proteins," Chapter 18 in *Protein Engineering Handbook*, Lutz, S. et al. eds., Wiley-VCH Verlag GmbH & Co. KgaA, Winheim, Germany, pp. 453-471.
Miyawaki, A. et al. (Aug. 28, 1997). "Fluorescent Indicators for $Ca^{2+}$ Based on Green Fluorescent Proteins and Calmodulin," *Nature* 388:882-887.

(Continued)

Primary Examiner — Hong Sang
(74) Attorney, Agent, or Firm — Morrison & Foerster LLP

(57) ABSTRACT

The present invention provides a composition comprising i) a polypeptide comprising calmodulin and two immunoglobulin superfamily domains, wherein said two immunoglobulin superfamily domains are linked via said calmodulin; ii) a calmodulin binding molecule; iii) ions binding to the $Ca^{2+}$ binding site of calmodulin; wherein the binding of said calmodulin-binding molecule and of said ions to said $Ca^{2+}$ binding site of calmodulin affects the binding of said polypeptide to an antigen to be bound by said polypeptide. The calmodulin may be a permutated calmodulin. A method for affecting the binding of a polypeptide for an antigen using said composition is also disclosed.

5 Claims, 21 Drawing Sheets
Specification includes a Sequence Listing.

(56) References Cited

OTHER PUBLICATIONS

Montigiani, S. et al. (1996). "Alanine Substitutions in Calmodulin-Binding Peptides Result in Unexpected Affinity Enhancement," *J. Mol. Biol.* 258:6-13.
Nagai, T. et al. (Mar. 13, 2001). "Circularly Permuted Green Fluorescent Proteins Engineered to Sense $Ca^{2+}$," *PNAS* 98(6):3197-3202.
Neri, D. et al. (Apr. 1995). "Calmodulin as a Versatile Tag for Antibody Fragments," *Biotechnology* 13(4):373-377.
Reineke, U. et al. (Sep. 2002). "Identification of Distinct Antibody Epitopes and Mimotopes From a Peptide Array of 5520 Randomly Generated Sequences," *J Immunol Methods* 267(1):37-51.
Ullman, C.G. et al. (May 2011). "In Vitro Methods for Peptide Display and Their Applications," *Brief Funct. Genomics* 10(3):125-134.
Van Vught, R et al. (Feb. 2014). "Site-Specific Functionalization of Proteins and Their Applications to Therapeutic Antibodies," *Comput. Struct. Biotechnol. J.* 9(14):e201402001, pp. 1-13.

\* cited by examiner

COMPOSITION AND METHOD FOR AFFECTING THE BINDING OF ANTIGEN-BINDING POLYPEPTIDES TO ANTIGENS

CROSS REFERENCE TO RELATED APPLICATIONS

This application claims priority to European Application No. EP16181971.9, filed Jul. 29, 2016, incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 212302003300seqlist.txt, date recorded: Jul. 12, 2017, size: 142 KB).

FIELD OF THE INVENTION

The present invention relates to the field of binding modulation of antigen-binding polypeptides, in particular to a calmodulin-linker-based system for said modulation.

BACKGROUND OF THE INVENTION

Antigen-binding polypeptides such as single chain variable fragments (scFv) comprise of the variable domains of the light ($V_L$) and heavy ($V_H$) chain of a corresponding full-length antibody. A similar architecture has also been applied to the structurally similar T cell receptors (scTv) as well as scFab-fragments. In such constructs, both chains are normally connected by a linker which is flexible and does not show any tendency to interfere with folding of the individual immunoglobulin domains. In many cases, these linkers contain assemblies or variations of (Gly$_4$Ser) (SEQ ID NO: 136) repeats, inspired by the unstructured linkers connecting the domains of filamentous bacteriophage minor coat protein III.

ScFv antibody fragments are widely used in a variety of applications, such as for research, diagnostic purposes and even as therapeutics. Immunotoxins, which are used for cancer therapy, are often based on a single chain fragment fused to a bacterial toxin to mediate targeted killing. Another approach is based on bispecific antibodies (BiTEs, bispecific T cell engagers) which activate and redirect cytotoxic T cells against cancer cells. CAR (chimeric antigen receptor)-T cell therapy also relies on scFvs specific for malignant cells. Essential for all of these applications is the extraordinary specificity, selectivity and affinity of antibody paratopes. These properties would also be very useful for the purification of biomaterials, in particular proteins, vaccines or cells. However, the usually very high affinity of antibodies requires harsh elution conditions, which typically impairs folding, integrity or viability of the eluted materials. Therefore, antibodies which retain their excellent specificity while being adjustable in respect of their affinity without requiring harsh conditions for this adjustment would be advantageous for protein purification, cell separation and cell analysis. Even the introduction of an affinity-adjustable antibody for therapy may be envisioned, for example as an additional safety mechanism in CAR-T cell therapy.

Kobatake, E. et al. (2012, *Biotechnol Lett* 34, 1019-23) disclose an affinity changeable antibody in response to calcium. The system is based on a fusion-peptide comprising scFv, wild-type (WT) calmodulin, and a calmodulin-binding peptide. The switch is generated by the addition of calcium to the system. One disadvantage is that the solution must be calcium-free before the intended switch.

Meister, G. E. & Joshi, N. S. (2013, *Chembiochem* 14, 1460-7) disclose a switchable enzyme which bases on the interaction of WT-calmodulin and soluble M13 peptide. In the peptide-bound form the enzyme exhibits an up to 120 times higher catalytic activity compared to the inactive (no peptide bound) state.

WO2002014371A1 discloses Fv constructs having an affinity that can be influenced for a substance to be linked, wherein the Fv constructs have peptides linked to the variable regions and containing binding sites for effector molecules. The effector molecules are ions or antibodies.

Guntas, G. et al. (2004, *Chem Biol* 11, 1483-7) and WO2003078575A2 disclose the creation of a molecular switch of the enzyme TEM1 β-lactamase by circularly permutating the gene encoding the enzyme TEM1 β-lactamase and subsequently inserting it into the gene encoding *E. coli* maltose binding protein which functions as the linker.

WO2005/072392A2 discloses molecular switches, for example with switching activity greater than previously demonstrated, or with altered ligand recognition and binding, and methods of making these molecules involving circular permutation of nucleic acid or amino acid sequences. Molecular switches have been created by recombining non-homologous genes in vitro and subjecting the genes to evolutionary pressure using combinatorial techniques. The approach is envisioned as "rolling" two proteins across each other's surfaces and fusing them at points where their surfaces meet. The approach allows for recombination and testing of maximal numbers of geometric configurations between the two domains. Libraries comprising vast numbers of such fused molecules are provided from which molecular switches with optimal characteristics can be isolated.

Megeed, Z. et al. (2006, *Biomacromolecules* 7, 999-1004) disclose a fusion peptide of scFv with elastin as linker resulting in a temperature dependent affinity of the antigen binding domain to the antigen.

Miyawaki, A. et al. (1997, *Nature* 388, 882-887) disclose a polypeptide comprising a fluorescent protein, wherein its domains are linked by a calmodulin-M13-peptide. Baird et al. (1999, *PNAS* 96: 11241-11246) showed that several rearrangements of GFPs, in which the amino and carboxyl portions are interchanged and rejoined with a short spacer connecting the original termini, still provide fluorescence. These circular permutations have altered pKa values and orientations of the chromophore with respect to a fusion partner. Furthermore, certain locations within GFP tolerate insertion of entire proteins, and conformational changes in the insert can have profound effects on the fluorescence. For example, insertions of calmodulin or a zinc finger domain in place of Tyr-145 of a yellow mutant (enhanced yellow fluorescent protein) of GFP result in indicator proteins whose fluorescence can be enhanced several-fold upon metal binding. The calmodulin graft into enhanced yellow fluorescent protein can monitor cytosolic $Ca^{2+}$ in single mammalian cells.

Nagai et al. (2001, *PNAS* 98:3197-3202) showed by using a circularly permuted green fluorescent protein (cpGFP), in which the amino and carboxyl portions had been interchanged and reconnected by a short spacer between the original termini that they could visualize $Ca^{2+}$-dependent protein-protein interactions in living cells by fluorescence readouts. The cpGFP was fused to calmodulin and its ligand derived peptide, M13. The chimeric protein was fluorescent and its spectral properties changed reversibly with the amount of $Ca^{2+}$.

Calmodulin (CaM) undergoes large conformational changes, depending on the presence of calcium and calmodulin-binding peptides (CBP). In a calcium- and peptide-unbound form, it adopts a closed conformation (Kuboniwa, H. et al., 1995, *Nat Struct Biol* 2, 768-776). The distance between the N- and C-terminus is at its highest in the calcium-bound, open form (Chattopadhyaya, R. et al., 1992, *J Mol Biol* 228, 1177-1192), whereas the termini approach each other when calmodulin binds to a ligand, or a suitable fragment thereof, like peptide M13 (Ikura, M. et al., 1992, *Science* 256, 632-638).

Montigiani et al. (1996, *J. Mol. Biol.* 258:6-13) and Hultschig et al. (2004, *J. Mol. Biol.* 343:559-568) identified high affinity mutants of the CaM binding peptide "M13" which is derived from the rabbit myosin light chain kinase.

There is a need in the art for an alternative or improved composition and/or method for affecting the binding of antigen-binding polypeptides to their respective antigens.

All references cited herein, including patent applications and publications, are incorporated by reference in their entirety.

SUMMARY OF THE INVENTION

Surprisingly, it was shown by the inventors that a polypeptide comprising calmodulin (CaM) and two immunoglobulin superfamily domains, wherein said two immunoglobulin superfamily domains are linked via said calmodulin (a "calmodulin linker"), can be used to affect in both directions the binding of said polypeptide to its antigen by contacting said polypeptide with a calmodulin binding molecule and ions binding to the $Ca^{2+}$ binding site of calmodulin. The concerted binding of said calmodulin-binding molecule and of said ions to said $Ca^{2+}$ binding site of calmodulin leads to conformational changes and influences the binding of said polypeptide for an antigen to be bound by said polypeptide. The system (or composition) comprising the three parts i) the polypeptide with CaM as linker between the two immunoglobulin superfamily domains, ii) the CaM binding molecule such as a CaM-binding peptide (e.g. M13 peptide), and iii) ions binding to the $Ca^{2+}$ binding site of CaM such as $Ca^{2+}$ is superior compared to systems known in the art: It is not a prerequisite for a functional system to eliminate calcium ions from the solution comprising said polypeptide before switching the binding of the polypeptide to its antigen. The switch is only achieved by adding soluble CaM binding molecules such as M13 peptide to the solution in the presence of ions binding to the $Ca^{2+}$ binding site of CaM. This is superior compared to systems known in the art, particular for the use in living organisms, for example when used to modulate the affinity of a CAR on a T cell or other suitable effector cell, as in this situation, the $Ca^{2+}$ concentration may not be sufficiently adjustable.

Even more surprisingly, it was found that a permutation of the linker component, i.e. the calmodulin, resulted in even stronger change of binding of the polypeptide of the invention to its antigen compared to the use of the described WT CaM as linker, at least by a factor of 2, as shown in Example 5 (see also FIG. 5B, FIG. 5C, FIG. 5D). Regularly, in the art a permutation in comparable systems (polypeptides with antigen binding domains) has been used only with regard of the non-linker part.

Also unexpectedly the use of variants of the normally used M13 peptide or the use of other peptides than the M13 peptide in the herein disclosed system (or compositions) resulted in a stronger change of binding of the polypeptide as disclosed herein to its antigen compared to the use of the M13 peptide itself.

Best results with regard to a switchable binding modulation is achieved when permutated CaM is combined with variants of the M13 peptide or other peptides than the M13 peptide, some specific combinations of defined permutated CaMs and defined CaM binding peptides are especially preferred as disclosed herein.

Surprisingly, the change in binding of the antigen binding domains of the polypeptide triggered by the binding of a CaM binding molecule and ions to the calmodulin linker of the polypeptide can result either in an enhanced binding or in a reduced binding of the polypeptide to its antigen.

Polypeptides as disclosed herein can be released from the binding antigen by adding CaM binding molecules such as M13 peptide and ions such as $Ca^{2+}$ without harsh conditions. The general applicability of a calmodulin sequence as a universal linker to regulate the binding of a polypeptide comprising two immunoglobulin superfamily domains has been demonstrated herein firstly for different scFvs, including one specific for lysozyme, and secondly other scFvs with quite different affinities and antigen classes, including proteins and haptens. Herein compositions comprising the above mentioned components, methods for affecting the binding of the polypeptides, and the use of the polypeptides for affecting the binding of the polypeptides to their antigens are disclosed.

DETAILED DESCRIPTION OF THE INVENTION

Figure 1:
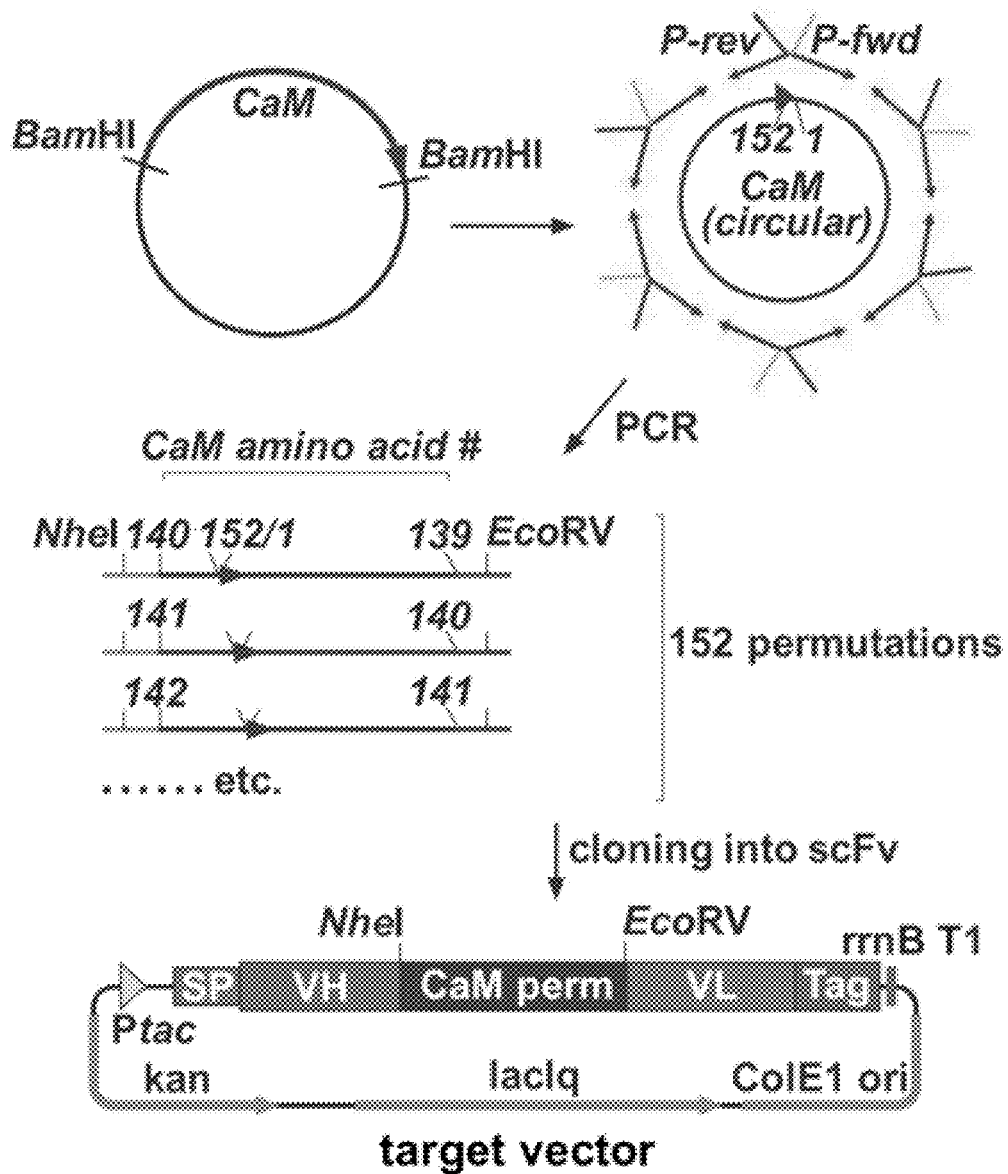
FIG. 1: Cloning of circularly permutated calmodulin variants.

In a first aspect the invention provides a composition (a system, a set, or a kit) comprising
i) a polypeptide comprising calmodulin and two immunoglobulin superfamily domains, wherein said two immunoglobulin superfamily domains are linked via said calmodulin; and
ii) a calmodulin binding molecule; and
iii) ions binding to the $Ca^{2+}$ binding site of calmodulin, wherein the binding of said calmodulin binding molecule and of said ions affects the binding of said polypeptide to an antigen to be bound by said polypeptide.

The calmodulin is a linker sequence between the two immunoglobulin superfamily domains and serves as a universal allosteric regulator of these two domains. The CaM (or the CaM sequence) may be any sequence or part of a sequence of CaM which maintains the characteristics of the WT calmodulin protein to bind both, ions at the $Ca^{2+}$ binding site and a calmodulin binding molecule, and thereby changing its conformation. This includes a calmodulin or a sequence of calmodulin having a sequence identity of at least 70%, or at least 75%, or at least 80%, or at least 85%, or at least 90%, or at least 95%, or at least 97%, or at least 98%, or at least 99% at the amino acid sequence level to the wild type calmodulin.

The sequence of calmodulin may also be a functional fragment of the full-length calmodulin protein (e.g. a truncated protein of calmodulin) or a fragment of the full-length calmodulin protein having a sequence identity of at least 70%, or at least 75%, or at least 80%, or at least 85%, or at least 90%, or at least 95%, or at least 97%, or at least 98%, or at least 99% at the amino acid sequence level to the corresponding part of said full-length calmodulin.

In general, all amino acid variations (i.e. substitutions, additions or eliminations of amino acids of the calmodulin) are included under this definition, which do not lead to the loss of the described characteristics of the calmodulin to provide the allosteric change, or a functional fragment thereof to bind both, ions at the $Ca^{2+}$ binding side and a calmodulin binding molecule, and thereby changing its conformation.

The composition as disclosed above, wherein said binding of said calmodulin-binding molecule and of said ions to the $Ca^{2+}$ binding site of calmodulin enhances or reduces the binding of said polypeptide to said antigen.

Said calmodulin binding molecule may be a calmodulin binding peptide. Said calmodulin binding peptide may be selected and derived from the group of naturally occurring calmodulin ligands consisting of myosin light chain kinase, caldesmon, calspermin, phosphofructokinase, calcineurin, calcium ATPase, spectrin, glutamate receptor, nitric oxidase synthase, serine/threonine-protein phosphatase, tumor necrosis factor receptor, estrogen receptor, calcium channel subunits and calcium/calmodulin-dependent protein kinases. Said CaM binding peptide may be M13 peptide derived from the rabbit myosin light chain kinase or a variant thereof.

Said calmodulin binding peptide may be selected from the group of peptides consisting of SEQ ID NO: 1 to SEQ ID NO: 65. Preferentially, said calmodulin binding peptide may be selected from the group of peptides consisting of SEQ ID NO: 1, SEQ ID NO: 2, SEQ ID NO: 3, SEQ ID NO: 7, SEQ ID NO: 8, SEQ ID NO: 9, SEQ ID NO: 46, SEQ ID NO: 47, SEQ ID NO: 49, SEQ ID NO: 51 and SEQ ID NO: 53.

But in general, any peptide or polypeptide which can bind to CaM and thereby provides the allosteric change may be used.

Three-dimensional structures of calmodulin in complex with high-affinity peptidic substrates are available (Montigiani et al., 996, *J. Mol. Biol.* 258:6-13). These peptides correspond to the calmodulin-binding regions of different protein kinases. Alternatively, methods such as peptide phage display, ribosome display or other established combinatorial selection systems well known in the art (see e.g. Ullman C G et al. *Brief Funct Genomics*, 2011 May; 10(3):125-34 or Galan A et al. *Mol Biosyst*, 2016 Jun. 16. [Epub ahead of print]) may be used to identify variants of naturally occurring sequences or synthetic sequences which can bind to calmodulin.

Said ions binding to the $Ca^{2+}$ binding site of calmodulin may be any ions that can be bound by the $Ca^{2+}$ binding site of calmodulin resulting in a conformational change of the CaM in the presence of a CaM binding molecule, preferentially said ions are calcium ions ($Ca^{2+}$).

Said calmodulin may be a permutated calmodulin. Generally, a permutated CaM can be generated e.g. by circular permutation, a general method for permutating proteins which is well known in the art (see e.g. "Circular Permutation of Proteins" in "Protein Engineering Handbook" (Ed.: Stefan Lutz, Uwe T. Bornscheuer) Wiley-VCH 2009), and as described herein.

Alternatively, a permutated CaM may be generated synthetically on nucleic acid or amino acid level, especially it may be generated synthetically when the sequence which is intended to use for the generation of the polypeptide as disclosed herein comprising the permutated CaM is known and can be generated purposefully.

Figure 2:
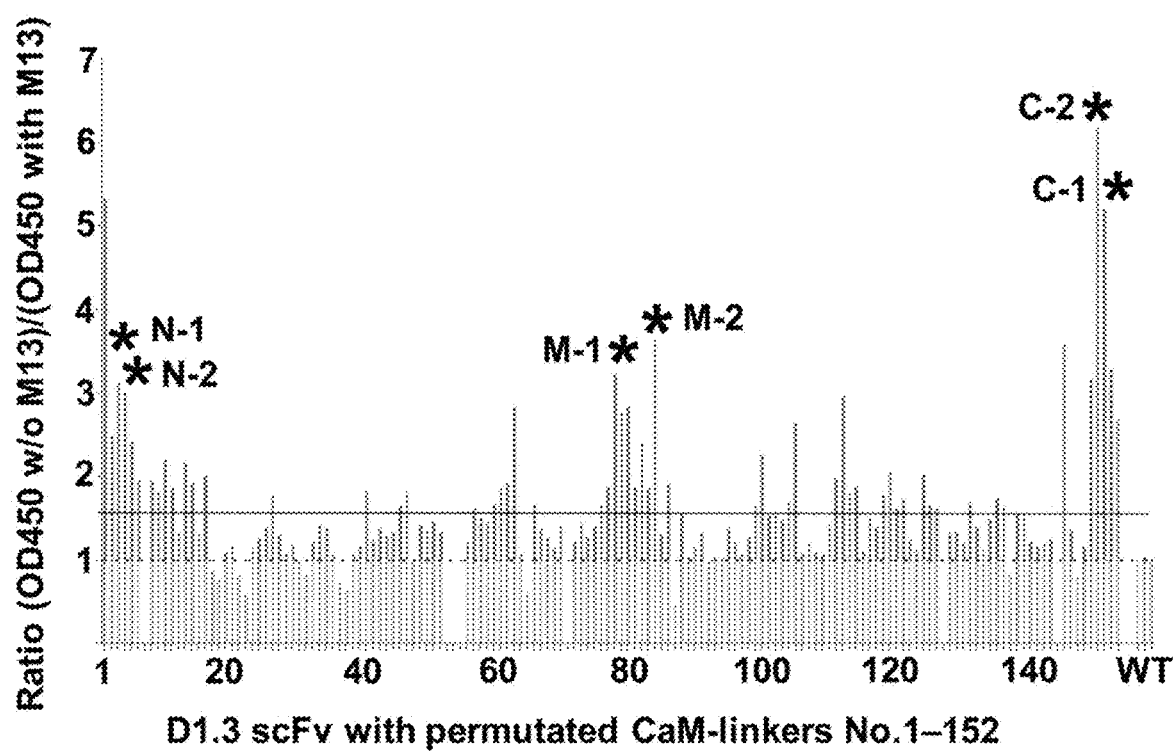
FIG. 2: Identification of switchable anti-lysozyme scFv-Calmodulin-variants by competitive ELISA.

As demonstrated herein the vast majority of permutated calmodulins generated and used herein induce a regulation of binding of the polypeptides as disclosed herein (FIG. 2) by addition of different CaM binding molecules and ions such as $Ca^{2+}$, wherein the regulation of binding is more distinct than the regulation by the wildtype CaM (FIG. 5 B,C,D).

Said polypeptide of said composition comprising said permutated calmodulin and said two immunoglobulin superfamily domains, wherein said two immunoglobulin superfamily domains are linked via said permutated calmodulin may be obtained e.g. by the method comprising
a) Creating at least one insertion nucleic acid sequence encoding a permutated calmodulin
b) Creating an acceptor nucleic acid sequence encoding a polypeptide comprising two immunoglobulin superfamily domains
c) Inserting the at least one insertion sequence of a) into the acceptor sequence of b), wherein one insertion sequence of a) is inserted between the parts of the acceptor sequence b) which encode the two immunoglobulin superfamily domains of b)
d) Transforming a host with the nucleic acid sequences of c)
e) Selecting for transformed hosts harboring the sequence (s) of c)
f) Screening for transformed hosts expressing polypeptides comprising two immunoglobulin superfamily domains linked via permutated calmodulin by exposing the polypeptides produced by the transformed hosts to said calmodulin-binding molecule and identifying the transformed hosts harboring polypeptides which impact the binding of said polypeptides to the antigen in the presence of ions binding to the Ca$^{2+}$ binding site of calmodulin.

The permutated calmodulin of the composition as described above may be selected from the group consisting of SEQ ID NO: 67 to SEQ ID NO: 123. Preferentially, the permutated calmodulin of the composition as described above may be selected from the group consisting of SEQ ID NO: 67 to SEQ ID NO: 72. Most preferentially, the permutated calmodulin may be selected from the group consisting of SEQ ID NO: 67, SEQ ID NO: 68, SEQ ID NO: 71 and SEQ ID NO: 72.

A preferred composition as disclosed herein may comprise
i) a polypeptide comprising calmodulin and two immunoglobulin superfamily domains, wherein said two immunoglobulin superfamily domains are linked via said calmodulin; and
ii) a calmodulin binding molecule; and
iii) ions binding to the Ca$^{2+}$ binding site of calmodulin,
wherein the binding of said calmodulin-binding molecule and of said ions affects the binding of said polypeptide to an antigen to be bound by said polypeptide,
wherein said permutated calmodulin has the sequence selected from the group consisting of sequences SEQ ID NO: 67 and SEQ ID NO: 68 and said calmodulin binding peptide has the sequence selected from the group consisting of sequences SEQ ID NO: 1, SEQ ID NO: 7, SEQ ID NO: 8, SEQ ID NO: 9 and SEQ ID NO: 46, or wherein said permutated calmodulin has the sequence SEQ ID NO: 68 and said calmodulin binding peptide has the sequence SEQ ID NO: 53, or wherein said permutated calmodulin has the sequence selected from the group consisting of sequences SEQ ID NO: 71 and SEQ ID NO: 72 and said calmodulin binding peptide has the sequence selected from the group consisting of sequences SEQ ID NO: 1, SEQ ID NO: 47, SEQ ID NO: 51 and SEQ ID NO: 53.

Said composition, wherein said polypeptide may be a single chain Fv (scFv) comprising the calmodulin and a variable region of a heavy chain of an immunoglobulin ($V_H$) and a variable region of a light chain of an immunoglobulin ($V_L$).

Especially preferred is a composition as described above, wherein the polypeptide comprising a scFv specific for the antigen CD14 and a permutated CaM has the sequence of SEQ ID NO: 124 and said CaM binding peptide has the sequence of SEQ ID NO: 1 or SEQ ID NO: 7 or SEQ ID NO: 8 or SEQ ID NO: 9, or said polypeptide has the sequence of SEQ ID NO: 125 and said CaM binding peptide has the sequence of SEQ ID NO: 1 or SEQ ID NO: 7 or SEQ ID NO: 8 or SEQ ID NO: 9 or SEQ ID NO: 53, or said polypeptide has the sequence of SEQ ID NO: 126 and said CaM binding peptide has the sequence of SEQ ID NO: 1 or SEQ ID NO: 47, or said polypeptide has the sequence of SEQ ID NO: 127 and said CaM binding peptide has the sequence of SEQ ID NO: 1 or SEQ ID NO: 47 or SEQ ID NO: 53.

Furthermore, especially preferred is a composition as described above, wherein the polypeptide comprising a scFv specific for biotin and a permutated CaM has the sequence of SEQ ID NO: 128 and said CaM binding peptide has the sequence of SEQ ID NO: 1 or SEQ ID NO: 46, or said polypeptide has the sequence of SEQ ID NO: 129 and said CaM binding peptide has the sequence of SEQ ID NO: 1 or SEQ ID NO: 46, or said polypeptide has the sequence of SEQ ID NO: 130 and said CaM binding peptide has the sequence of SEQ ID NO: 1 or SEQ ID NO: 53.

Moreover, especially preferred is a composition as described above, wherein the polypeptide comprising a scFv specific for the antigen CD4 and a permutated CaM has the sequence of SEQ ID NO: 131 and said CaM binding peptide has the sequence of SEQ ID NO: 1 or SEQ ID NO: 46, or said polypeptide has the sequence of SEQ ID NO: 132 and said CaM binding peptide has the sequence of SEQ ID NO: 1 or SEQ ID NO: 46, or said polypeptide has the sequence of SEQ ID NO: 133 and said CaM binding peptide has the sequence of SEQ ID NO: 1 or SEQ ID NO: 51 or SEQ ID NO: 53, or said polypeptide has the sequence of SEQ ID NO: 134 and said CaM binding peptide has the sequence of SEQ ID NO: 1 or SEQ ID NO: 51 or SEQ ID NO: 53.

As evident by FIGS. 7A, B and C (or Example 6) said combinations of specific sequences of permutated CaM and CaM binding peptides display the strongest changes in binding between said polypeptides and their antigens, respectively.

Said composition, wherein said polypeptide is part of an antigen binding domain of a chimeric antigen receptor (CAR). Said CAR may comprise an antigen binding domain, a transmembrane domain and cytoplasmic signaling domain (s).

In a further aspect the invention provides a method for affecting the binding of a polypeptide to an antigen to be bound, wherein said polypeptide comprises a calmodulin and two immunoglobulin superfamily domains wherein said two immunoglobulin superfamily domains are linked via said calmodulin, the method comprising the step of contacting said polypeptide with a calmodulin binding molecule in the presence of ions binding to the $Ca^{2+}$ binding site of calmodulin, thereby affecting the binding of said polypeptide to the antigen.

Preferentially, the CaM is a permutated CaM as described above.

Preferentially the CaM binding molecule is a CaM binding peptide as described above.

Said method for affecting the binding of a polypeptide, wherein before said contacting of said calmodulin binding molecule with said calmodulin said polypeptide is contacted with the antigen to be bound by said polypeptide, and wherein said contacting of said calmodulin binding molecule to said calmodulin in the presence of ions binding to the $Ca^{2+}$ binding site of calmodulin affects the binding of said polypeptide to the antigen. Said affecting of the binding may be a reduction (decrease) of binding, thereby releasing the polypeptide from the antigen.

Alternatively, said affecting of the binding may be an enhancement (an increase) of binding, thereby enhancing the binding between said polypeptide and the antigen. Enhancing said binding may be of interest when the binding of said polypeptide to the antigen is weak or does not occur in the absence of said CaM binding molecule and said ions binding to the $Ca^{2+}$ binding site of CaM.

Said affecting of the binding may be a change of one or both of the kinetic properties of the binding reaction (the association and dissociation rate constants, or on-rate and off-rate) while overall affinity may be changed (affecting the affinity) in this process or remain the same (affecting the binding kinetics but not the equilibrium affinity), thereby changing the kinetics of the interaction of the polypeptide with the antigen.

Said affecting of binding may be an allosteric change induced within the antigen.

In another aspect the invention provides the use of a polypeptide (as described above) comprising a calmodulin, preferentially a permutated calmodulin, and two immunoglobulin superfamily domains, wherein said two immunoglobulin superfamily domains are linked via said calmodulin, preferentially said permutated calmodulin, for affecting in the presence of a calmodulin binding molecule and ions binding to the $Ca^{2+}$ binding site of calmodulin the binding of said polypeptide to an antigen to be bound by said polypeptide.

Exemplary Embodiments

In one embodiment of the invention the composition comprises
  i) a polypeptide such as a scFv, e.g. lysozyme binding scFv D1.3, having the sequence of SEQ ID NO: 135, comprising calmodulin such as a permutated CaM, e.g. having the sequence of the group consisting of SEQ ID NO: 67 to SEQ ID NO: 123 and two immunoglobulin superfamily domains such as a variable region of a heavy chain of an immunoglobulin ($V_H$) and a variable region of a light chain of an immunoglobulin ($V_L$), wherein said two immunoglobulin superfamily domains are linked via said calmodulin; and
  ii) a calmodulin binding molecule such as M13 peptide; and
  iii) ions binding to the $Ca^{2+}$ binding site of calmodulin such as $Ca^{2+}$,
  wherein the binding of said calmodulin-binding molecule and of said ions to said $Ca^{2+}$ binding site of calmodulin affects the binding of said polypeptide to an antigen such as lysozyme by reducing said affinity.

In one embodiment of the invention the composition may be used for enrichment (e.g. positive selection) of cells expressing on the cell surface the antigen recognized by the polypeptide, e.g. as disclosed herein. Methods suited for enrichment are well known in the art and include but are not limited to flow cytometry such as fluorescence activated cell sorting (FACS) or magnetic cell separation such as MACS® (Miltenyi Biotec GmbH).

Exemplarily the principle of MACS® separation (Miltenyi Biotec GmbH, Germany) is described here: The polypeptide as disclosed herein, specific for an antigen can be used for direct or indirect magnetic labeling of cells expressing said antigen on their cell surface in a sample comprising said cells and other cells (not expressing said antigen). First the antigen-expressing cells are magnetically labeled with MicroBeads (magnetic particles) conjugated to said polypeptide. Then the cell sample is loaded on a MACS® Column which is placed in the magnetic field of a MACS® Separator. The magnetically labeled antigen-expressing cells are retained on the column. The unlabeled cells run through. The addition of an "elution" solution comprising a CaM binding molecule such as M13 peptide and e.g. $Ca^{2+}$ ions allow to reduce the binding of the polypeptide to the antigen, thereby releasing the cell expressing said antigen from the immobilized polypeptide conjugated to the magnetic particle, i.e. the cell can be eluted from the column without the need of removal of the magnetic field.

In one embodiment of the invention the composition may be used for the enrichment (i.e. purification) of proteins fused to an antigen recognized by the polypeptide comprising a scFv comprising calmodulin, preferentially a permutated CaM, and a variable region of a heavy chain of an immunoglobulin and a variable region of a light chain of an immunoglobulin, wherein said variable regions are linked via said calmodulin, preferentially permutated CaM. The polypeptide invention as described herein may be immobilized e.g. on a resin. Next, target protein (i.e. protein which has to be purified) containing material is incubated with the polypeptide-coupled resin to allow for the binding of the polypeptide to the target protein fused to an antigen recognized by the polypeptide invention. Unbound material is removed by washing of the resin material. The addition of an "elution" solution comprising a CaM binding molecule such as M13 peptide and e.g. $Ca^{2+}$ ions allow to reduce the binding of the polypeptide to the antigen-comprising target protein, thereby releasing the target protein without the need of harsh elution conditions.

In one embodiment of the invention the polypeptide is a scFv comprising the calmodulin, preferentially a permutated CaM, and a variable region of a heavy chain of an immunoglobulin and a variable region of a light chain of an immunoglobulin, wherein said variable regions are linked via said calmodulin, preferentially permutated CaM, and wherein said scFv is the antigen-binding domain (or part of the antigen-binding domain) of a chimeric antigen receptor (CAR). The CAR may comprise said antigen binding domain, a transmembrane domain and cytoplasmic signaling domains. Said CAR may be released from an antigen bound to said CAR by contacting said CAR with a CaM binding molecule and ions binding to the $Ca^{2+}$ binding site of CaM, if said contacting results in a reduction of binding of the antigen binding domain to the antigen. Alternatively, said CAR may bind sufficiently strong to the antigen to induce or activate signaling in the cell expressing said CAR not until a CaM binding molecule and ions binding to the $Ca^{2+}$ binding site of CaM are contacted with said CAR, if said contacting results in an increase of binding of the antigen binding domain to the antigen. These procedures allow a control of interactions between cells expressing said CAR and the antigen by providing a small peptide, as calcium may be present in sufficient amounts physiologically. This may help to reduce or prevent severe side effects in a patient if cells expressing said CAR are used in a cell immunotherapy e.g. to fight cancer cells in a patient.

In one embodiment of the invention the composition is a composition comprising
  i) a polypeptide comprising a permutated calmodulin and two immunoglobulin superfamily domains, wherein said two immunoglobulin superfamily domains are linked via said calmodulin,
  ii) a calmodulin binding molecule; and
  iii) ions binding to the $Ca^{2+}$ binding site of calmodulin, wherein the binding of said calmodulin-binding molecule and of said ions affects the binding of said polypeptide to an antigen to be bound by said polypeptide, and wherein said polypeptide is obtainable by the method comprising the steps of
    α) a) creating an insertion nucleic acid sequence library, wherein said insertion sequence comprises a sequence which encodes said permutated calmodulin comprising the steps of:
      i) obtaining an insertion nucleic acid sequence which encodes calmodulin that binds a calmodulin-binding molecule and ions that bind to the $Ca^{2+}$ binding site of calmodulin;
      ii) ligating said insertion nucleic acid sequence to circularize said insertion nucleic acid sequence;
      iii) creating oligonucleotide pairs which allow the amplification of said permutated insertion nucleic acid sequence by polymerase chain reaction using the circularized insertion nucleic acid sequence of ii) as a template and which furthermore comprise nucleic acid overhangs with recognition sequences of restriction enzymes iv) performing a polymerase chain reaction using the circularized insertion nucleic acid sequence of ii) and the oligonucleotide pairs of iii) to allow the amplification of said permutated insertion nucleic acid sequence;
v) digesting said permutated insertion nucleic acid sequence of iv) with restriction enzymes recognizing said recognition sequences to allow the specific introduction of the digested insertion nucleic acid sequence into the acceptor nucleic acid sequence;

b) creating an acceptor nucleic acid sequence, wherein said acceptor nucleic acid sequence comprises a sequence which encodes said two immunoglobulin superfamily domains, comprising the steps of:
i) obtaining said acceptor nucleic acid sequence comprising the same recognition sequences of restriction enzymes of a)iii) between the sequences which encode said two immunoglobulin superfamily domains;
ii) digesting said acceptor nucleic acid sequence of i) with said restriction enzymes recognizing said recognition sequences that allow the introduction of the permutated insertion nucleic acid sequence of a)v) between the two immunoglobulin superfamily domains of said acceptor nucleic acid sequence;

c) ligating the nucleic acids of a)v) and b)ii) so that an insertion nucleic acid sequence inserts into the digested acceptor nucleic acid sequence;

d) transforming a host with one or a library of the ligated sequences of c);

e) selecting for transformed hosts harboring the ligated nucleic acid sequences;

f) screening for transformed hosts expressing polypeptides comprising two immunoglobulin superfamily domains linked via calmodulin by exposing the polypeptides produced by the transformed hosts to said calmodulin-binding molecule and identifying the transformed hosts harboring polypeptides which impact the binding of said polypeptides to the antigen in the presence of ions binding to the $Ca^{2+}$ binding site of calmodulin; or β) a) creating an insertion nucleic acid sequence library, wherein said insertion sequence comprises a sequence which encodes said permutated calmodulin comprising the steps of:
i) obtaining an insertion nucleic acid sequence which encodes calmodulin that binds a calmodulin-binding molecule and ions that bind to the $Ca^{2+}$ binding site of calmodulin;
ii) ligating said insertion nucleic acid sequence to circularize said insertion nucleic acid sequence;
iii) digesting the insertion nucleic acid sequence of ii) to randomly introduce a single double-stranded break for the creation of an insertion nucleic acid sequence library;

b) creating an acceptor nucleic acid sequence, wherein said acceptor nucleic acid sequence comprises a sequence which encodes said two immunoglobulin superfamily domains, comprising the steps of:
i) obtaining said acceptor nucleic acid sequence;
ii) digesting said acceptor nucleic acid sequence of i) with restriction enzymes recognizing recognition sequences that allow the introduction of the insertion nucleic acid sequence library between the two immunoglobulin superfamily domains of said acceptor nucleic acid sequence; optionally
iii) blunt ending said acceptor sequence if said restriction enzymes produce sticky ends c) ligating the nucleic acids of the library of a)iii) and b)ii), optionally b)iii) so that an insertion nucleic acid sequence inserts into the digested acceptor nucleic acid sequence;

d) transforming a host with the library of the ligated sequences of c);

e) selecting for transformed hosts harboring the ligated nucleic acid sequences;

f) screening for transformed hosts expressing polypeptides comprising two immunoglobulin superfamily domains linked via calmodulin by exposing the polypeptides produced by the transformed hosts to said calmodulin-binding molecule and identifying the transformed hosts harboring polypeptides which impact the binding of said polypeptides to the antigen in the presence of ions binding to the $Ca^{2+}$ binding site of calmodulin; or γ) a) creating an insertion nucleic acid sequence or a sequence library which encodes said permutated calmodulin comprising the steps of:
i) synthetically generating said nucleic acid sequence of said permutated calmodulin comprising nucleic acid overhangs with recognition sequences of restriction enzymes;
ii) digesting said permutated insertion nucleic acid sequence of i) with restriction enzymes recognizing said recognition sequences to allow the specific introduction of the digested insertion nucleic acid sequence into the acceptor nucleic acid sequence;

b) creating an acceptor nucleic acid sequence, wherein said acceptor nucleic acid sequence comprises a sequence which encodes said two immunoglobulin superfamily domains, comprising the steps of:
i) obtaining said acceptor nucleic acid sequence comprising the same recognition sequences of restriction enzymes of a)i) between the sequences which encode said two immunoglobulin superfamily domains;
ii) digesting said acceptor nucleic acid sequence of i) with said restriction enzymes recognizing said recognition sequences that allow the introduction of the permutated insertion nucleic acid sequence of a)ii) between the two immunoglobulin superfamily domains of said acceptor nucleic acid sequence;

c) ligating the nucleic acids of a)ii) and b)ii) so that an insertion nucleic acid sequence inserts into the digested acceptor nucleic acid sequence;

d) transforming a host with one or a library of the ligated sequences of c);

e) selecting for transformed hosts harboring the ligated nucleic acid sequences;

f) screening for transformed hosts expressing polypeptides comprising two immunoglobulin superfamily domains linked via calmodulin by exposing the polypeptides produced by the transformed hosts to said calmodulin-binding molecule and identifying the transformed hosts harboring polypeptides which affect the binding of said polypeptides to the antigen in the presence of ions binding to the $Ca^{2+}$ binding site of calmodulin; or δ) a) creating the nucleic acid sequences encoding said polypeptide comprising said permutated calmodulin by synthetically creating said nucleic acid sequences b) transforming a host with one or a library of the sequences of a);

c) selecting for transformed hosts harboring the nucleic acid sequences;
d) screening for transformed hosts expressing polypeptides comprising two immunoglobulin superfamily domains linked via calmodulin by exposing the polypeptides produced by the transformed hosts to said calmodulin-binding molecule and identifying the transformed hosts harboring polypeptides which impact the binding of said polypeptides to the antigen in the presence of ions binding to the $Ca^{2+}$ binding site of calmodulin.

Definitions

Unless defined otherwise, technical and scientific terms used herein have the same meaning as commonly understood by one of ordinary skill in the art to which this invention belongs.

The term "calmodulin" or "sequence of calmodulin" as used herein refers to a sequence having a sequence identity of at least 70%, or at least 75%, or at least 80%, or at least 85%, or at least 90%, or at least 95%, or at least 97%, or at least 98%, or at least 99% at the amino acid sequence level to the wild type calmodulin (SEQ ID NO: 66) if the calmodulin did not experience a permutation. In this context, "sequence identity" may be determined using pairwise alignments using alignments programs for amino acid sequences well known to the art.

The sequence of calmodulin may also be a functional fragment of the full-length calmodulin protein (e.g. a truncated protein of calmodulin) or a fragment of the full-length calmodulin protein having a sequence identity of at least 70%, or at least 75%, or at least 80%, or at least 85%, or at least 90%, or at least 95%, or at least 97%, or at least 98%, or at least 99% at the amino acid sequence level to the corresponding sequence of said full-length calmodulin if this part of the calmodulin sequence did not experience a permutation.

In general, all amino acid variations (i.e. substitutions, additions or eliminations of amino acids of the calmodulin) are included under this definition, which do not lead to the loss of the function of the calmodulin or a functional fragment thereof to provide the change of its conformation.

The calmodulin or a functional fragment thereof (in all its variants as described above) may be also a permutated calmodulin or functional fragment thereof. Although the order of sequence may be changed in a permutated calmodulin it maintains the characteristics of the WT calmodulin to bind both, ions at the $Ca^{2+}$ binding site and a calmodulin binding molecule, and thereby changing its conformation (i.e. the fragment of the calmodulin remains functional). A permutated CaM may be generated e.g. by a method using circular permutation.

A circular permutation is a relationship between proteins whereby the proteins have a changed order of amino acids in their peptide sequence. The result is a protein structure with different connectivity, but overall similar three-dimensional (3D) shape.

Circular permutation can occur as the result of natural evolutionary events, posttranslational modifications, or artificially engineered mutations.

Because of this, it is often possible to design circular permutations of proteins. Today, circular permutations are generated routinely in the lab using standard genetics techniques (see e.g. "Circular Permutation of Proteins" in "Protein Engineering Handbook" (Ed.: Stefan Lutz, Uwe T. Bornscheuer) Wiley-VCH 2009).

A permutated calmodulin as used herein may also have some additional amino acid residues in its sequence. This may be the result of the generation of a permutated CaM due to e.g. addition of recognition sequences of restriction enzymes on the level of the nucleic acid sequence of said calmodulin. The additional sequence may be any sequence, preferentially the sequence may be a sequence which does not result in larger conformational changes (or any change at all) when the position of said additional sequence changes within the polypeptide, e.g. due to the permutation process of the CaM including said additional sequence. In this context a well-suited additional sequence may be the amino acid sequence GGSG within the permutated CaM as the result of the nucleic acid sequence recognized by the restriction enzyme BamHI, which may be used at the ends of the nucleic acid sequence of CaM, resulting in the additional sequence on the amino acid level of GGSG after digestion of the nucleic acid sequence with BamHI and subsequent circularization of the sequence and translation into a polypeptide. This additional sequence leads to minor or no conformational changes regardless of the position within the permutated CaM and does not affect the binding of the polypeptide as disclosed herein to its antigen.

Generally, the permutation of the calmodulin linker as disclosed herein may be at any position of the calmodulin sequence, preferentially the permutated calmodulins (the permutated calmodulin linkers) are C-terminally permutated variants or those permutated in the middle of the former calmodulin encoding gene.

Although some permutation sites prevent the protein from folding correctly, many permutants have been created with nearly identical function to the original protein.

The term "permutated calmodulin" as used herein refers to any calmodulin derived amino acids sequence which has an altered order of amino acids in its peptide sequence compared to the WT calmodulin sequence but saves the characteristics of the CaM to change its conformation when the altered sequence of the CaM binds a CaM binding molecule and ions binding to the $Ca^{2+}$ binding site of the CaM, wherein said conformational change affects the binding of the polypeptide as disclosed herein to its antigen.

The term "two immunoglobulin superfamily domains" in the context of "a polypeptide comprising calmodulin and two immunoglobulin superfamily domains" as used herein refers to the use of two domains associated with the immunoglobulin superfamily within said polypeptide. In general, all amino acid variations (i.e. substitutions, additions or eliminations) of amino acids of an immunoglobulin superfamily domain are included under this definition, which do not lead to the loss of the domain function which is to contribute to antigen binding. The immunoglobulin superfamily is a large group of cell surface and soluble proteins that are mainly involved in the recognition, binding, or adhesion processes of cells. Molecules categorized as members of this superfamily based on shared structural features with immunoglobulins; they all possess a domain known as an immunoglobulin domain or fold. Members of the immunoglobulin superfamily include cell surface antigen receptors, co-receptors and co-stimulatory molecules of the immune system, molecules involved in antigen presentation to lymphocytes, cell adhesion molecules, certain cytokine receptors and intracellular muscle proteins. A specific example of the "two immunoglobulin superfamily domains" is an Fv fragment of an immunoglobulin, comprising a variable region of a heavy chain of an immunoglobulin and a variable region of a light chain of an immunoglobulin.

A single-chain variable fragment (scFv) is a fusion protein of the variable regions of the heavy ($V_H$) and light chains ($V_L$) of immunoglobulins, normally connected with a short linker peptide of up to about 25 amino acids. The linker is often rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. In the present invention the linker is replaced by the calmodulin sequence. Another specific example of the "two immunoglobulin superfamily domains" are the variable chains of the T cell receptors, which share overall structural properties very similar to the Fv fragment, and constitute a scTv containing the calmodulin sequence as a linker. These scTv can include the variable regions of the α- and β-chain or the variable regions of the γ- and δ-chains.

As used herein, the term "antigen" is intended to include substances that bind to or evoke the production of one or more antibodies or bind to the above mentioned scFv, scTv or analogous binding entities composed of two immunoglobulin superfamily members. Each antibody binds to a specific antigen by way of an interaction similar to the fit between a lock and a key. The substance may be from the external environment or formed within the body. The term "antigen" comprises, but is not limited to, proteins, peptides, polypeptides, oligopeptides, lipids, carbohydrates, haptens, vitamins, hormones, synthetic molecules, and combinations thereof, for example a glycosylated protein, a glycolipid or a biotinylated vitamin. An antigen may be on the cell surface or inside the cell. Preferentially, an antigen is on the cell surface of a cell. In another embodiment, the antigen is in solution in a complex mixture of other substances, like in the cultivation supernatant of a bioreactor or a fraction derived thereof. In another embodiment, the antigen is in solution in a complex mixture of other proteins, like blood plasma or other body fluids or a bioreactor cultivation medium supernatant.

The area of the antibody which is located towards the antigen and includes amino acid side chains forming chemical linkages like hydrogen bonds, electrostatic bonds or hydrophobic interactions with the antigen, is termed "paratope". It is an effect to achieve by the present invention to influence the structure of this paratope in a way that its binding to the antigen is influenced by altering the position, orientation, distance or binding energy of one or several said amino acid side chains or of the entire V domain to the antigen.

The terms "specifically binds to" or "specific for" with respect to an antigen-binding domain of an antibody or fragment thereof (e.g. a scFv or scTv) refer to an antigen-binding domain which recognizes and binds to a specific antigen, but does not substantially recognize or bind other antigens in a sample. An antigen-binding domain that binds specifically to an antigen from one species may bind also to the homologous antigen from another species. This cross-species reactivity is typical to many antibodies and therefore not contrary to the definition of that antigen-binding domain as specific. An antigen-binding domain that specifically binds to an antigen may bind also to different allelic forms of the antigen (allelic variants, splice variants, isoforms etc.) or homologous variants of this antigen from the same gene family. These cross reactivities are typical to many antibodies and therefore not contrary to the definition of that antigen-binding domain as specific. An antigen-binding domain that specifically binds to an antigen may bind also to a limited number of completely different structures, known as mimotopes (see e.g. Reineke U. et al., *J Immunol Methods*. 2002 Sep. 1; 267(1):37-51; Keitel T. et al., *Cell*. 1997 Dec. 12; 91(6):811-20). This reactivity is typical to many antibodies and therefore not contrary to the definition of that antigen-binding domain as specific.

The term "affecting the binding" as used herein refers to a change of one or both of the kinetic properties of the binding reaction (the association and dissociation rate constants) while overall affinity may be changed (affecting the equilibrium affinity) in this process or remain the same (affecting the binding kinetics but not the affinity), thereby changing the kinetics of the interaction of the polypeptide as disclosed herein with the antigen.

The term "affinity" refers to the strength of the sum total of non-covalent interactions between a single binding site of a molecule (e.g., the antigen binding domain(s) of a polypeptide such as the variable domains of a light and heavy chain of immunoglobulins in a scFv) and its binding partner (e.g., an antigen). Unless indicated otherwise, as used herein, "binding affinity" refers to intrinsic binding affinity which reflects a 1:1 interaction between members of a binding pair (e.g., antigen-binding polypeptide and its antigen). The affinity of a molecule X for its partner Y can generally be represented by the equilibrium dissociation constant ($K_D$). Affinity can be measured by common methods known in the art (e.g., Biacore™ measurement, and calculated from the dissociation and association constants).

The terms "regulation", "modulation", "affecting" "influence", and "change" in the context of the regulation/modulation/affecting/influence/change of the binding of the polypeptide as disclosed herein to its antigen can be used interchangeably. Regulation of binding as used herein means a conformation or entropy change in the calmodulin linker of the polypeptide between the two immunoglobulin superfamily domains, e.g. the $V_H$ and $V_L$ regions of a scFv fragment, triggered by the contact of the calmodulin linker with a calmodulin binding molecule and ions that bind to the $Ca^{2+}$ binding site of the CaM that affect the conformation of the antigen binding site, resulting in a (measurable) change of the binding. The change of the binding may be a reduction (decrease) of binding or an enhancement (an increase) of binding or a change of dissociation or association rate constants of the polypeptide as disclosed herein to its antigen.

The binding of i) a calmodulin binding molecule and ii) ions binding to the $Ca^{2+}$ binding site of calmodulin as used herein has to be a concerted binding, i.e. both components have to be bound to the CaM of the polypeptide to affect the modulation of said binding. In one embodiment of the invention ions binding to the $Ca^{2+}$ binding site of calmodulin and the polypeptide of the invention may be present in the same solution (which is not sufficient to induce the modulation of said binding) but not before the addition of a CaM binding molecule will lead to the modulation of the binding of the polypeptide as disclosed herein (as now a concerted binding of both, a calmodulin binding molecule and ions binding to the $Ca^{2+}$ binding site of calmodulin to said polypeptide is possible).

The term "polypeptide comprising calmodulin and two immunoglobulin superfamily domains, wherein said two immunoglobulin superfamily domains are linked via said calmodulin" as used herein refers to a polypeptide having the following domains in an order of: a first immunoglobulin superfamily domain—calmodulin—a second immunoglobulin superfamily domain. Preferentially, the linkage between all these partial sequences (or domains) is via peptide bonds resulting in a continuous amino acid sequence of the polypeptide. Alternatively, the polypeptide may be a polypeptide having said domains (peptides) in above mentioned order but the connection between one, more or all of these domains (peptides) may be by covalent or non-covalent bounds other than the peptide bond, e.g. a disulphide bridge (S—S bond) between two domains such as a first disulphide bridge between a $V_H$ domain and the calmodulin and a second disulphide bridge between a $V_L$ domain and the calmodulin. The polypeptide comprising calmodulin and two immunoglobulin superfamily domains may also be assembled in part or completely by protein assembly methods using Sortase, Peptide Ligase, Protein Splicing or other methods well known in the art to connect protein domains based on suitable recognition sequences or tags (see e.g. van Vught R et al., *Comput Struct Biotechnol J.*, 2014 Feb. 14; 9:e201402001). The polypeptide comprising calmodulin and two immunoglobulin superfamily domains may also be assembled in part or completely by chemical bonds forming by CLICK-chemistry after recombinant insertion of non-natural amino acids into the said protein domains using methods well known in the art (see e.g. Maruani A et al., *Org Biomol Chem.*, 2016 Jul. 14; 14(26):6165-78). In one embodiment, the linkage can be achieved by producing a polypeptide from an assembled gene using appropriate recombinant production systems. In one embodiment, this production can be achieved by transforming bacterial or eukaryotic cells with an appropriate expression vector. In another embodiment, the linkage can be achieved by forming one or more suitable covalent bonds between one or both immunoglobulin superfamily domains and the calmodulin. In this case, the immunoglobulin superfamily domains and the calmodulin can be produced by different known methods, and linked after the production. In one embodiment, this production can be achieved by transforming bacterial or eukaryotic cells with appropriate expression vectors to produce the separate fragments. In one embodiment, this production can be achieved by peptide synthesis.

The term "calmodulin binding molecule" as used herein refers to any molecule which can bind to calmodulin and which can trigger a conformational or stability change in the presence of ions that bind to the $Ca^{2+}$ binding site of CaM resulting in the modulation of the binding of the polypeptide as disclosed herein. Said CaM binding molecule is not part of the polypeptide as disclosed herein, it is a free molecule which can bind to said polypeptide via binding sites of the calmodulin to said CaM binding molecule. Said calmodulin binding molecule may be a calmodulin binding peptide. Said CaM binding peptide may be M13 peptide derived from the myosin light chain kinase or a variant thereof. Alternatively, said CaM binding peptide may be another peptide than M13 peptide, e.g. another naturally occurring peptide or synthetically generated peptide. Said calmodulin binding peptide may be selected from the group consisting of SEQ ID NO: 1 to SEQ ID NO: 65. Preferentially, said calmodulin binding peptide may be selected from the group of peptides consisting of SEQ ID NO: 1, SEQ ID NO: 2, SEQ ID NO: 3, SEQ ID NO: 7, SEQ ID NO: 8, SEQ ID NO: 9, SEQ ID NO: 46, SEQ ID NO: 47, SEQ ID NO: 49, SEQ ID NO: 51 and SEQ ID NO: 53.

But in general, any peptide or polypeptide which can bind to CaM may be used.

Three-dimensional structures of calmodulin in complex with high-affinity peptidic substrates are available (Montigiani et al., 996, *J. Mol. Biol.* 258:6-13). These peptides correspond to the calmodulin-binding regions of different protein kinases. Alternatively, methods such as peptide phage display may be used to identify further sequences which can bind to calmodulin and cause the conformation change.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

EXAMPLES

Hereinafter, the present invention is described in more detail and specifically with reference to the examples, which however are not intended to limit the present invention.

Example 1: Generation of Permutated Calmodulin-scFv-Fusions

To identify the optimal arrangement of calmodulin to achieve the effect of a conformation change affecting antibody binding when inserted between the $V_H$ and $V_L$ antigen binding regions of an antibody, a gene library of 152 different variants representing all possible insertion points throughout a circularized calmodulin molecule was generated.

First, the gene encoding for human calmodulin (SEQ ID NO: 66) was optimized for recombinant expression in *E. coli*, flanking sequences encoding for BamHI recognition sites were added and the construct was synthesized by DNA2.0 (Menlo Park, USA). Circular permutation of the gene was performed by polymerase chain reaction (PCR) (FIG. 1). First, the plasmid bearing the gene of interest was amplified in *E. coli* NEB® 5-alpha (New England Biolabs, Frankfurt a.M., Germany) and purified by using the NucleoBond® Xtra Maxi Plasmid Purification Kit (Macherey-Nagel, Duren, Germany). Next, the gene encoding for calmodulin was excised from the plasmid by restriction with BamHI (all enzymes were obtained from New England Biolabs, Frankfurt a.M., Germany, if not indicated otherwise), gel electrophoresis and extraction of the fragment by utilizing the NucleoSpin® Gel and PCR clean-up Kit (Macherey-Nagel, Duren, Germany). Thereafter, the fragment was circularized by ligation with T4 DNA ligase (incubation overnight at 16° C.). The DNA concentration did not exceed 2.5 ng/μL in the reaction mixture to prevent the formation of multimers. The reaction was stopped by incubation at 65° C. for 10 min and circular forms were isolated by gel electrophoresis and gel extraction. The circularized DNA fragment was used as template for the generation of permutated variants by PCR. 152 different oligonucleotide pairs (obtained from Metabion, Planegg/Steinkirchen, Germany) were designed for the amplification of all possible permutated variants of calmodulin. The forward-oligonucleotides contained overlapping sequences encoding for NheI recognition sites, while the reverse-oligonucleotides included overhangs encoding for EcoRV restriction sites to facilitate cloning of the PCR products into the target vector. PCR was performed with Phusion® High-Fidelity DNA Polymerase as indicated in the manufacturer's manual. The size of the products was verified by gel electrophoresis and the remaining reaction mixture was desalted by using the NucleoSpin® Gel and PCR clean-up Kit, followed by restriction with NheI and EcoRV. The reaction was stopped by incubation at 80° C. for 20 min and directly used for ligation into the vector backbone, which had been equally treated with NheI and EcoRV and afterwards purified by gel electrophoresis and extraction. Partial blunt-end ligation was performed with T4 DNA ligase according to the manufacturer's instructions. After incubation overnight at 16° C., the reaction was stopped (65° C., 10 min) and directly transformed into the expression strain *E. coli* W3110 using standard protocols. Positive clones were identified by colony PCR using RED-Taq® DNA Polymerase (Sigma-Aldrich, Munich, Germany) and sequencing (GATC Biotech, Cologne, Germany).

Of the resulting 152 different PCR products, 145 could be cloned successfully as a linker into the lysozyme binding scFv (D1.3 scFv-WT without CaM-linker: SEQ ID NO: 135).

Example 2: Identification of Switchable Anti-Lysozyme scFv-Calmodulin-Variants

Calmodulin conformation has been shown to change when binding to the calmodulin-binding peptide M13 (residues 577-602 of skeletal muscle myosin light chain kinase). To test the influence of M13 peptide on the calmodulin-scFv fusion proteins, all constructs were produced in *E. coli* in microtiter plate format. Cells harboring the desired construct were grown overnight at 37° C. and 1000 rpm in 96-well polypropylene U-bottom plates (Greiner Bio-One, Solingen, Germany) in 180 µL 2×YP-GK-medium (2×YP-medium [16 g L$^{-1}$ soy peptone, 10 g L$^{-1}$ yeast extract, 5 g L$^{-1}$ NaCl, pH 7.0] containing 100 mM glucose and 50 µg/mL kanamycin) per well. The next day, 170 µL fresh medium was inoculated with 5 µL overnight culture and shaken at 1000 rpm for 6 h at 30° C. Protein expression was induced with a final concentration of 0.2 mM IPTG and cultures were incubated overnight at 25° C. Bacteria were harvested by centrifugation (4000 g, 20 min, 4° C.) and stored at −20° C. or directly processed for enzyme-linked immunosorbent assay (ELISA) screening. For periplasmic extraction of target protein, the pellets were resuspended in 100 µL TE-buffer (100 mM Tris, 10 mM EDTA; pH 9.0) per well and shaken for 2 h at 37° C. and 1000 rpm. The protein containing supernatant was separated from the cells by centrifugation (4000 g, 20 min, RT) and directly used for ELISA.

D1.3 scFv-CaM-variants showing modified binding properties towards the antigen (lysozyme) in presence of M13 peptide were identified by competitive ELISA. 100 ng of lysozyme was coated to 96-well Nunc MaxiSorp® ELISA plates (Thermo Fisher Scientific, Dreieich, Germany) in 1× tris-buffered saline (TBS) (50 mM Tris, 150 mM NaCl; pH 8.0) overnight at 4° C. The next day, plates were washed three times with 1×TBST (1×TBS+0.05% [v/v] Tween®20; pH 8.0) and afterwards blocked with 1×B-TBS (1×TBS+1% [w/v] bovine serum albumin; pH 8.0) for at least 1 h at RT. Crude lysates from microtiter plate expression were diluted 1:10 in 1×B-TBS/5 mM CaCl$_2$ (setup A) or 1×B-TBS/5 mM CaCl$_2$/1 µM M13 peptide (Anaspec, Fremont, USA) (setup B). Purified scFvs were also diluted in the mentioned buffers to appropriate concentrations (0.1 µM). The diluted scFvs were preincubated in 96-well polypropylene plates (Greiner Bio-One, Solingen, Germany) for 1 h at RT and afterwards 100 µL of the protein solution was transferred to the blocked and washed (three times with 1×TBST) ELISA plates. After incubation at RT for 1.5 h, plates were washed again (three times with 1×TBST) and horseradish peroxidase (HRP)-conjugated anti-His-antibody (1:10,000 diluted in 1×B-TBS, 100 µL per well; Miltenyi Biotec, Bergisch Gladbach, Germany) was added for detection of bound scFv-fusions. After another washing step, visualization of bound antibody-complexes was performed by addition of 100 µL TMB (3,3',5,5'-Tetramethylbenzidine) substrate (Seramun Diagnostica, Heidesee, Germany) per well. The reaction was stopped with 100 µL 0.5 M H$_2$SO$_4$ and absorbance (450 nm) was measured with a Versamax® ELISA microplate reader (Molecular Devices, Sunnyvale, USA).

Nearly all constructs showed a lower binding signal in presence of M13 peptide (FIG. 2; ratio higher than 1 corresponded to scFvs which showed a lower binding signal in presence of M13 peptide), while no signal changes were observed for the wildtype control (WT) ([G$_4$S]$_3$-linker) (SEQ ID NO: 137). The largest differences in signal intensities were observed around three regions of the calmodulin chain: close to the N-terminus or the C-terminus, and around amino acid 80. The two fusions from each of these three permutation regions with the largest binding difference (named N-1+2, M-1+2, C-1+2, respectively) as well as the non-permutated CaM variant (i.e. fused by its naive N/C-termini, named lin) were used for further analysis. These results confirmed that calmodulin inserted in the linker position between the V regions of antibody D1.3 can induce an M13 peptide-dependent influence on antigen binding. Insertion points are permissive at several different amino acid positions, but mainly clustered either around the position of the wildtype termini or the middle of the calmodulin polypeptide.

Example 3

Evaluation of M13 Peptide-Dependent Release Characteristics of Bound scFv-Fusions The calmodulin-mediated change of binding observed in the initial screening was achieved after preincubation with the modulator M13. Next, we designed a release ELISA to test whether M13 peptide binding to the calmodulin linkers can also induce the dissociation of an already established antibody-antigen complex. After an initial binding phase of scFv variants on antigen in calcium-containing buffer, M13 peptide was added, with calcium-only buffer used for control. In parallel, the same scFvs were analysed by the competitive preincubation approach described above (compare Example 2) on the same plate for calibration.

First, the scFv-CaM-constructs were produced in 500 mL shake flask scale. For protein expression, cells harboring the desired construct were grown overnight at 37° C. and 250 rpm in 30 mL 2×YP-GK-medium (2×YP-medium [16 g L$^{-1}$ soy peptone, 10 g L$^{-1}$ yeast extract, 5 g L$^{-1}$ NaCl, pH 7.0] containing 100 mM glucose and 50 µg/mL kanamycin). The next day, 500 mL fresh medium was inoculated to an OD$_{600}$ of 0.1 and shaken in 2 L shake flasks (37° C., 250 rpm) until an OD$_{600}$ of 1.0 was reached. Protein expression was induced with a final concentration of 0.2 mM IPTG and cultures were further incubated at 25° C. for 4 h. Bacteria were harvested by centrifugation (4000 g, 20 min, 4° C.) and the bacterial pellet was directly processed or stored at −20° C. until periplasmic extraction and protein purification.

For purification of the scFv-constructs, the bacterial pellet was resuspended in 10 mL TE-buffer per g pellet (100 mM Tris, 10 mM EDTA; pH 9.0 or pH 7.4, depending on the isoelectric point of the scFv-fusion) and incubated overnight at 37° C. at 250 rpm. The next day, Benzonase® Nuclease (final concentration: 1 U/mL; Merck, Darmstadt, Germany) and MgCl$_2$ (20 mM) were added for DNA clearance. Furthermore, Halt™ Protease Inhibitor Cocktail (Thermo Fisher Scientific, Dreieich, Germany) was added to prevent degradation of the target protein. The mixture was incubated for 1 h at 37° C. and 250 rpm. Afterwards, the protein containing supernatant was separated from the cell debris by centrifugation (5000 g, 20 min, RT) and prepared for purification by addition of 11× dilution buffer (110 mM Tris, 550 mM NaCl, 55 mM Imidazol; pH 9.0 or pH 7.4). 250 μL Nickel Sepharose™ 6 resin (GE Healthcare, Solingen, Germany) was equilibrated with 10 column volumes (CV) washing buffer 1 (50 mM $NaH_2PO_4$, 50 mM NaCl, 5 mM Imidazol; pH 9.0 or pH 7.4) on Poly-Prep® Chromatography Columns (Bio-Rad, Munich, Germany) and afterwards loaded with the periplasmic supernatant, followed by washing with 30 CV washing buffer 1 and 15 CV washing buffer 2 (50 mM $NaH_2PO_4$, 50 mM NaCl, 25 mM Imidazol; pH 9.0 or pH 7.4). The protein was eluted with 5 CV elution buffer 1 (50 mM $NaH_2PO_4$, 50 mM NaCl, 150 mM Imidazol; pH 9.0 or pH 7.4) and 5 CV elution buffer 2 (50 mM $NaH_2PO_4$, 50 mM NaCl, 350 mM Imidazol; pH 9.0 or pH 7.4). Target protein containing fractions were pooled and dialyzed at 4° C. against 200 volumes of 1× tris-buffered saline (TBS) (50 mM Tris, 150 mM NaCl; pH 8.0) for 2 h, followed by another dialysis against fresh buffer (200 volumes) for 2 h. The final dialysis was performed overnight at 4° C. against 500 volumes of buffer. Protein concentration was determined with the Pierce™ Coomassie Protein Assay Kit (Thermo Fisher Scientific, Dreieich, Germany) according to the manufacturer's instructions and afterwards used for competitive and release ELISA.

The competitive ELISA was performed as described in Example 2. The release ELISA differed from the competitive ELISA only in the preincubation step and an additional release step was performed to evaluate whether already bound antibody fragments dissociate from the antigen in presence of M13 peptide. Purified scFvs for both setups (setup A and setup B) were diluted to appropriate concentrations (0.1 μM) in 1×B-TBS/5 mM $CaCl_2$ and directly transferred (i.e. without preincubation step in polypropylene plates) to the blocked ELISA plates. After initial binding of the scFvs (1.5 h, RT), plates were washed (three times with 1×TBST) and different release-buffers were added. For the control (setup A), wells were filled with 100 μL 1×B-TBS/5 mM $CaCl_2$, whereas 1×B-TBS/5 mM $CaCl_2$/1 μM M13 peptide was added in setup B. After incubation for 1 h at RT, plates were treated comparable to the competitive ELISA.

Figure 3A:
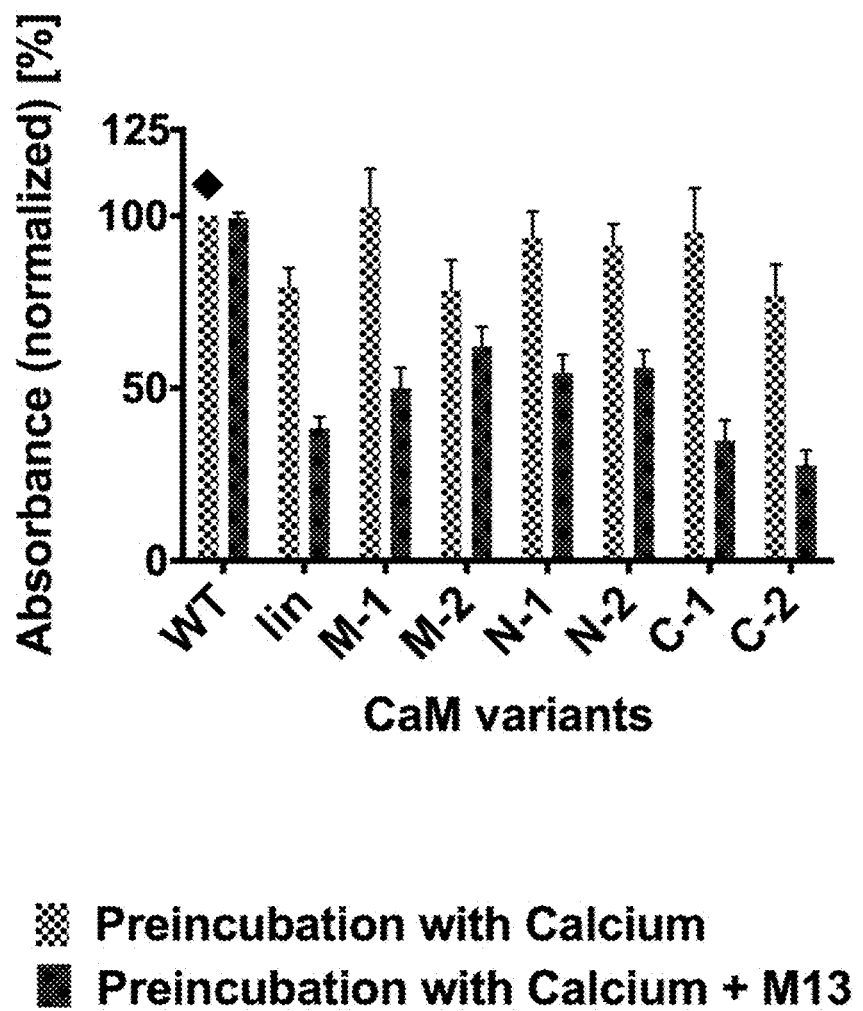
FIGS. 3A and 3B: Analysis of M13 peptide dependent binding behavior of anti-lysozyme scFv-Calmodulin-variants by competitive ELISA (FIG. 3A) and release ELISA (FIG. 3B).
Figure 3B:
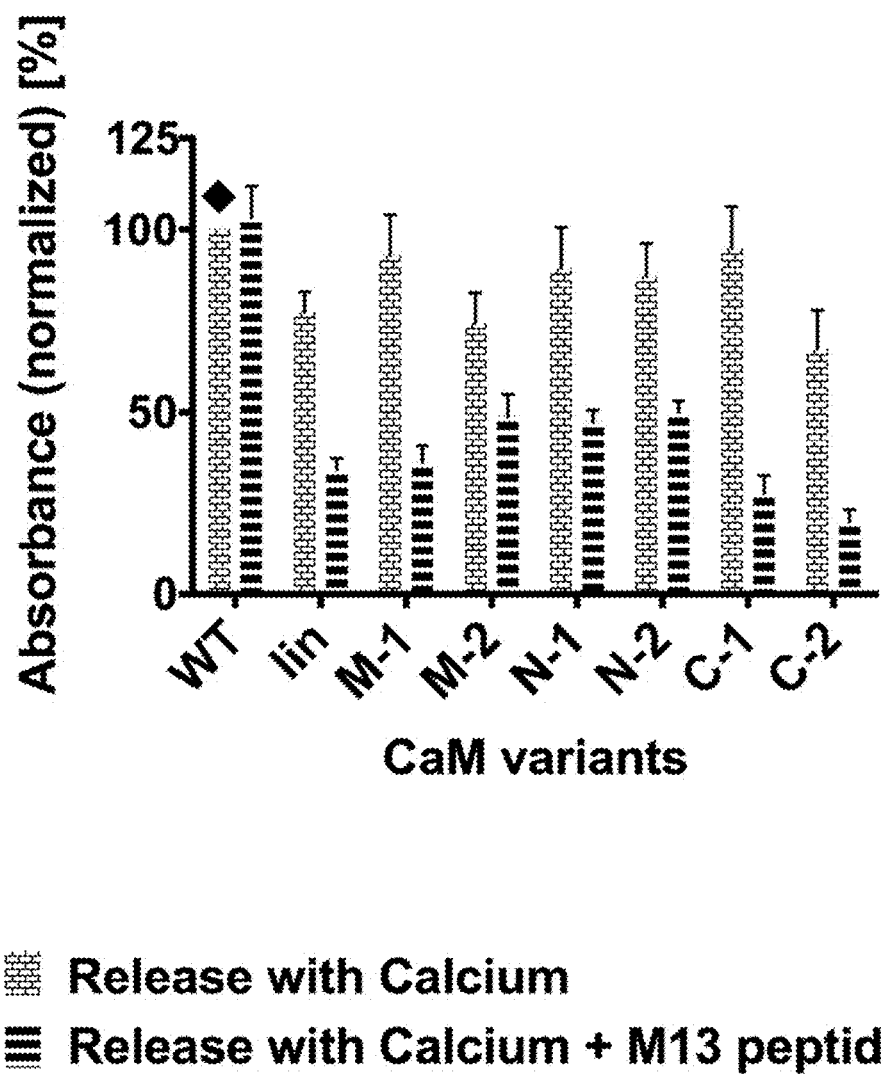

Absorbance was measured and normalized, where the signal obtained for the wildtype control (indicated by black rhombus) in calcium-containing buffer was set to 100%. The median results of four experiments (n=4) are shown in FIGS. 3A and 3B, where the error bars indicate the standard deviation. The drop of affinity in the presence of peptide in the release-setup (FIG. 3B) was comparable to the drop observed in the preincubation approach (FIG. 3A). The highest decrease in signal was observed for the variants with CaM-linkers permutated C-terminally (C-1, C-2) and the M-1 variant. Therefore, the use of these permutated CaM-variants was advantageous over the linear (i.e. not permutated) CaM-linker. Taken together, these results indicated that a specific release of scFv-CaM-fusion from its antigen was achieved by adding M13 peptide, indicating a loss of binding.

Example 4

Evaluation of the Specific M13 Peptide Dependent Binding Behaviour of Anti-Lysozyme scFv-CaM-Fusions To evaluate whether the modulation of binding of the D1.3 scFv-CaM-variants is specific, the binding of a defined amount of scFv (0.1 μM) as a function of increasing concentrations of M13 peptide in presence of calcium was determined. A control titration was performed in EDTA-containing buffer to assess any calcium-independent effect of M13 peptide.

The production and purification of different scFv-fusions was performed as described in Example 3. The titration ELISA differed from the competitive ELISA (described in Example 2) only in the buffer composition used for preincubation. From column 11 to 2, M13 peptide concentration was sequentially diluted (dilution factor: 1:2) in 1×TBS/5 mM $CaCl_2$ (highest concentration in column 11: 3.2 μM; lowest concentration in column 2: 6.25 nM; control in column 1: 0 nM). For the evaluation if the interaction between calmodulin and M13 peptide is dependent on calcium, the titration was additionally performed in 1×B-TBS/5 mM EDTA.

Figure 4A:
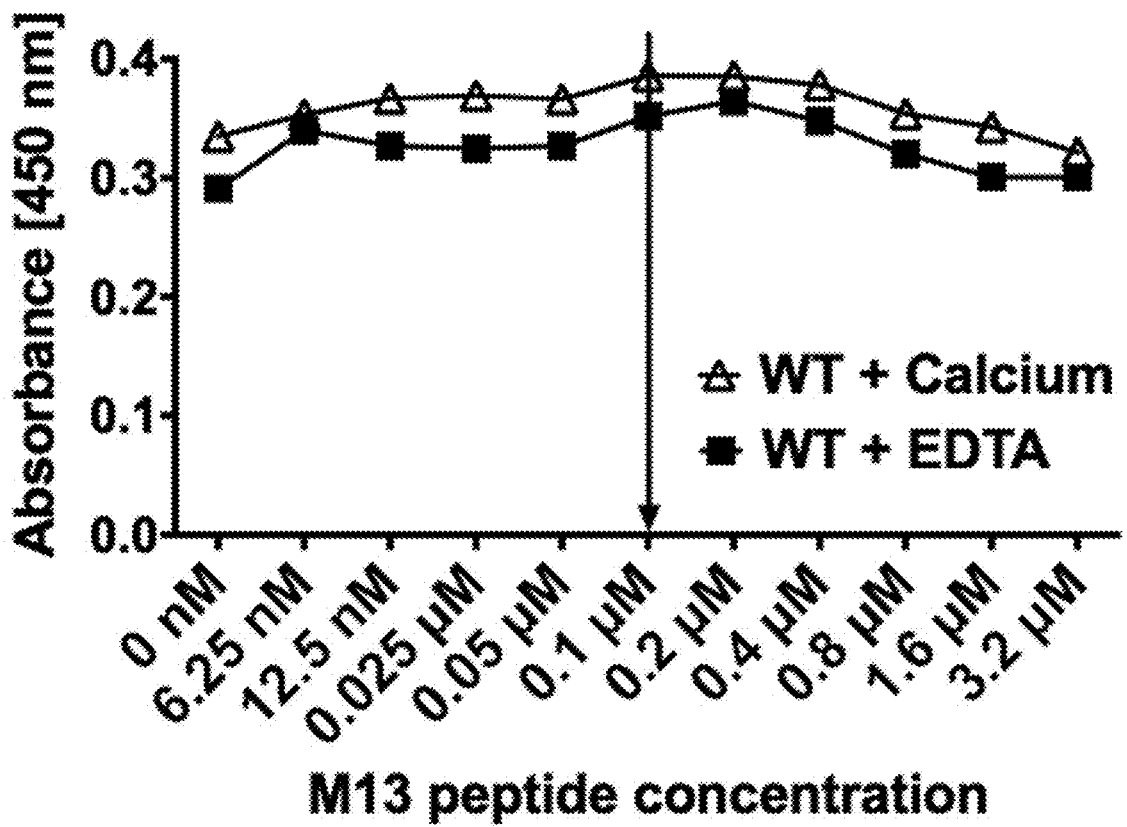
FIGS. 4A-4H: Evaluation of the specific M13 peptide dependent decrease of binding signal by titration ELISA (FIG. 4A, FIG. 4B, FIG. 4C, FIG. 4D, FIG. 4E, FIG. 4F, FIG. 4G, FIG. 4H).
Figure 4B:
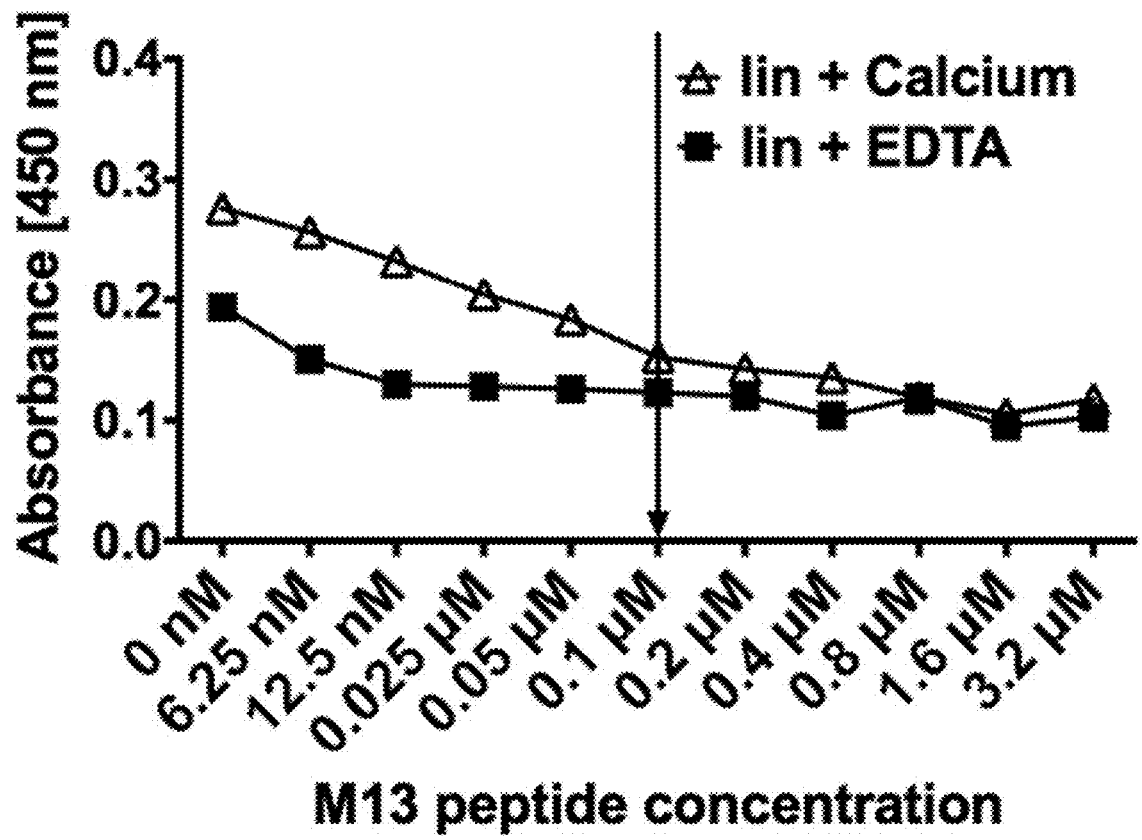
Figure 4C:
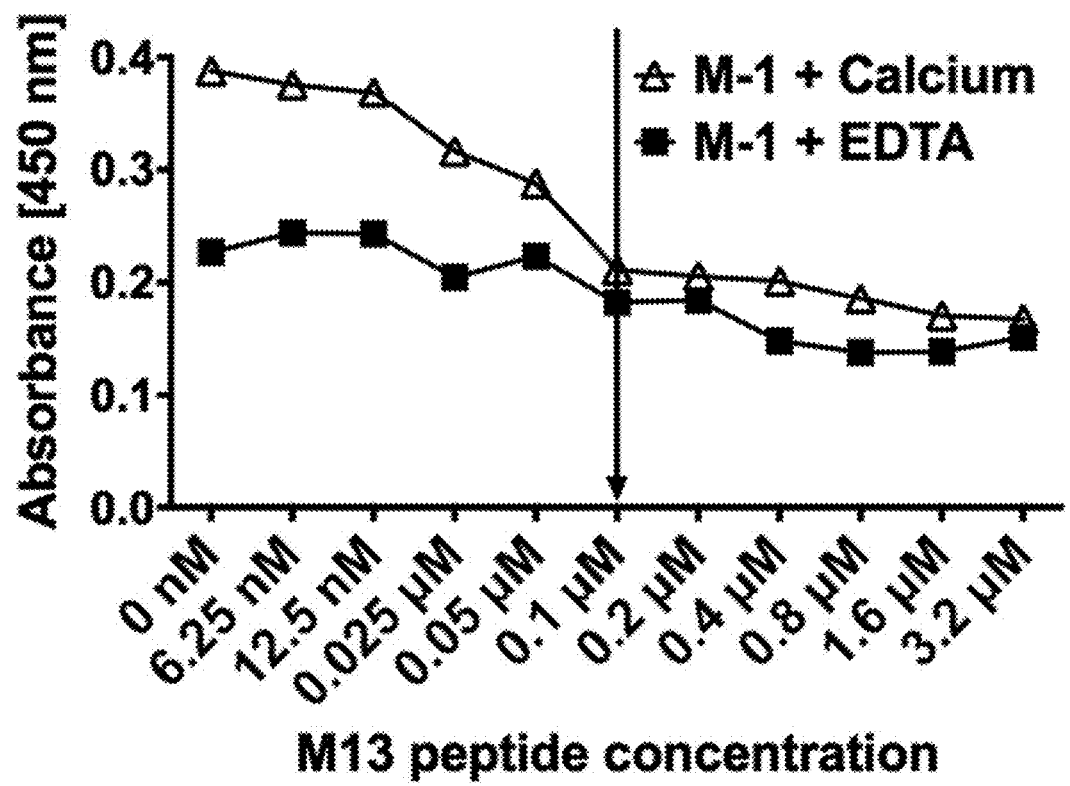
Figure 4D:
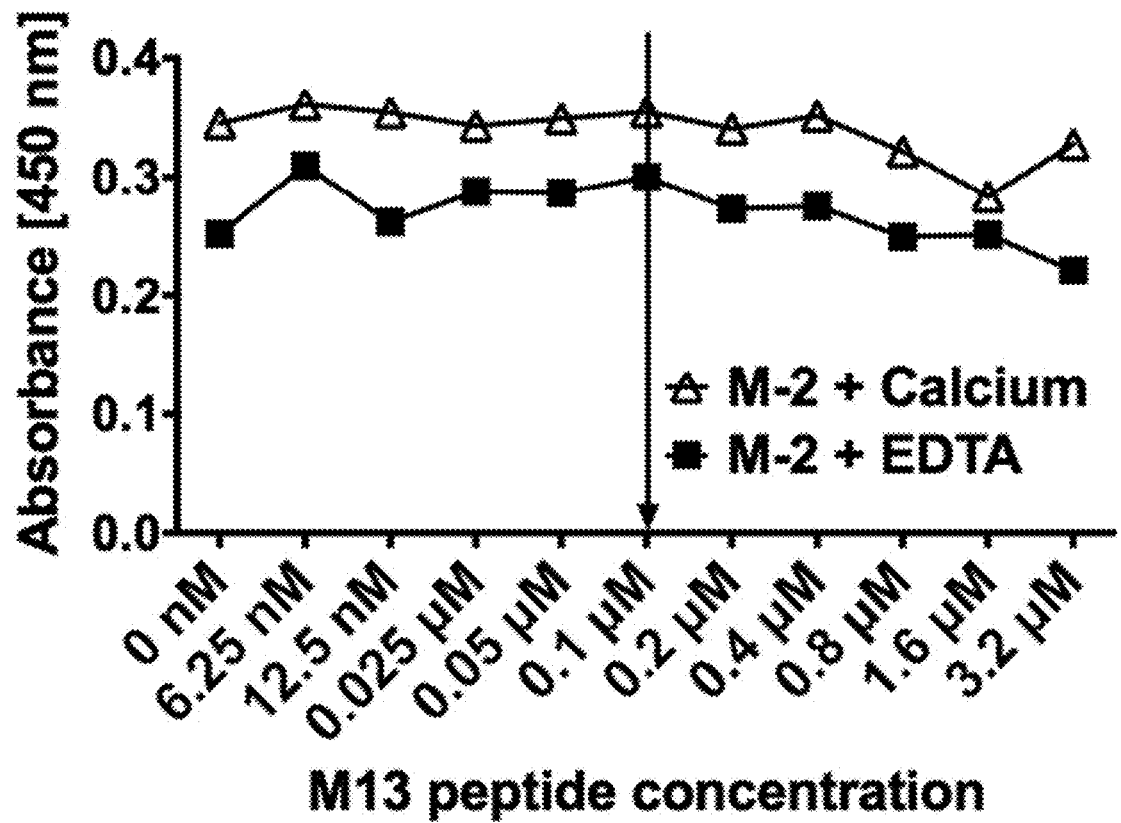
Figure 4E:
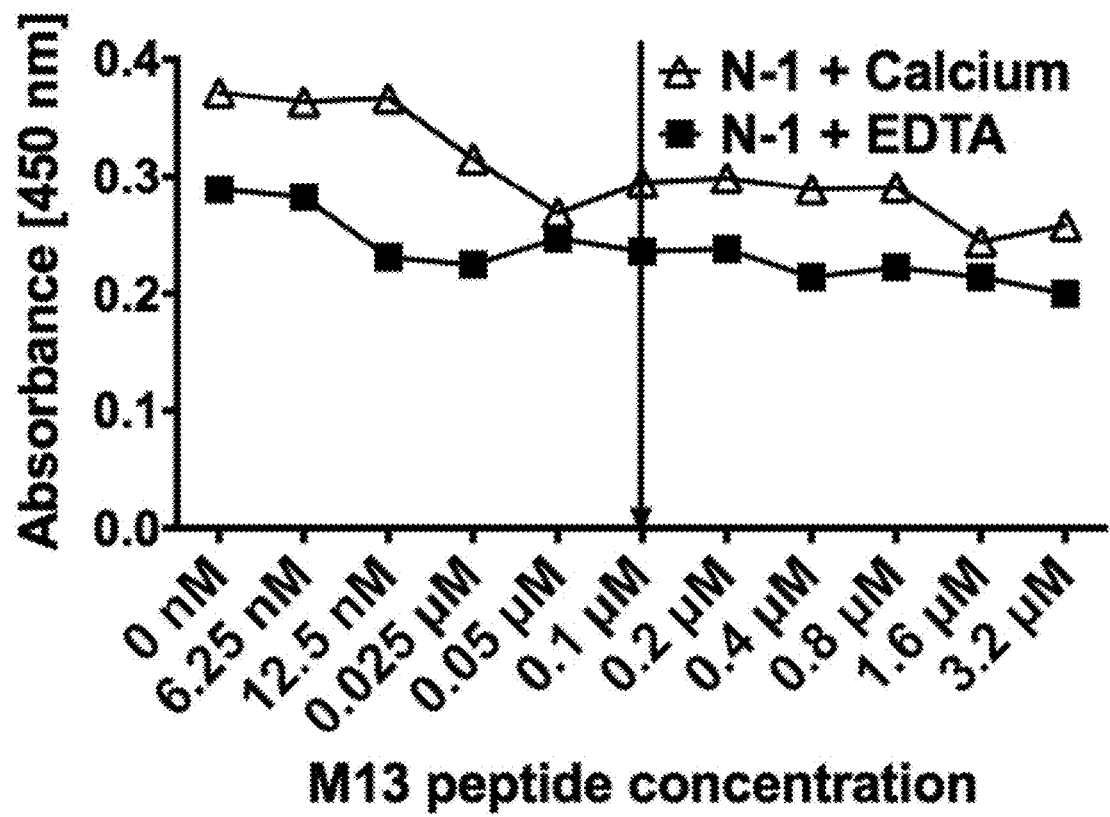
Figure 4F:
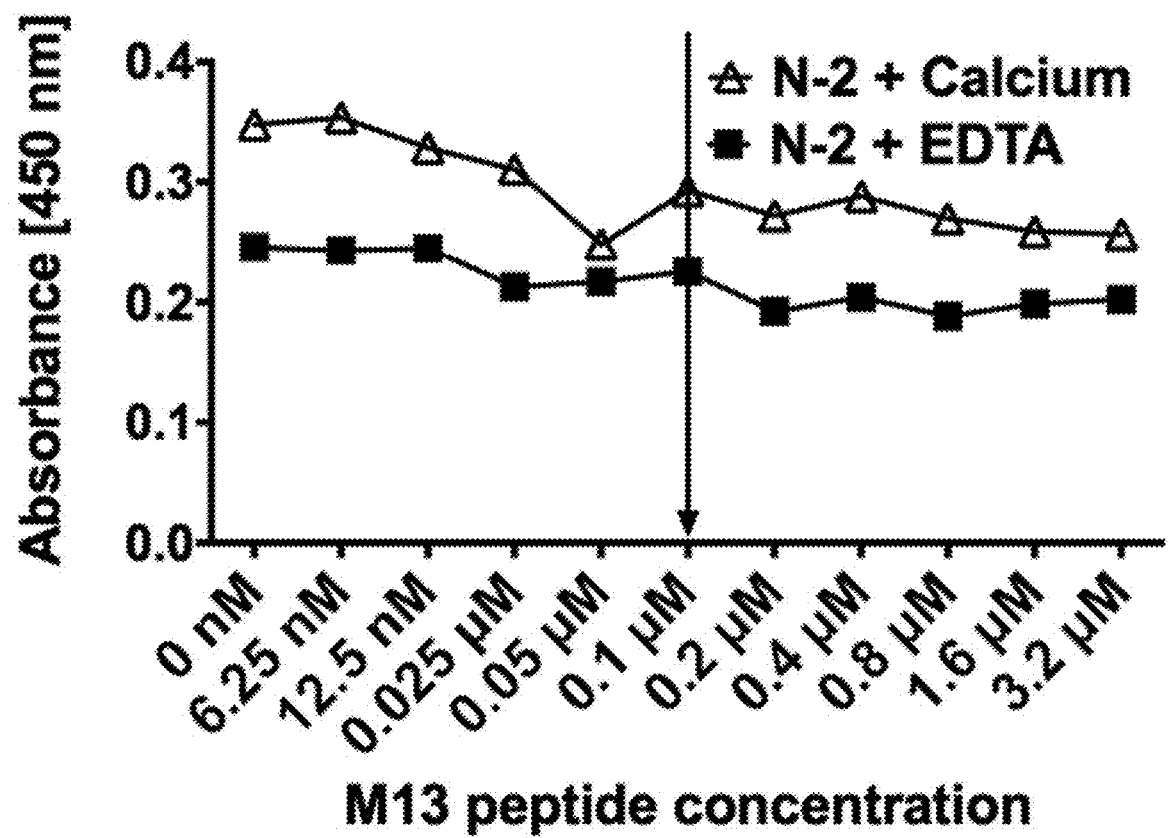
Figure 4G:
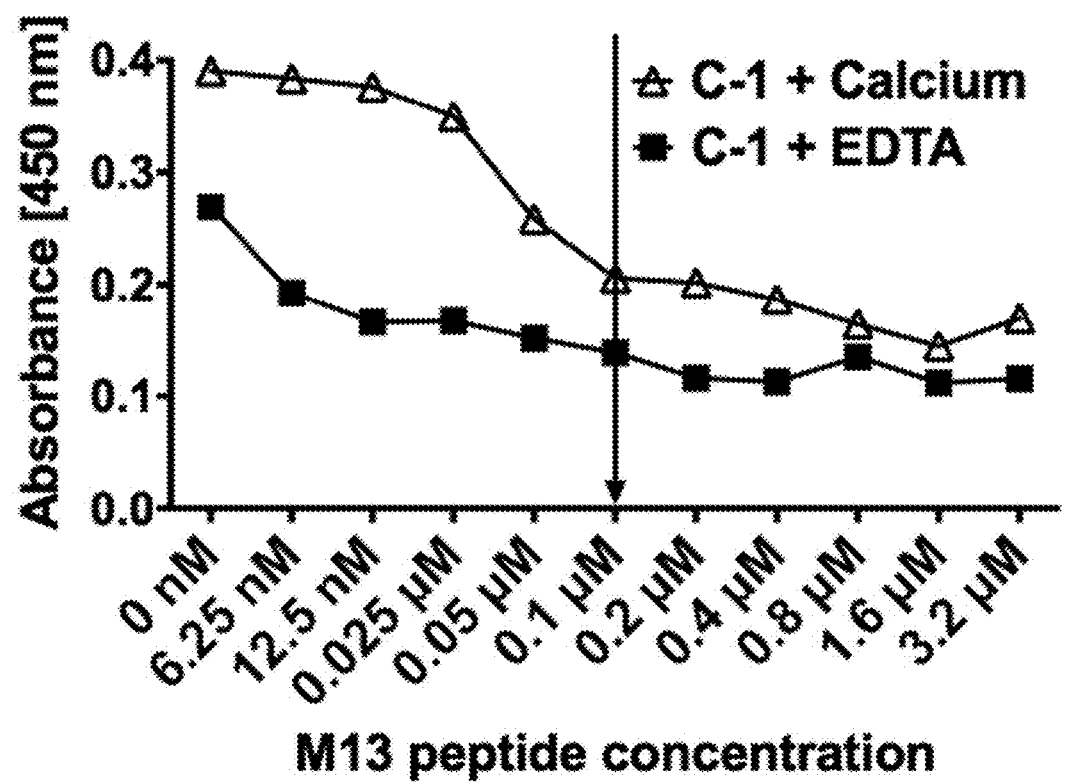
Figure 4H:
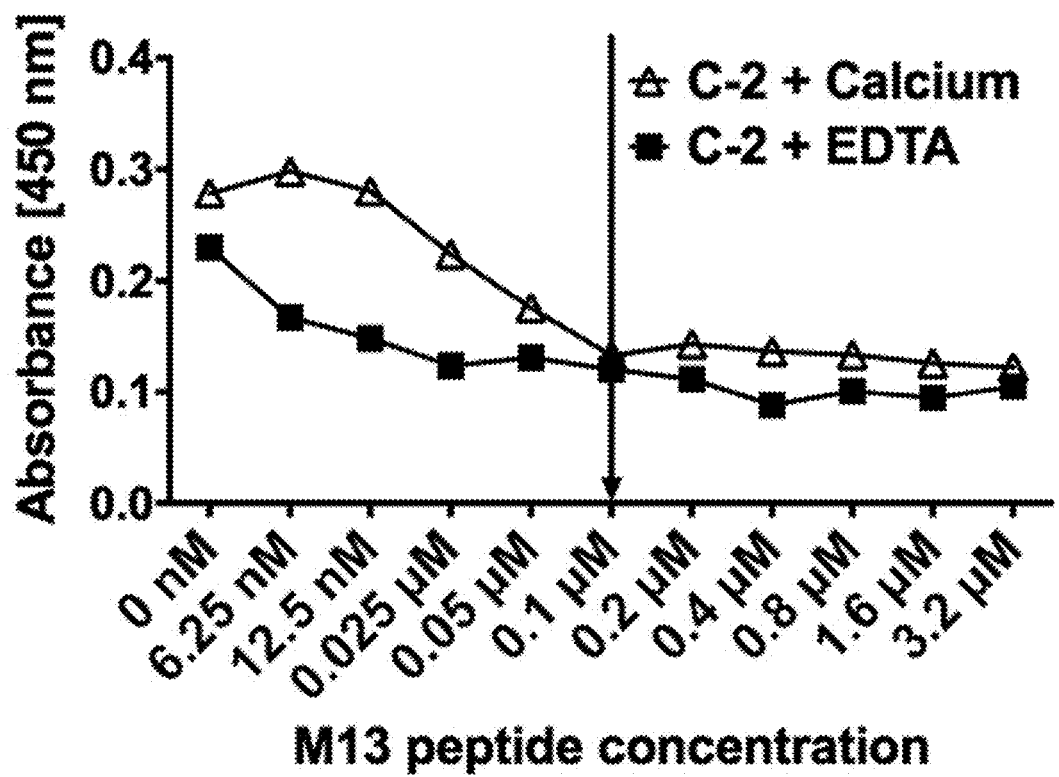

Nearly all analysed scFv-CaM-variants showed a calcium-dependent decrease in antigen binding with increasing peptide-concentration. At a concentration of 0.1 μM M13 peptide, a molar ratio of 1:1 (indicated by arrows), no further loss of binding signal was observed (FIG. 4B, FIG. 4C, FIG. 4E, FIG. 4F, FIG. 4G, FIG. 4H, empty triangles). Only the M-2 variant did not show this tendency (FIG. 4D) and behaved similar to the wildtype control (FIG. 4A). The C-terminally permutated (FIG. 4G, FIG. 4H) and the M-1 variant (FIG. 4C) provided the strongest dissociation, corroborating the results shown in FIG. 3. In the EDTA-controls, increasing M13 peptide concentrations did not have an influence on the absorbance measured (FIG. 4A, FIG. 4B, FIG. 4C, FIG. 4D, FIG. 4E, FIG. 4F, FIG. 4G, FIG. 4H, filled squares). However, overall antigen/scFv-CaM binding was clearly affected by the presence of EDTA, as binding signals obtained in the EDTA-setup were much lower than the corresponding ones with calcium.

In summary, six out of seven tested scFv-CaM-fusions showed M13 peptide-dependent antigen binding, with a maximum loss of binding at a 1:1 molar ratio of M13 peptide:scFv.

Example 5: Function of CaM-Linker Activity in Other scFv-Antibodies

To investigate whether the linkers identified to provide modulation of binding in scFv D1.3 can be used as a "universal" module to change binding properties in other scFv fragments than D1.3, the characterized CaM-linker variants were cloned into other scFv antibodies with different specificities. The specificities were chosen according to their utility in future cell staining and separation applications, with two scFvs directed against different human clusters of differentiation (CD14, CD4) and the small hapten biotin. To identify M13 peptide-dependent scFv-CaM-variants for those specificities, human blood cells (PBMC) were stained using purified scFvs and subsequently analysed by flow cytometry. Bound scFvs were detected with fluorescently labeled anti-His-antibodies. Incubation protocols for flow cytometric analysis were comparable to the pre-incubation ELISA, with buffers including and without M13 peptide.

The production and purification of different scFv-fusions was performed as described in Example 3. All antibodies and staining reagents used for flow cytometry applications were from Miltenyi Biotec (Bergisch Gladbach, Germany). For stainings with anti-Biotin scFv-variants, PBMC (peripheral blood mononuclear cells) were prestained with appropriate IgG-conjugates. The stainings were performed in 1.5 mL microtubes. 1×10⁶ PBMC per sample were incubated on ice for 10 min in 110 µL 1×B-TBS (1×TBS+0.5% [w/v] bovine serum albumin)+5 mM CaCl$_2$ (pH 7.4) containing anti-CD14-Biotin (dilution: 1:11). The reaction was stopped by addition of 1 mL buffer and centrifugation at 300 g for 5 min at 4° C. The supernatant was removed completely and the pellet was stored on ice and resuspended in buffer immediately before the next staining step. The following stainings were performed in 96-well polypropylene plates. Purified scFvs were diluted to appropriate concentrations in 50 µL 1×B-TBS/5 mM CaCl$_2$ (pH 7.4 [anti-Biotin] or pH 8.0 [anti-CD14, anti-CD4]) per well. For competitive screenings, peptide (M13 peptide [Anaspec, Fremont, USA], M13-variants library and CBP (calmodulin-binding peptide) library [Genscript, Piscataway, USA]) was added in molar excess in a total volume of 5 µL per well, whereas the control stainings were supplied with 5 µL 1×B-TBS/5 mM CaCl$_2$. The diluted scFvs were preincubated for 45 min at RT and afterwards chilled on ice for 5 min. After addition of 2×10⁵ cells (in 45 µL 1×B-TBS/5 mM CaCl$_2$) and incubation for 20 min on ice, the wells were filled with buffer up to a volume of 285 µL and centrifuged at 300 g for 10 min at 4° C. Subsequently, the cells were resuspended in 110 µL 1×B-TBS/5 mM CaCl$_2$ containing anti-His-PE (phycoerythrin) (dilution: 1:11), incubated on ice for 10 min, followed by a further washing step and finally resuspended in 200 µL buffer. The analysis was performed on a MACSQuant® Analyzer 10 in chill 96 rack mode with automated addition of propidium iodide solution for exclusion of dead cells (final concentration: 1 µg/mL). A total of 10,000 events were collected for each sample.

Figure 5A:
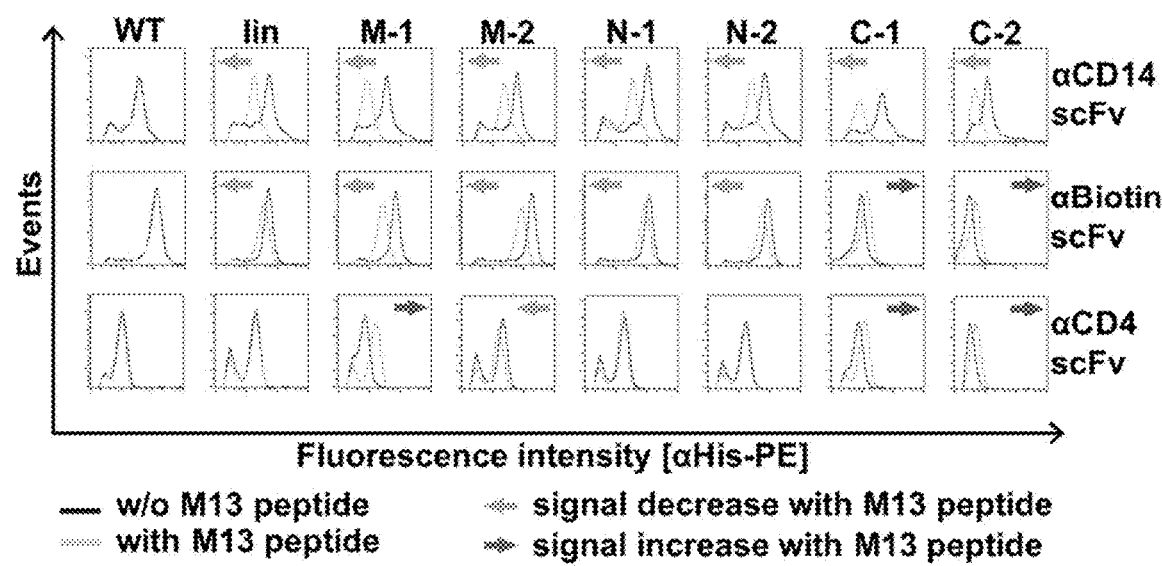
FIGS. 5A-5D: Identification of switchable anti-CD14, anti-Biotin and anti-CD4 scFv-Calmodulin-fusions by competitive staining of PBMC and analysis by flow cytometry (FIG. 5A). Comparison of the extent of binding modulating properties of different Calmodulin-linker variants in anti-CD14 scFv (FIG. 5B), anti-Biotin scFv (FIG. 5C) and anti-CD4 scFv (FIG. 5D).

The highest M13 peptide dependent decrease in fluorescence intensity was obtained for the anti-CD14 scFv-CaM-variants (FIG. 5A, first row). In case of anti-Biotin scFvs (FIG. 5A, second row), two linker-variants (M-1, M-2) resulted in a high peptide-dependent decrease of the binding signal, although a slight decrease was observed for the remaining clones as well (lin, N-1, N-2). Interestingly, the C-terminally permutated variants (C-1, C-2) led to the opposite switching behaviour with an increase in fluorescence intensities. The same trend was monitored for three anti-CD4 scFvs (M-1, C-1, C-2), showing an even higher signal increase than anti-Biotin scFv-variants (FIG. 5A, third row) upon M13 peptide incubation.

Figure 5B:
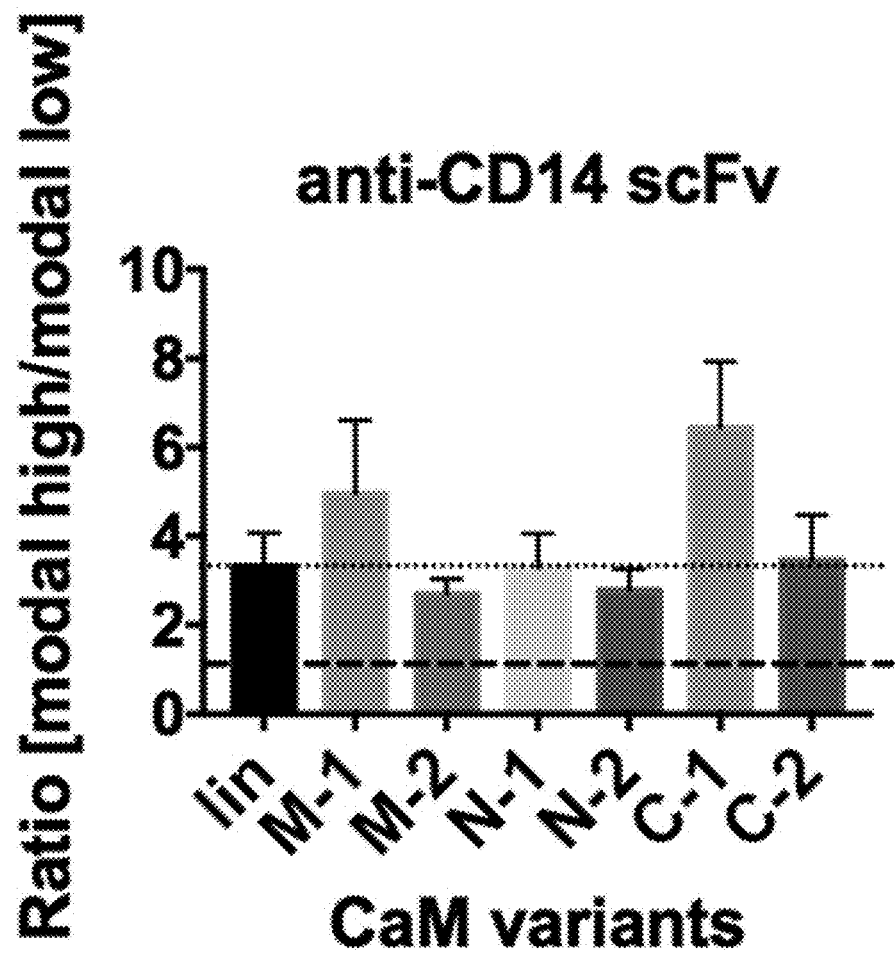
Figure 5C:
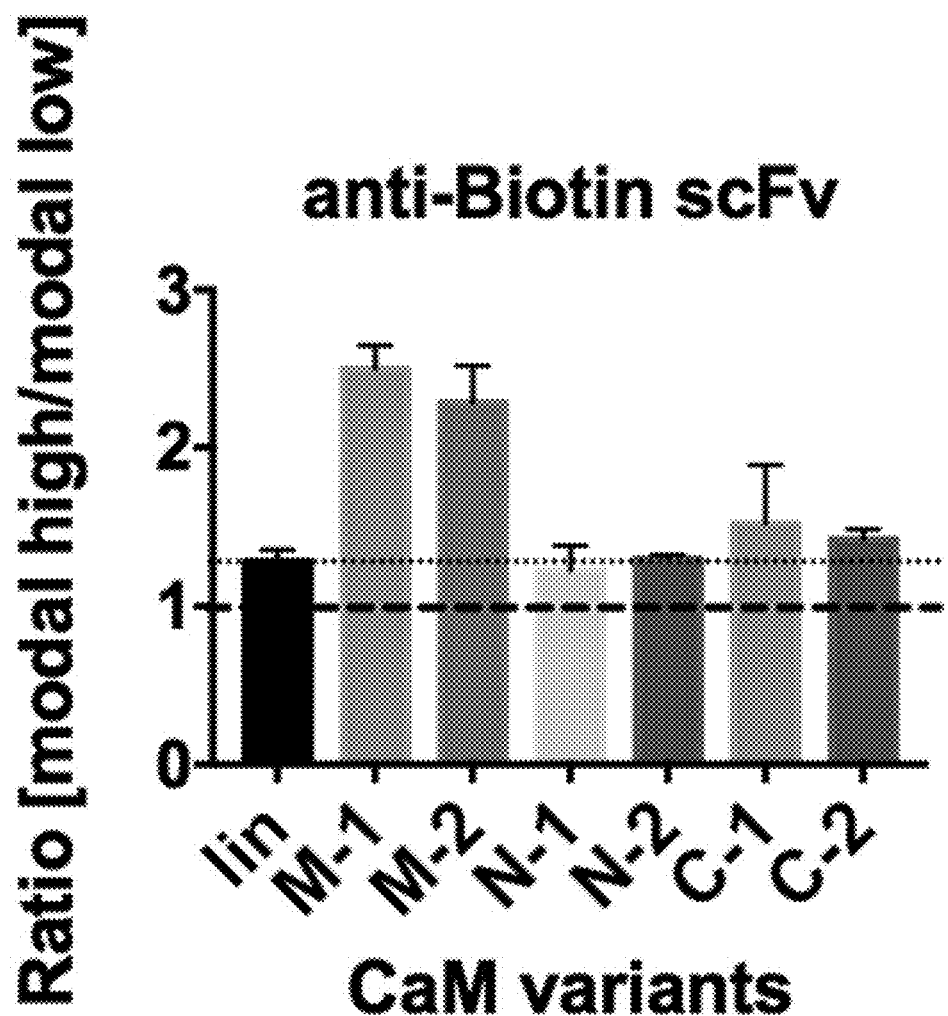
Figure 5D:
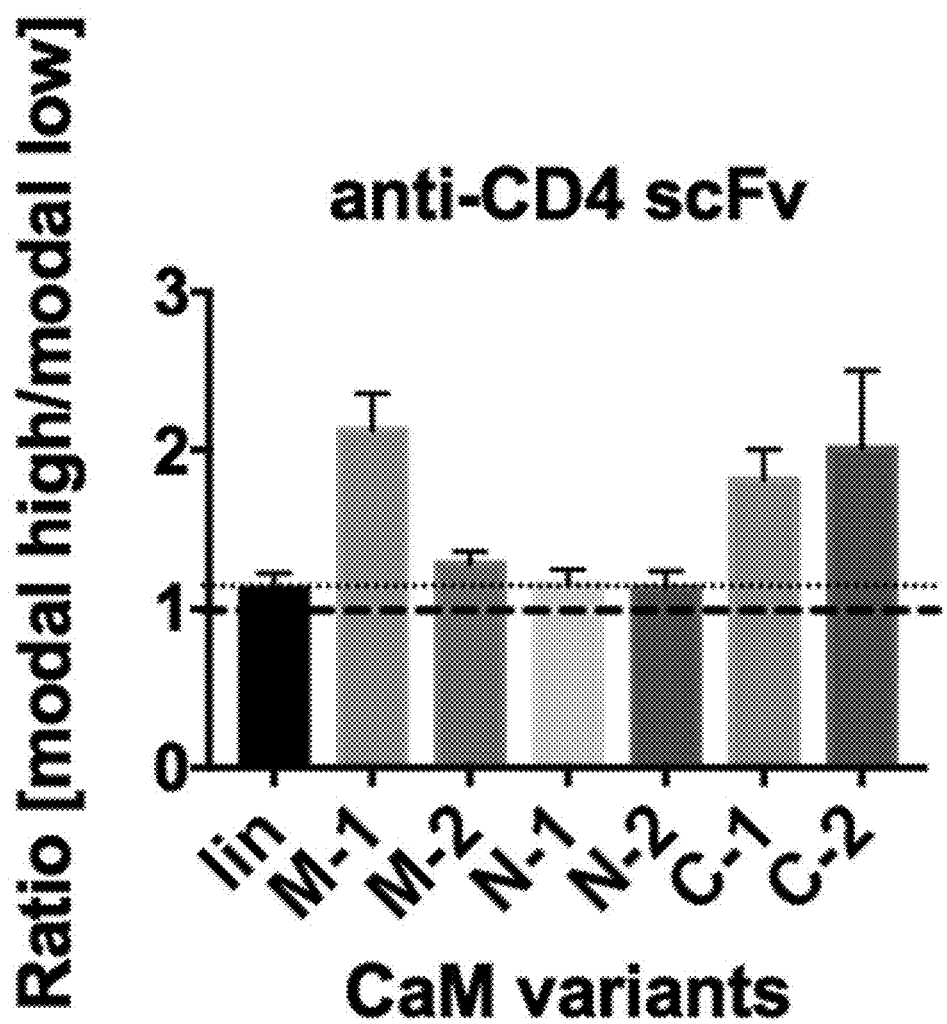

FIG. 5B, FIG. 5C and FIG. 5D show the ratio of the high binding signals in comparison to the low binding signals. The high modal fluorescence intensities were divided by the low modal fluorescence intensities. A ratio of 1 (indicated by broken line) corresponded to a non-switchable antibody. These figures show, that the use of permutated CaM-variants resulted in a highly switchable antibody in all specificities. In contrast to that, the linear variant provided only one highly switchable antibody fragment (anti-CD14 scFv) (FIG. 5B), since the generated anti-Biotin scFv (FIG. 5C) only showed a slight decrease in binding signal and the anti-CD4 scFv showed no change at all (FIG. 5D). All in all, the use of permutated calmodulin-linkers, preferably of C-terminally permutated variants or those permutated in the middle of the former calmodulin encoding gene, led to a higher change in binding signal than the linear calmodulin-linker. Moreover, two further specificities were analysed according to their switching behaviour, anti-CD20 scFv-CaM-fusions and anti-FITC (fluorescein isothiocyanate) scFv-CaM-variants. For the anti-CD20 scFvs, a slight peptide-dependent decrease of binding signal was observed for all CaM-variants, whereas none of the tested anti-FITC scFv-CaM-variants showed a switching in binding behaviour (data not shown). In summary, we have shown that the mechanism of modulation of binding through a calmodulin-linker/M13 peptide combination could be transferred to four of the tested five antibody specificities. Furthermore, the use of permutated CaM-linkers was advantageous over the linear CaM-variant.

Example 6

Figure 6A:
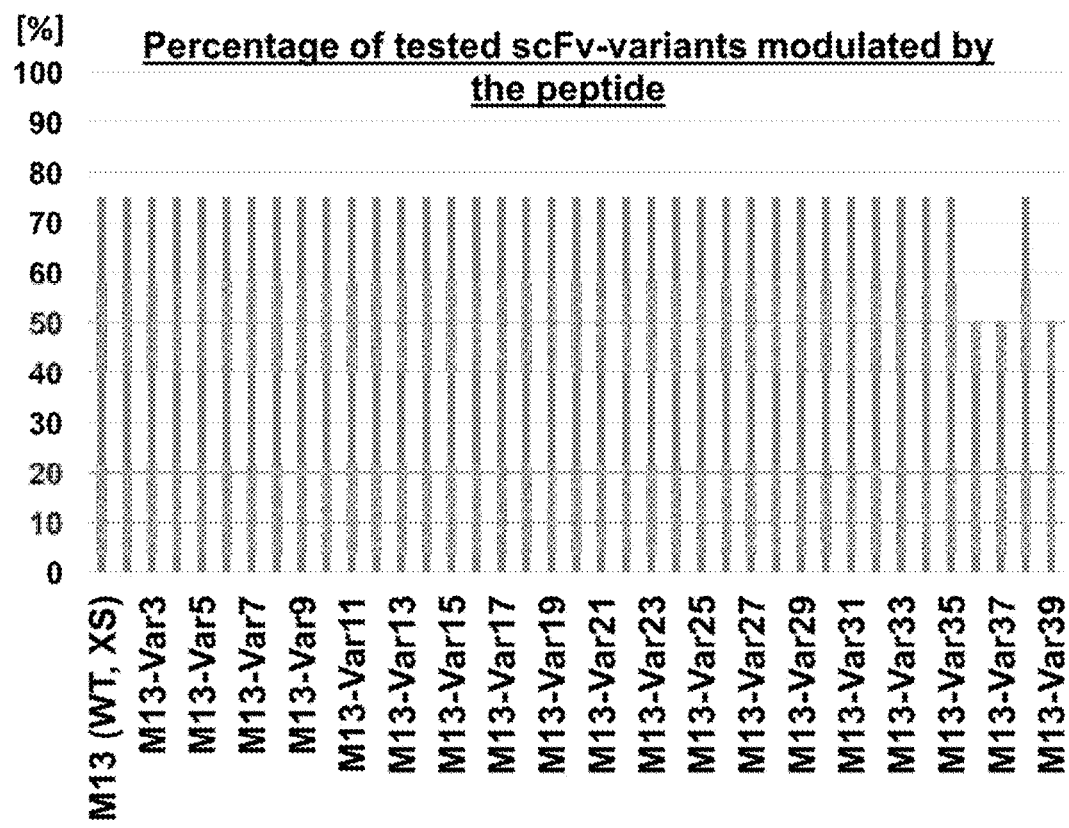
FIGS. 6A and 6B: Overview of further calmodulin-binding peptides with binding modulating properties (FIG. 6A, FIG. 6B).
Figure 6B:
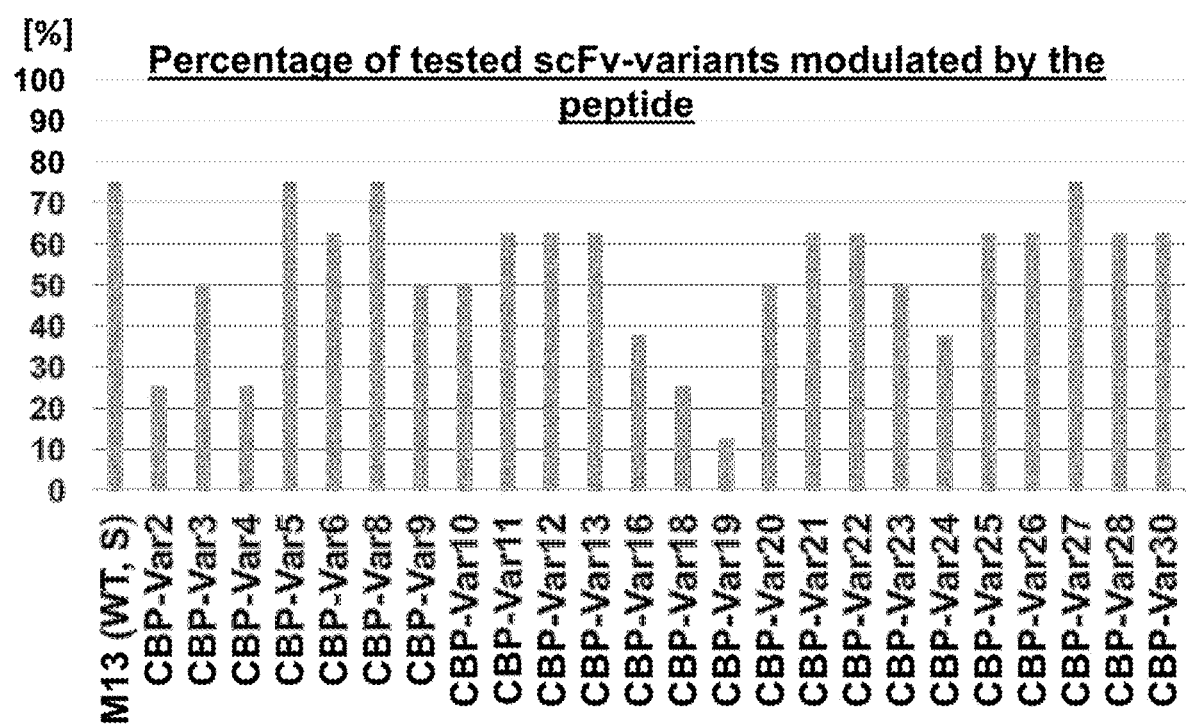
Figure 7A:
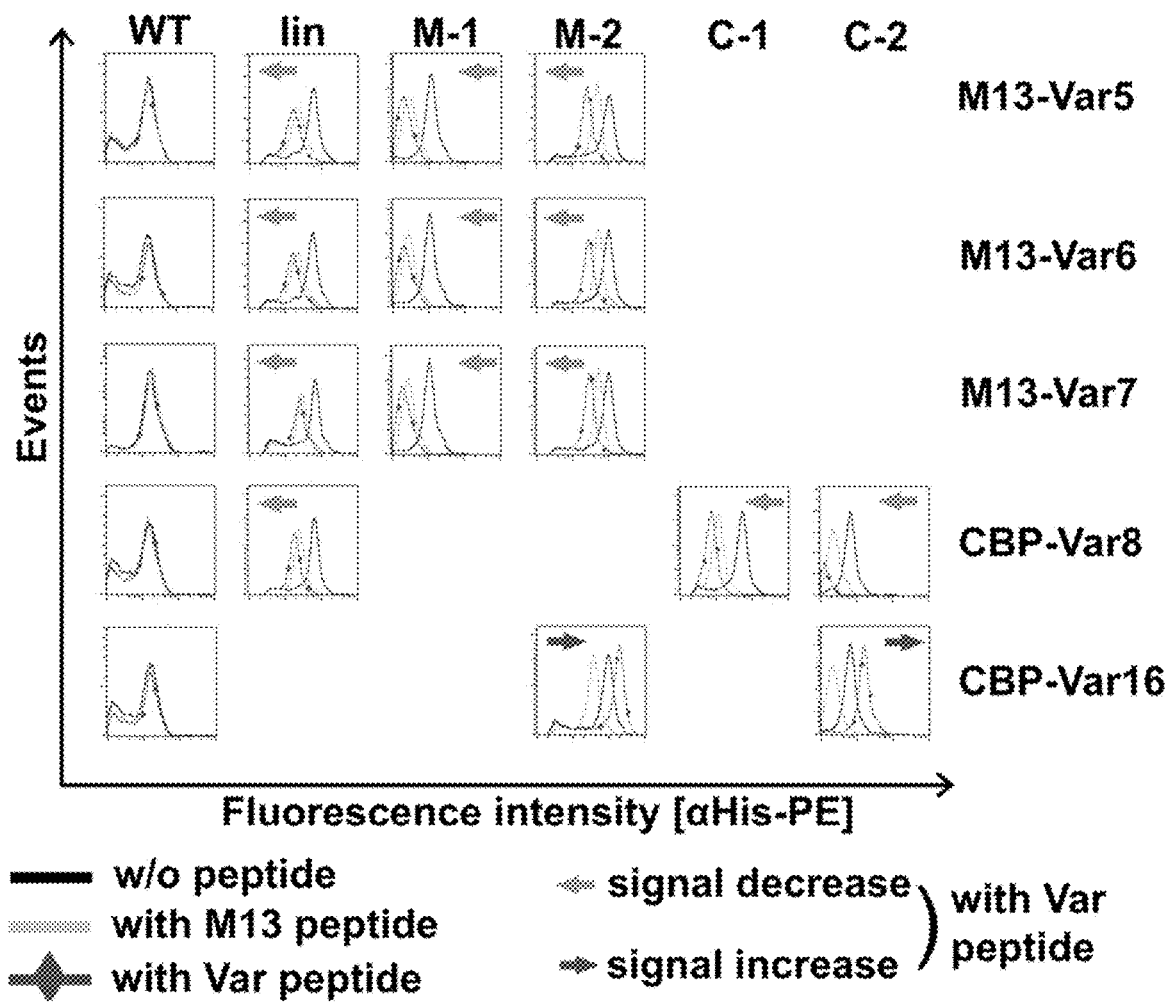
FIGS. 7A-7C: Identification of further calmodulin-binding peptides with binding modulating properties—most promising peptides (FIG. 7A, FIG. 7B, FIG. 7C).
Figure 7B:
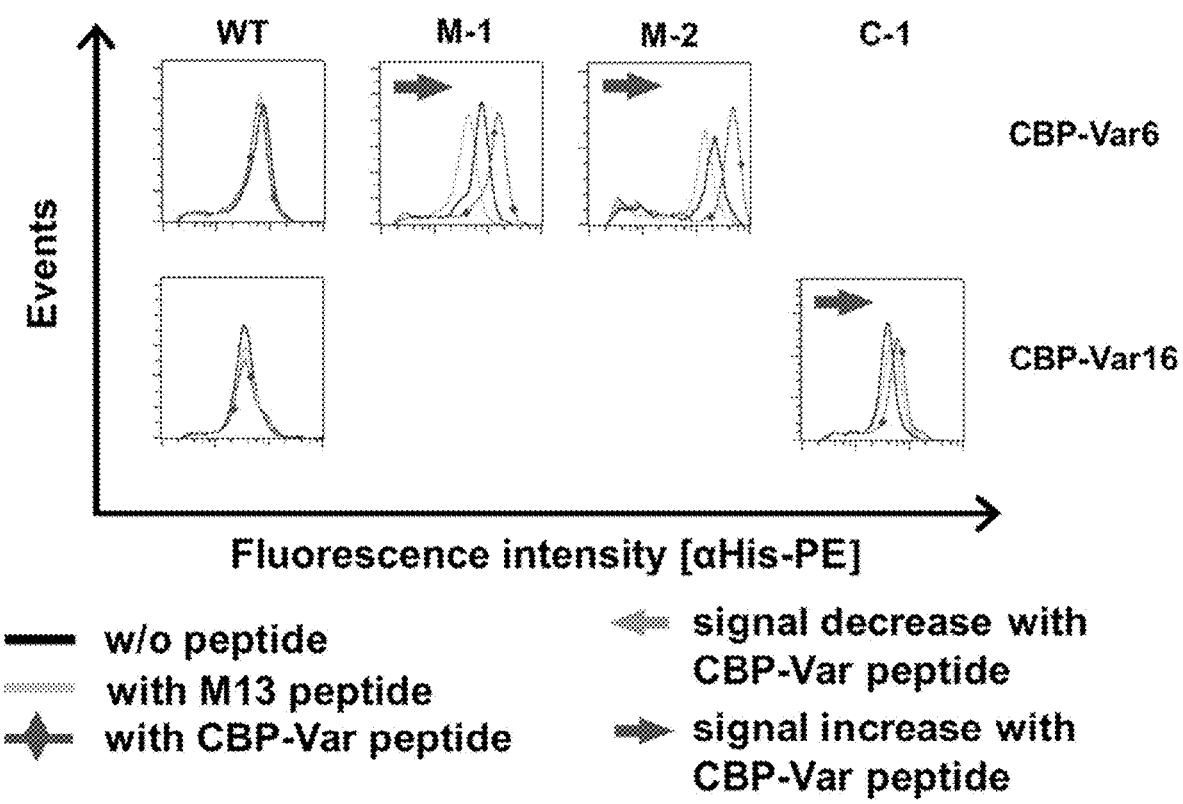
Figure 7C:
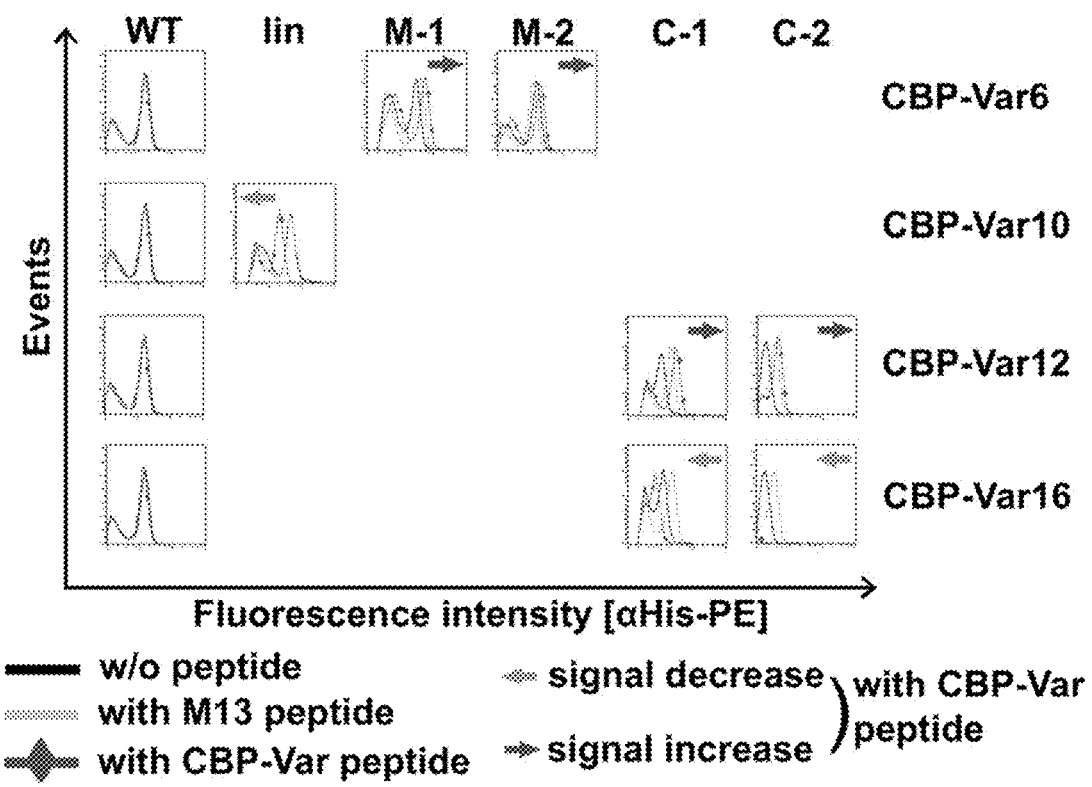

Identification of Further Calmodulin-Binding Peptides with Binding Modulating Properties Calmodulin binds to a variety of binding partners. To investigate if further calmodulin-binding peptides or mutants derived from M13 are able to modulate the binding properties of the scFv-CaM-fusions, a peptide screening was done. On the one hand, 38 mutated variants of the M13 peptide were analysed, e.g. substitution mutants known to have higher affinities for calmodulin, truncated variants and combinations thereof. In addition, 29 peptides derived from further calmodulin-binding proteins like calcium ATPase, spectrin and nitric oxidase synthase were analysed with regard to potential binding modulating properties. The analysis was performed via competitive staining of PBMC as in the previous experiments described in Example 5. The complete screening (i.e. of the whole peptide libraries) was performed with 4 different linker variants of anti-CD14 scFv (lin, M-2, N-1, C-1) and anti-CD4 scFv (lin, M-1, N-1, C-1). The wildtype of each specificity was used as a control. All 38 mutated variants of the M13 peptide showed affinity modulating properties, whereas 24 of 29 analysed peptides derived from alternative calmodulin-binding proteins resulted in a change in binding signal in at least one analysed scFv-CaM-fusion (FIG. 6A (variants of M13 peptide) and FIG. 6B (calmodulin-binding peptides); only peptides which modulated at least one scFv-variant are included in the figure). Most of the tested peptides showed an effect comparable to the M13 peptide or a slightly less influence. We focused on the peptide variants, which led to an even higher signal decrease or increase than M13 and analysed all scFv-CaM-fusions of anti-CD14, anti-Biotin and anti-CD4 scFv (FIG. 7A, FIG. 7B, FIG. 7C). For anti-CD14 scFv, three different variants of the known high affinity mutant of M13 resulted in a higher signal decrease in the clones permutated in the middle of CaM and the linear clone (FIG. 7A, M13-Var5/6/7). CBP-Var8, a derivative of spectrin, led to a slightly higher decrease in the C-terminally permutated and the linear variant (FIG. 7A, CBP-Var8). Unexpectedly, a peptide derived from calcium-transporting ATPase (CBP-Var16) resulted in an increase in fluorescence signal in the M-2 and C-2 variants (FIG. 7A, CBP-Var16). The same opposite behaviour was monitored for the C-terminally permutated clones of anti-CD4 scFv, where M13 peptide led to an increase in binding signal, while CBP-Var16 resulted in an unexpected decrease in fluorescence intensity (FIG. 7C, CBP-Var16). Two anti-Biotin scFv-CaM-fusions (M-1, M-2) showed such an opposite switching behaviour in presence of CBP-Var6, another derivative of calcium-transporting ATPase (FIG. 7B, CBP-Var6). Surprisingly, CBP-Var16 had a further increasing effect on the C-1 clone and showed no opposite switching behaviour as in the other scFv-CaM-fusions (FIG. 7B, CBP-Var16). The same was observed for the anti-CD4 scFv M-variants, where CBP-Var6 led to a further increase in fluorescence intensity (FIG. 7C, CBP-Var6). Furthermore, a peptide derived from endothelial nitric oxidase synthase (CBP-Var12) had the same effect on the C-terminally permutated anti-CD4 scFv-CaM-fusions (FIG. 7C, CBP-Var12). Another unexpected decrease in binding signal was observed for the linear anti-CD4 scFv clone, triggered by CBP-Var10, derived from ionotropic glutamate receptor NMDA1, although the M13 peptide did not have any influence at all (FIG. 7C, CBP-Var10).

In summary, we have shown that the majority of the tested calmodulin-binding peptides led to a modulation of binding in the scFv-CaM-fusions. Some candidates were identified which resulted in an even higher decrease or increase of binding signal than the wildtype variant of M13. Furthermore, some peptides resulted in an unexpected opposite switching behaviour.

The invention claimed is:

1. A composition comprising
   i) a polypeptide comprising a single chain Fv (scFv) comprising a calmodulin and a variable region of a heavy chain of an immunoglobulin (VH) and a variable region of a light chain of the immunoglobulin (VL), wherein said VH and VL are linked via said calmodulin, wherein said calmodulin is a circularly permutated calmodulin,
   ii) a calmodulin binding peptide, wherein said calmodulin binding peptide is not M13 peptide,
   iii) Ca2+ ions,
   wherein the binding of said calmodulin-binding peptide and of said Ca2+ ions to Ca2+ binding site of said calmodulin affects the binding of said polypeptide to an antigen to be bound by said polypeptide,
   wherein said circularly permutated calmodulin has the sequence selected from the group consisting of sequences SEQ ID NO: 67 to SEQ ID NO: 123, and wherein said calmodulin binding peptide has the sequence selected from the group consisting of sequences SEQ ID NO: 1 to SEQ ID NO: 52 and SEQ ID NO:54 to SEQ ID NO:65.

2. The composition of claim 1, wherein said binding of said calmodulin-binding peptide and of Ca2+ ions to Ca2+ binding site of said calmodulin enhances or reduces the affinity of said polypeptide to said antigen.

3. The composition of claim 1, wherein said permutated calmodulin has the sequence selected from the group consisting of sequences SEQ ID NO: 67 and SEQ ID NO: 68 and said calmodulin binding peptide has the sequence selected from the group consisting of sequences SEQ ID NO: 1, SEQ ID NO: 7, SEQ ID NO: 8, SEQ ID NO: 9 and SEQ ID NO: 46, or wherein said permutated calmodulin has the sequence selected from the group consisting of sequences SEQ ID NO: 71 and SEQ ID NO: 72 and said calmodulin binding peptide in has the sequence selected from the group consisting of sequences SEQ ID NO: 1, SEQ ID NO: 47, and SEQ ID NO: 51.

4. The composition of claim 1, wherein said polypeptide is part of an antigen binding domain of a chimeric antigen receptor (CAR), said CAR comprising an antigen binding domain, a transmembrane domain and cytoplasmic signaling domain.

5. The composition of claim 1, wherein said polypeptide comprising said circularly permutated calmodulin and said VH and VL, wherein said VH and VL are linked via said circularly permutated calmodulin, is obtainable by the method comprising the steps
   a) creating at least one insertion nucleic acid sequence encoding said circularly permutated calmodulin
   b) creating an acceptor nucleic acid sequence encoding a polypeptide comprising the VH and VL
   c) inserting the at least one insertion sequence of a) into the acceptor sequence of b), wherein the at least one insertion sequence of a) is inserted between the parts of the acceptor sequence b) which encode the VH and VL of b)
   d) transforming an isolated host cell with the nucleic acid sequences of c)
   e) selecting for transformed host cells harboring the sequence(s) of c)
   f) screening for transformed host cells expressing a polypeptide comprising the VH and VL linked via the permutated calmodulin by exposing the polypeptide produced by the transformed host cells to the calmodulin-binding peptide of ii) and identifying the transformed host cells harboring a polypeptide which impact the binding of said polypeptide to the antigen in the presence of Ca2+ ions binding to the Ca2+ binding site of the circularly permutated calmodulin.

* * * * *

SEQUENCE LISTING

```
<160> NUMBER OF SEQ ID NOS: 137

<210> SEQ ID NO 1
<211> LENGTH: 26
<212> TYPE: PRT
<213> ORGANISM: artificial sequence
<220> FEATURE:
<223> OTHER INFORMATION: M13 peptide (WT, L); peptide from protein of
      Oryctolagus cuniculus

<400> SEQUENCE: 1

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 2
<211> LENGTH: 25
<212> TYPE: PRT
<213> ORGANISM: artificial sequence
<220> FEATURE:
<223> OTHER INFORMATION: M13 peptide (WT, S); peptide from protein of
      Oryctolagus cuniculus

<400> SEQUENCE: 2

Lys Arg Arg Trp Lys Lys Asn Phe Ile Ala Val Ser Ala Ala Asn Arg
1               5                   10                  15

Phe Lys Lys Ile Ser Ser Ser Gly Ala
            20                  25

<210> SEQ ID NO 3
<211> LENGTH: 19
<212> TYPE: PRT
<213> ORGANISM: artificial sequence
<220> FEATURE:
<223> OTHER INFORMATION: M13 peptide (WT, XS); peptide from protein of
      Oryctolagus cuniculus

<400> SEQUENCE: 3

Arg Trp Lys Lys Asn Phe Ile Ala Val Ser Ala Ala Asn Arg Phe Lys
1               5                   10                  15

Lys Ile Ser

<210> SEQ ID NO 4
<211> LENGTH: 18
<212> TYPE: PRT
<213> ORGANISM: artificial sequence
<220> FEATURE:
<223> OTHER INFORMATION: M13-Var2

<400> SEQUENCE: 4
```

```
Trp Lys Lys Asn Phe Ile Ala Val Ser Ala Ala Asn Arg Phe Lys Lys
1               5                   10                  15

Ile Ser

<210> SEQ ID NO 5
<211> LENGTH: 18
<212> TYPE: PRT
<213> ORGANISM: artificial sequence
<220> FEATURE:
<223> OTHER INFORMATION: M13-Var3

<400> SEQUENCE: 5

Arg Trp Lys Lys Asn Phe Ile Ala Val Ser Ala Ala Asn Arg Phe Lys
1               5                   10                  15

Lys Ile

<210> SEQ ID NO 6
<211> LENGTH: 17
<212> TYPE: PRT
<213> ORGANISM: artificial sequence
<220> FEATURE:
<223> OTHER INFORMATION: M13-Var4

<400> SEQUENCE: 6

Arg Trp Lys Lys Asn Phe Ile Ala Val Ser Ala Ala Asn Arg Phe Lys
1               5                   10                  15

Lys

<210> SEQ ID NO 7
<211> LENGTH: 19
<212> TYPE: PRT
<213> ORGANISM: artificial sequence
<220> FEATURE:
<223> OTHER INFORMATION: M13-Var5

<400> SEQUENCE: 7

Arg Trp Lys Lys Ala Phe Ile Ala Val Ser Ala Ala Asn Arg Phe Lys
1               5                   10                  15

Lys Ile Ser

<210> SEQ ID NO 8
<211> LENGTH: 18
<212> TYPE: PRT
<213> ORGANISM: artificial sequence
<220> FEATURE:
<223> OTHER INFORMATION: M13-Var6

<400> SEQUENCE: 8

Trp Lys Lys Ala Phe Ile Ala Val Ser Ala Ala Asn Arg Phe Lys Lys
1               5                   10                  15

Ile Ser

<210> SEQ ID NO 9
<211> LENGTH: 18
<212> TYPE: PRT
<213> ORGANISM: artificial sequence
<220> FEATURE:
<223> OTHER INFORMATION: M13-Var7

<400> SEQUENCE: 9

Arg Trp Lys Lys Ala Phe Ile Ala Val Ser Ala Ala Asn Arg Phe Lys
1               5                   10                  15

Lys Ile
```

```
<210> SEQ ID NO 10
<211> LENGTH: 17
<212> TYPE: PRT
<213> ORGANISM: artificial sequence
<220> FEATURE:
<223> OTHER INFORMATION: M13-Var8

<400> SEQUENCE: 10

Arg Trp Lys Lys Ala Phe Ile Ala Val Ser Ala Ala Asn Arg Phe Lys
1               5                   10                  15

Lys

<210> SEQ ID NO 11
<211> LENGTH: 19
<212> TYPE: PRT
<213> ORGANISM: artificial sequence
<220> FEATURE:
<223> OTHER INFORMATION: M13-Var9

<400> SEQUENCE: 11

Arg Trp Lys Lys Asn Ile Ile Ala Val Ser Ala Ala Asn Arg Phe Lys
1               5                   10                  15

Lys Ile Ser

<210> SEQ ID NO 12
<211> LENGTH: 19
<212> TYPE: PRT
<213> ORGANISM: artificial sequence
<220> FEATURE:
<223> OTHER INFORMATION: M13-Var10

<400> SEQUENCE: 12

Arg Trp Lys Lys Asn Phe Ile Lys Val Ser Ala Ala Asn Arg Phe Lys
1               5                   10                  15

Lys Ile Ser

<210> SEQ ID NO 13
<211> LENGTH: 19
<212> TYPE: PRT
<213> ORGANISM: artificial sequence
<220> FEATURE:
<223> OTHER INFORMATION: M13-Var11

<400> SEQUENCE: 13

Arg Trp Lys Lys Asn Phe Ile Ala Val Leu Ala Ala Asn Arg Phe Lys
1               5                   10                  15

Lys Ile Ser

<210> SEQ ID NO 14
<211> LENGTH: 19
<212> TYPE: PRT
<213> ORGANISM: artificial sequence
<220> FEATURE:
<223> OTHER INFORMATION: M13-Var12

<400> SEQUENCE: 14

Arg Trp Lys Lys Asn Phe Ile Ala Val Ser Ala Ile Asn Arg Phe Lys
1               5                   10                  15

Lys Ile Ser

<210> SEQ ID NO 15
<211> LENGTH: 19
```

```
<212> TYPE: PRT
<213> ORGANISM: artificial sequence
<220> FEATURE:
<223> OTHER INFORMATION: M13-Var13

<400> SEQUENCE: 15

Arg Trp Lys Lys Ala Ile Ile Lys Val Leu Ala Ile Asn Arg Phe Lys
1               5                   10                  15

Lys Ile Ser

<210> SEQ ID NO 16
<211> LENGTH: 19
<212> TYPE: PRT
<213> ORGANISM: artificial sequence
<220> FEATURE:
<223> OTHER INFORMATION: M13-Var14

<400> SEQUENCE: 16

Arg Trp Lys Lys Ala Ile Ile Lys Val Leu Ala Ala Asn Arg Phe Lys
1               5                   10                  15

Lys Ile Ser

<210> SEQ ID NO 17
<211> LENGTH: 19
<212> TYPE: PRT
<213> ORGANISM: artificial sequence
<220> FEATURE:
<223> OTHER INFORMATION: M13-Var15

<400> SEQUENCE: 17

Arg Trp Lys Lys Ala Ile Ile Lys Val Ser Ala Ala Asn Arg Phe Lys
1               5                   10                  15

Lys Ile Ser

<210> SEQ ID NO 18
<211> LENGTH: 19
<212> TYPE: PRT
<213> ORGANISM: artificial sequence
<220> FEATURE:
<223> OTHER INFORMATION: M13-Var16

<400> SEQUENCE: 18

Arg Trp Lys Lys Ala Ile Ile Ala Val Ser Ala Ala Asn Arg Phe Lys
1               5                   10                  15

Lys Ile Ser

<210> SEQ ID NO 19
<211> LENGTH: 19
<212> TYPE: PRT
<213> ORGANISM: artificial sequence
<220> FEATURE:
<223> OTHER INFORMATION: M13-Var17

<400> SEQUENCE: 19

Arg Trp Lys Lys Ala Phe Ile Lys Val Leu Ala Ile Asn Arg Phe Lys
1               5                   10                  15

Lys Ile Ser

<210> SEQ ID NO 20
<211> LENGTH: 19
<212> TYPE: PRT
<213> ORGANISM: artificial sequence
<220> FEATURE:
<223> OTHER INFORMATION: M13-Var18
```

```
<400> SEQUENCE: 20

Arg Trp Lys Lys Ala Phe Ile Ala Val Leu Ala Ile Asn Arg Phe Lys
1               5                   10                  15

Lys Ile Ser

<210> SEQ ID NO 21
<211> LENGTH: 19
<212> TYPE: PRT
<213> ORGANISM: artificial sequence
<220> FEATURE:
<223> OTHER INFORMATION: M13-Var19

<400> SEQUENCE: 21

Arg Trp Lys Lys Ala Phe Ile Ala Val Ser Ala Ile Asn Arg Phe Lys
1               5                   10                  15

Lys Ile Ser

<210> SEQ ID NO 22
<211> LENGTH: 19
<212> TYPE: PRT
<213> ORGANISM: artificial sequence
<220> FEATURE:
<223> OTHER INFORMATION: M13-Var20

<400> SEQUENCE: 22

Arg Trp Lys Lys Asn Ile Ile Lys Val Leu Ala Ile Asn Arg Phe Lys
1               5                   10                  15

Lys Ile Ser

<210> SEQ ID NO 23
<211> LENGTH: 19
<212> TYPE: PRT
<213> ORGANISM: artificial sequence
<220> FEATURE:
<223> OTHER INFORMATION: M13-Var21

<400> SEQUENCE: 23

Arg Trp Lys Lys Asn Phe Ile Lys Val Leu Ala Ile Asn Arg Phe Lys
1               5                   10                  15

Lys Ile Ser

<210> SEQ ID NO 24
<211> LENGTH: 19
<212> TYPE: PRT
<213> ORGANISM: artificial sequence
<220> FEATURE:
<223> OTHER INFORMATION: M13-Var22

<400> SEQUENCE: 24

Arg Trp Lys Lys Asn Phe Ile Ala Val Leu Ala Ile Asn Arg Phe Lys
1               5                   10                  15

Lys Ile Ser

<210> SEQ ID NO 25
<211> LENGTH: 19
<212> TYPE: PRT
<213> ORGANISM: artificial sequence
<220> FEATURE:
<223> OTHER INFORMATION: M13-Var23

<400> SEQUENCE: 25

Arg Trp Lys Lys Ala Ile Ile Lys Val Ser Ala Ile Asn Arg Phe Lys
```

-continued

```
1               5                   10                  15
Lys Ile Ser

<210> SEQ ID NO 26
<211> LENGTH: 19
<212> TYPE: PRT
<213> ORGANISM: artificial sequence
<220> FEATURE:
<223> OTHER INFORMATION: M13-Var24

<400> SEQUENCE: 26

Arg Trp Lys Lys Ala Ile Ile Ala Val Ser Ala Ile Asn Arg Phe Lys
1               5                   10                  15

Lys Ile Ser

<210> SEQ ID NO 27
<211> LENGTH: 19
<212> TYPE: PRT
<213> ORGANISM: artificial sequence
<220> FEATURE:
<223> OTHER INFORMATION: M13-Var25

<400> SEQUENCE: 27

Arg Trp Lys Lys Ala Ile Ile Ala Val Leu Ala Ile Asn Arg Phe Lys
1               5                   10                  15

Lys Ile Ser

<210> SEQ ID NO 28
<211> LENGTH: 19
<212> TYPE: PRT
<213> ORGANISM: artificial sequence
<220> FEATURE:
<223> OTHER INFORMATION: M13-Var26

<400> SEQUENCE: 28

Arg Trp Lys Lys Ala Phe Ile Lys Val Ser Ala Ala Asn Arg Phe Lys
1               5                   10                  15

Lys Ile Ser

<210> SEQ ID NO 29
<211> LENGTH: 19
<212> TYPE: PRT
<213> ORGANISM: artificial sequence
<220> FEATURE:
<223> OTHER INFORMATION: M13-Var27

<400> SEQUENCE: 29

Arg Trp Lys Lys Ala Phe Ile Ala Val Leu Ala Ala Asn Arg Phe Lys
1               5                   10                  15

Lys Ile Ser

<210> SEQ ID NO 30
<211> LENGTH: 19
<212> TYPE: PRT
<213> ORGANISM: artificial sequence
<220> FEATURE:
<223> OTHER INFORMATION: M13-Var28

<400> SEQUENCE: 30

Arg Trp Lys Lys Ala Ile Ile Ala Val Leu Ala Ala Asn Arg Phe Lys
1               5                   10                  15

Lys Ile Ser
```

```
<210> SEQ ID NO 31
<211> LENGTH: 19
<212> TYPE: PRT
<213> ORGANISM: artificial sequence
<220> FEATURE:
<223> OTHER INFORMATION: M13-Var29

<400> SEQUENCE: 31

Arg Trp Lys Lys Ala Phe Ile Lys Val Leu Ala Ala Asn Arg Phe Lys
1               5                   10                  15

Lys Ile Ser

<210> SEQ ID NO 32
<211> LENGTH: 19
<212> TYPE: PRT
<213> ORGANISM: artificial sequence
<220> FEATURE:
<223> OTHER INFORMATION: M13-Var30

<400> SEQUENCE: 32

Arg Trp Lys Lys Ala Phe Ile Lys Val Ser Ala Ile Asn Arg Phe Lys
1               5                   10                  15

Lys Ile Ser

<210> SEQ ID NO 33
<211> LENGTH: 19
<212> TYPE: PRT
<213> ORGANISM: artificial sequence
<220> FEATURE:
<223> OTHER INFORMATION: M13-Var31

<400> SEQUENCE: 33

Arg Trp Lys Lys Asn Ile Ile Lys Val Leu Ala Ala Asn Arg Phe Lys
1               5                   10                  15

Lys Ile Ser

<210> SEQ ID NO 34
<211> LENGTH: 19
<212> TYPE: PRT
<213> ORGANISM: artificial sequence
<220> FEATURE:
<223> OTHER INFORMATION: M13-Var32

<400> SEQUENCE: 34

Arg Trp Lys Lys Asn Ile Ile Lys Val Ser Ala Ala Asn Arg Phe Lys
1               5                   10                  15

Lys Ile Ser

<210> SEQ ID NO 35
<211> LENGTH: 19
<212> TYPE: PRT
<213> ORGANISM: artificial sequence
<220> FEATURE:
<223> OTHER INFORMATION: M13-Var33

<400> SEQUENCE: 35

Arg Trp Lys Lys Asn Ile Ile Ala Val Leu Ala Ile Asn Arg Phe Lys
1               5                   10                  15

Lys Ile Ser

<210> SEQ ID NO 36
<211> LENGTH: 19
<212> TYPE: PRT
```

```
<213> ORGANISM: artificial sequence
<220> FEATURE:
<223> OTHER INFORMATION: M13-Var34

<400> SEQUENCE: 36

Arg Trp Lys Lys Asn Ile Ile Ala Val Leu Ala Ala Asn Arg Phe Lys
1               5                   10                  15

Lys Ile Ser

<210> SEQ ID NO 37
<211> LENGTH: 19
<212> TYPE: PRT
<213> ORGANISM: artificial sequence
<220> FEATURE:
<223> OTHER INFORMATION: M13-Var35

<400> SEQUENCE: 37

Arg Trp Lys Lys Asn Ile Ile Ala Val Ser Ala Ile Asn Arg Phe Lys
1               5                   10                  15

Lys Ile Ser

<210> SEQ ID NO 38
<211> LENGTH: 19
<212> TYPE: PRT
<213> ORGANISM: artificial sequence
<220> FEATURE:
<223> OTHER INFORMATION: M13-Var36

<400> SEQUENCE: 38

Arg Trp Lys Lys Asn Asp Ile Ala Val Ser Ala Ala Asn Arg Phe Lys
1               5                   10                  15

Lys Ile Ser

<210> SEQ ID NO 39
<211> LENGTH: 19
<212> TYPE: PRT
<213> ORGANISM: artificial sequence
<220> FEATURE:
<223> OTHER INFORMATION: M13-Var37

<400> SEQUENCE: 39

Arg Trp Lys Lys Asn Phe Ile Asp Val Ser Ala Ala Asn Arg Phe Lys
1               5                   10                  15

Lys Ile Ser

<210> SEQ ID NO 40
<211> LENGTH: 19
<212> TYPE: PRT
<213> ORGANISM: artificial sequence
<220> FEATURE:
<223> OTHER INFORMATION: M13-Var38

<400> SEQUENCE: 40

Arg Trp Lys Lys Asn Phe Ile Ala Val His Ala Ala Asn Arg Phe Lys
1               5                   10                  15

Lys Ile Ser

<210> SEQ ID NO 41
<211> LENGTH: 19
<212> TYPE: PRT
<213> ORGANISM: artificial sequence
<220> FEATURE:
<223> OTHER INFORMATION: M13-Var39
```

```
<400> SEQUENCE: 41

Arg Trp Lys Lys Asn Phe Ile Ala Val Ser Ala Arg Asn Arg Phe Lys
1               5                   10                  15

Lys Ile Ser

<210> SEQ ID NO 42
<211> LENGTH: 17
<212> TYPE: PRT
<213> ORGANISM: artificial sequence
<220> FEATURE:
<223> OTHER INFORMATION: CBP-Var2; peptide from protein of Homo sapiens

<400> SEQUENCE: 42

Gly Val Arg Asn Ile Lys Ser Met Trp Glu Lys Gly Asn Val Phe Ser
1               5                   10                  15

Ser

<210> SEQ ID NO 43
<211> LENGTH: 20
<212> TYPE: PRT
<213> ORGANISM: artificial sequence
<220> FEATURE:
<223> OTHER INFORMATION: CBP-Var3; peptide from protein of Homo sapiens

<400> SEQUENCE: 43

Ala Arg Arg Lys Leu Lys Ala Ala Val Lys Ala Val Val Ala Ser Ser
1               5                   10                  15

Arg Leu Gly Ser
            20

<210> SEQ ID NO 44
<211> LENGTH: 25
<212> TYPE: PRT
<213> ORGANISM: artificial sequence
<220> FEATURE:
<223> OTHER INFORMATION: CBP-Var4; peptide from protein of Oryctolagus
      cuniculus

<400> SEQUENCE: 44

Phe Met Asn Asn Trp Glu Val Tyr Lys Leu Leu Ala His Ile Arg Pro
1               5                   10                  15

Pro Ala Pro Lys Ser Gly Ser Tyr Thr
            20                  25

<210> SEQ ID NO 45
<211> LENGTH: 24
<212> TYPE: PRT
<213> ORGANISM: artificial sequence
<220> FEATURE:
<223> OTHER INFORMATION: CBP-Var5; peptide from protein of Rattus
      norvegicus

<400> SEQUENCE: 45

Ala Arg Lys Glu Val Ile Arg Asn Lys Ile Arg Ala Ile Gly Lys Met
1               5                   10                  15

Ala Arg Val Phe Ser Val Leu Arg
            20

<210> SEQ ID NO 46
<211> LENGTH: 24
<212> TYPE: PRT
<213> ORGANISM: artificial sequence
<220> FEATURE:
<223> OTHER INFORMATION: CBP-Var6; peptide derived from protein of
```

Gallus gallus

<400> SEQUENCE: 46

Arg Gly Gln Ile Leu Trp Phe Arg Gly Leu Asn Arg Ile Gln Thr Gln
1               5                   10                  15

Ile Lys Val Val Asn Ala Phe Ser
            20

<210> SEQ ID NO 47
<211> LENGTH: 24
<212> TYPE: PRT
<213> ORGANISM: artificial sequence
<220> FEATURE:
<223> OTHER INFORMATION: CBP-Var8; peptide from protein of Homo sapiens

<400> SEQUENCE: 47

Lys Thr Ala Ser Pro Trp Lys Ser Ala Arg Leu Met Val His Thr Val
1               5                   10                  15

Ala Thr Phe Asn Ser Ile Lys Glu
            20

<210> SEQ ID NO 48
<211> LENGTH: 25
<212> TYPE: PRT
<213> ORGANISM: artificial sequence
<220> FEATURE:
<223> OTHER INFORMATION: CBP-Var9; peptide from protein of Mus musculus

<400> SEQUENCE: 48

Lys Lys Lys Lys Lys Arg Phe Ser Phe Lys Lys Ser Phe Lys Leu Ser
1               5                   10                  15

Gly Phe Ser Phe Lys Lys Ser Lys Lys
            20                  25

<210> SEQ ID NO 49
<211> LENGTH: 24
<212> TYPE: PRT
<213> ORGANISM: artificial sequence
<220> FEATURE:
<223> OTHER INFORMATION: CBP-Var10; peptide from protein of Homo sapiens

<400> SEQUENCE: 49

Lys Lys Lys Ala Thr Phe Arg Ala Ile Thr Ser Thr Leu Ala Ser Ser
1               5                   10                  15

Phe Lys Arg Arg Arg Ser Ser Lys
            20

<210> SEQ ID NO 50
<211> LENGTH: 23
<212> TYPE: PRT
<213> ORGANISM: artificial sequence
<220> FEATURE:
<223> OTHER INFORMATION: CBP-Var11; peptide from protein of Homo sapiens

<400> SEQUENCE: 50

Lys Arg Arg Ala Ile Gly Phe Lys Lys Leu Ala Glu Ala Val Lys Phe
1               5                   10                  15

Ser Ala Lys Leu Met Gly Gln
            20

<210> SEQ ID NO 51
<211> LENGTH: 20
<212> TYPE: PRT
<213> ORGANISM: artificial sequence

```
<220> FEATURE:
<223> OTHER INFORMATION: CBP-Var12; peptide from protein of Homo sapiens

<400> SEQUENCE: 51

Arg Lys Lys Thr Phe Lys Glu Val Ala Asn Ala Val Lys Ile Ser Ala
1               5                   10                  15

Ser Leu Met Gly
            20

<210> SEQ ID NO 52
<211> LENGTH: 25
<212> TYPE: PRT
<213> ORGANISM: artificial sequence
<220> FEATURE:
<223> OTHER INFORMATION: CBP-Var13; peptide from protein of Homo sapiens

<400> SEQUENCE: 52

Ala Ala Ala Arg Lys Glu Val Ile Arg Asn Lys Ile Arg Ala Ile Gly
1               5                   10                  15

Lys Met Ala Arg Val Phe Ser Val Leu
            20                  25

<210> SEQ ID NO 53
<211> LENGTH: 20
<212> TYPE: PRT
<213> ORGANISM: artificial sequence
<220> FEATURE:
<223> OTHER INFORMATION: CBP-Var16; peptide from protein of Gallus
      gallus

<400> SEQUENCE: 53

Leu Arg Arg Gly Gln Ile Leu Trp Phe Arg Gly Leu Asn Arg Ile Gln
1               5                   10                  15

Thr Gln Ile Lys
            20

<210> SEQ ID NO 54
<211> LENGTH: 17
<212> TYPE: PRT
<213> ORGANISM: artificial sequence
<220> FEATURE:
<223> OTHER INFORMATION: CBP-Var18; peptide from protein of Homo sapiens

<400> SEQUENCE: 54

Ala Thr Leu Asp Ala Leu Leu Ala Ala Leu Arg Arg Ile Gln Arg Ala
1               5                   10                  15

Asp

<210> SEQ ID NO 55
<211> LENGTH: 19
<212> TYPE: PRT
<213> ORGANISM: artificial sequence
<220> FEATURE:
<223> OTHER INFORMATION: CBP-Var19; peptide from protein of Homo sapiens

<400> SEQUENCE: 55

Arg Ala Ala Asn Leu Trp Pro Ser Pro Leu Met Ile Lys Arg Ser Lys
1               5                   10                  15

Lys Asn Ser

<210> SEQ ID NO 56
<211> LENGTH: 21
<212> TYPE: PRT
<213> ORGANISM: artificial sequence
```

```
<220> FEATURE:
<223> OTHER INFORMATION: CBP-Var20; peptide from protein of Homo sapiens

<400> SEQUENCE: 56

Lys Ile Tyr Ala Ala Met Met Ile Met Glu Tyr Tyr Arg Gln Ser Lys
1               5                   10                  15

Ala Lys Lys Leu Gln
            20

<210> SEQ ID NO 57
<211> LENGTH: 21
<212> TYPE: PRT
<213> ORGANISM: artificial sequence
<220> FEATURE:
<223> OTHER INFORMATION: CBP-Var21; peptide from protein of Homo sapiens

<400> SEQUENCE: 57

Lys Ile Tyr Ala Ala Met Met Ile Met Asp Tyr Tyr Lys Gln Ser Lys
1               5                   10                  15

Val Lys Lys Gln Arg
            20

<210> SEQ ID NO 58
<211> LENGTH: 21
<212> TYPE: PRT
<213> ORGANISM: artificial sequence
<220> FEATURE:
<223> OTHER INFORMATION: CBP-Var22; peptide from protein of Homo sapiens

<400> SEQUENCE: 58

Lys Phe Tyr Ala Thr Phe Leu Ile Gln Glu His Phe Arg Lys Phe Met
1               5                   10                  15

Lys Arg Gln Glu Glu
            20

<210> SEQ ID NO 59
<211> LENGTH: 24
<212> TYPE: PRT
<213> ORGANISM: artificial sequence
<220> FEATURE:
<223> OTHER INFORMATION: CBP-Var23; peptide derived from protein of Homo
      sapiens

<400> SEQUENCE: 59

Gly Thr Gly Ala Ala Leu Ser Trp Gln Ala Ala Ile Asp Ala Ala Arg
1               5                   10                  15

Gln Ala Lys Leu Met Gly Ser Ala
            20

<210> SEQ ID NO 60
<211> LENGTH: 23
<212> TYPE: PRT
<213> ORGANISM: artificial sequence
<220> FEATURE:
<223> OTHER INFORMATION: CBP-Var24; peptide derived from protein of
      Oryctolagus cuniculus

<400> SEQUENCE: 60

His Met Gly Lys Val Tyr Ala Ala Leu Met Ile Phe Asp Phe Tyr Lys
1               5                   10                  15

Gln Asn Lys Thr Ser Arg Asp
            20

<210> SEQ ID NO 61
```

```
<211> LENGTH: 23
<212> TYPE: PRT
<213> ORGANISM: artificial sequence
<220> FEATURE:
<223> OTHER INFORMATION: CBP-Var25; peptide derived from protein of Homo
      sapiens

<400> SEQUENCE: 61

Gly His Met Gly Lys Ile Tyr Ala Ala Met Met Ile Met Asp Tyr Tyr
1               5                   10                  15

Lys Gln Ser Lys Val Lys Lys
            20

<210> SEQ ID NO 62
<211> LENGTH: 22
<212> TYPE: PRT
<213> ORGANISM: artificial sequence
<220> FEATURE:
<223> OTHER INFORMATION: CBP-Var26; peptide derived from protein of Ovis
      aries musimom

<400> SEQUENCE: 62

His Met Gly Lys Ile Tyr Ala Ala Met Met Ile Met Glu Tyr Tyr Arg
1               5                   10                  15

Gln Ser Lys Ala Lys Lys
            20

<210> SEQ ID NO 63
<211> LENGTH: 25
<212> TYPE: PRT
<213> ORGANISM: artificial sequence
<220> FEATURE:
<223> OTHER INFORMATION: CBP-Var27; peptide from protein of Homo sapiens

<400> SEQUENCE: 63

Ile Lys Lys Asn Phe Ala Lys Ser Lys Trp Lys Gln Ala Phe Asn Ala
1               5                   10                  15

Thr Ala Val Val Arg His Met Arg Lys
            20                  25

<210> SEQ ID NO 64
<211> LENGTH: 25
<212> TYPE: PRT
<213> ORGANISM: artificial sequence
<220> FEATURE:
<223> OTHER INFORMATION: CBP-Var28; peptide from protein of Homo sapiens

<400> SEQUENCE: 64

Leu Lys Lys Phe Asn Ala Arg Arg Lys Leu Lys Gly Ala Ile Leu Thr
1               5                   10                  15

Thr Met Leu Ala Thr Arg Asn Phe Ser
            20                  25

<210> SEQ ID NO 65
<211> LENGTH: 22
<212> TYPE: PRT
<213> ORGANISM: artificial sequence
<220> FEATURE:
<223> OTHER INFORMATION: CBP-Var30; peptide from protein of Homo sapiens

<400> SEQUENCE: 65

Ala Lys Ser Lys Trp Lys Gln Ala Phe Asn Ala Thr Ala Val Val Arg
1               5                   10                  15

His Met Arg Lys Leu Gln
            20
```

```
<210> SEQ ID NO 66
<211> LENGTH: 148
<212> TYPE: PRT
<213> ORGANISM: artificial sequence
<220> FEATURE:
<223> OTHER INFORMATION: Calmodulin from Homo sapiens (WT sequence): lin

<400> SEQUENCE: 66

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 67
<211> LENGTH: 152
<212> TYPE: PRT
<213> ORGANISM: artificial sequence
<220> FEATURE:
<223> OTHER INFORMATION: permutated calmodulin-variant: M-1

<400> SEQUENCE: 67

Met Lys Asp Thr Asp Ser Glu Glu Glu Ile Arg Glu Ala Phe Arg Val
1               5                   10                  15

Phe Asp Lys Asp Gly Asn Gly Tyr Ile Ser Ala Ala Glu Leu Arg His
            20                  25                  30

Val Met Thr Asn Leu Gly Glu Lys Leu Thr Asp Glu Glu Val Asp Glu
        35                  40                  45

Met Ile Arg Glu Ala Asp Ile Asp Gly Asp Gly Gln Val Asn Tyr Glu
    50                  55                  60

Glu Phe Val Gln Met Met Thr Ala Lys Gly Gly Ser Gly Ala Asp Gln
65                  70                  75                  80

Leu Thr Glu Glu Gln Ile Ala Glu Phe Lys Glu Ala Phe Ser Leu Phe
                85                  90                  95

Asp Lys Asp Gly Asp Gly Thr Ile Thr Thr Lys Glu Leu Gly Thr Val
            100                 105                 110

Met Arg Ser Leu Gly Gln Asn Pro Thr Glu Ala Glu Leu Gln Asp Met
        115                 120                 125

Ile Asn Glu Val Asp Ala Asp Gly Asn Gly Thr Ile Asp Phe Pro Glu
    130                 135                 140

Phe Leu Thr Met Met Ala Arg Lys
```

145            150

<210> SEQ ID NO 68
<211> LENGTH: 152
<212> TYPE: PRT
<213> ORGANISM: artificial sequence
<220> FEATURE:
<223> OTHER INFORMATION: permutated calmodulin-variant: M-2

<400> SEQUENCE: 68

Ser Glu Glu Glu Ile Arg Glu Ala Phe Arg Val Phe Asp Lys Asp Gly
1               5                   10                  15

Asn Gly Tyr Ile Ser Ala Ala Glu Leu Arg His Val Met Thr Asn Leu
            20                  25                  30

Gly Glu Lys Leu Thr Asp Glu Glu Val Asp Glu Met Ile Arg Glu Ala
        35                  40                  45

Asp Ile Asp Gly Asp Gly Gln Val Asn Tyr Glu Glu Phe Val Gln Met
    50                  55                  60

Met Thr Ala Lys Gly Gly Ser Gly Ala Asp Gln Leu Thr Glu Glu Gln
65                  70                  75                  80

Ile Ala Glu Phe Lys Glu Ala Phe Ser Leu Phe Asp Lys Asp Gly Asp
                85                  90                  95

Gly Thr Ile Thr Thr Lys Glu Leu Gly Thr Val Met Arg Ser Leu Gly
            100                 105                 110

Gln Asn Pro Thr Glu Ala Glu Leu Gln Asp Met Ile Asn Glu Val Asp
        115                 120                 125

Ala Asp Gly Asn Gly Thr Ile Asp Phe Pro Glu Phe Leu Thr Met Met
    130                 135                 140

Ala Arg Lys Met Lys Asp Thr Asp
145                 150

<210> SEQ ID NO 69
<211> LENGTH: 152
<212> TYPE: PRT
<213> ORGANISM: artificial sequence
<220> FEATURE:
<223> OTHER INFORMATION: permutated calmodulin-variant: N-1

<400> SEQUENCE: 69

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

```
Met Thr Ala Lys Gly Gly Ser Gly
145                 150

<210> SEQ ID NO 70
<211> LENGTH: 152
<212> TYPE: PRT
<213> ORGANISM: artificial sequence
<220> FEATURE:
<223> OTHER INFORMATION: permutated calmodulin-variant: N-2

<400> SEQUENCE: 70

Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
                20                  25                  30

Thr Val Met Arg Ser Leu Gly Gln Asn Pro Thr Glu Ala Glu Leu Gln
            35                  40                  45

Asp Met Ile Asn Glu Val Asp Ala Asp Gly Asn Gly Thr Ile Asp Phe
        50                  55                  60

Pro Glu Phe Leu Thr Met Met Ala Arg Lys Met Lys Asp Thr Asp Ser
65                  70                  75                  80

Glu Glu Glu Ile Arg Glu Ala Phe Arg Val Phe Asp Lys Asp Gly Asn
                85                  90                  95

Gly Tyr Ile Ser Ala Ala Glu Leu Arg His Val Met Thr Asn Leu Gly
                100                 105                 110

Glu Lys Leu Thr Asp Glu Glu Val Asp Glu Met Ile Arg Glu Ala Asp
            115                 120                 125

Ile Asp Gly Asp Gly Gln Val Asn Tyr Glu Glu Phe Val Gln Met Met
        130                 135                 140

Thr Ala Lys Gly Gly Ser Gly Ala
145                 150

<210> SEQ ID NO 71
<211> LENGTH: 152
<212> TYPE: PRT
<213> ORGANISM: artificial sequence
<220> FEATURE:
<223> OTHER INFORMATION: permutated calmodulin-variant: C-1

<400> SEQUENCE: 71

Lys Gly Gly Ser Gly Ala Asp Gln Leu Thr Glu Glu Gln Ile Ala Glu
1               5                   10                  15

Phe Lys Glu Ala Phe Ser Leu Phe Asp Lys Asp Gly Asp Gly Thr Ile
                20                  25                  30

Thr Thr Lys Glu Leu Gly Thr Val Met Arg Ser Leu Gly Gln Asn Pro
            35                  40                  45

Thr Glu Ala Glu Leu Gln Asp Met Ile Asn Glu Val Asp Ala Asp Gly
        50                  55                  60

Asn Gly Thr Ile Asp Phe Pro Glu Phe Leu Thr Met Met Ala Arg Lys
65                  70                  75                  80

Met Lys Asp Thr Asp Ser Glu Glu Glu Ile Arg Glu Ala Phe Arg Val
                85                  90                  95

Phe Asp Lys Asp Gly Asn Gly Tyr Ile Ser Ala Ala Glu Leu Arg His
                100                 105                 110

Val Met Thr Asn Leu Gly Glu Lys Leu Thr Asp Glu Glu Val Asp Glu
            115                 120                 125

Met Ile Arg Glu Ala Asp Ile Asp Gly Asp Gly Gln Val Asn Tyr Glu
        130                 135                 140
```

```
Glu Phe Val Gln Met Met Thr Ala
145                 150
```

<210> SEQ ID NO 72
<211> LENGTH: 152
<212> TYPE: PRT
<213> ORGANISM: artificial sequence
<220> FEATURE:
<223> OTHER INFORMATION: permutated calmodulin-variant: C-2

<400> SEQUENCE: 72

```
Ala Lys Gly Gly Ser Gly Ala Asp Gln Leu Thr Glu Glu Gln Ile Ala
1               5                   10                  15

Glu Phe Lys Glu Ala Phe Ser Leu Phe Asp Lys Asp Gly Asp Gly Thr
                20                  25                  30

Ile Thr Thr Lys Glu Leu Gly Thr Val Met Arg Ser Leu Gly Gln Asn
            35                  40                  45

Pro Thr Glu Ala Glu Leu Gln Asp Met Ile Asn Glu Val Asp Ala Asp
    50                  55                  60

Gly Asn Gly Thr Ile Asp Phe Pro Glu Phe Leu Thr Met Met Ala Arg
65                  70                  75                  80

Lys Met Lys Asp Thr Asp Ser Glu Glu Glu Ile Arg Glu Ala Phe Arg
                85                  90                  95

Val Phe Asp Lys Asp Gly Asn Gly Tyr Ile Ser Ala Ala Glu Leu Arg
                100                 105                 110

His Val Met Thr Asn Leu Gly Glu Lys Leu Thr Asp Glu Glu Val Asp
            115                 120                 125

Glu Met Ile Arg Glu Ala Asp Ile Asp Gly Asp Gly Gln Val Asn Tyr
    130                 135                 140

Glu Glu Phe Val Gln Met Met Thr
145                 150
```

<210> SEQ ID NO 73
<211> LENGTH: 152
<212> TYPE: PRT
<213> ORGANISM: artificial sequence
<220> FEATURE:
<223> OTHER INFORMATION: permutated calmodulin-variant: 1-S

<400> SEQUENCE: 73

```
Ser Gly Ala Asp Gln Leu Thr Glu Glu Gln Ile Ala Glu Phe Lys Glu
1               5                   10                  15

Ala Phe Ser Leu Phe Asp Lys Asp Gly Asp Gly Thr Ile Thr Thr Lys
                20                  25                  30

Glu Leu Gly Thr Val Met Arg Ser Leu Gly Gln Asn Pro Thr Glu Ala
            35                  40                  45

Glu Leu Gln Asp Met Ile Asn Glu Val Asp Ala Asp Gly Asn Gly Thr
    50                  55                  60

Ile Asp Phe Pro Glu Phe Leu Thr Met Met Ala Arg Lys Met Lys Asp
65                  70                  75                  80

Thr Asp Ser Glu Glu Glu Ile Arg Glu Ala Phe Arg Val Phe Asp Lys
                85                  90                  95

Asp Gly Asn Gly Tyr Ile Ser Ala Ala Glu Leu Arg His Val Met Thr
                100                 105                 110

Asn Leu Gly Glu Lys Leu Thr Asp Glu Glu Val Asp Glu Met Ile Arg
            115                 120                 125

Glu Ala Asp Ile Asp Gly Asp Gly Gln Val Asn Tyr Glu Glu Phe Val
```

```
                130                 135                 140
Gln Met Met Thr Ala Lys Gly Gly
145                 150

<210> SEQ ID NO 74
<211> LENGTH: 152
<212> TYPE: PRT
<213> ORGANISM: artificial sequence
<220> FEATURE:
<223> OTHER INFORMATION: permutated calmodulin-variant: 2-G

<400> SEQUENCE: 74

Gly Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asn Gly Thr Ile
    50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys Gly Gly Ser
145                 150

<210> SEQ ID NO 75
<211> LENGTH: 152
<212> TYPE: PRT
<213> ORGANISM: artificial sequence
<220> FEATURE:
<223> OTHER INFORMATION: permutated calmodulin-variant: 5-Q

<400> SEQUENCE: 75

Gln Leu Thr Glu Glu Gln Ile Ala Glu Phe Lys Glu Ala Phe Ser Leu
1               5                   10                  15

Phe Asp Lys Asp Gly Asp Gly Thr Ile Thr Thr Lys Glu Leu Gly Thr
            20                  25                  30

Val Met Arg Ser Leu Gly Gln Asn Pro Thr Glu Ala Glu Leu Gln Asp
        35                  40                  45

Met Ile Asn Glu Val Asp Ala Asp Gly Asn Gly Thr Ile Asp Phe Pro
    50                  55                  60

Glu Phe Leu Thr Met Met Ala Arg Lys Met Lys Asp Thr Asp Ser Glu
65                  70                  75                  80

Glu Glu Ile Arg Glu Ala Phe Arg Val Phe Asp Lys Asp Gly Asn Gly
                85                  90                  95

Tyr Ile Ser Ala Ala Glu Leu Arg His Val Met Thr Asn Leu Gly Glu
            100                 105                 110

Lys Leu Thr Asp Glu Glu Val Asp Glu Met Ile Arg Glu Ala Asp Ile
        115                 120                 125
```

```
Asp Gly Asp Gly Gln Val Asn Tyr Glu Glu Phe Val Gln Met Met Thr
            130                 135                 140
Ala Lys Gly Gly Ser Gly Ala Asp
145                 150

<210> SEQ ID NO 76
<211> LENGTH: 152
<212> TYPE: PRT
<213> ORGANISM: artificial sequence
<220> FEATURE:
<223> OTHER INFORMATION: permutated calmodulin-variant: 6-L

<400> SEQUENCE: 76

Leu Thr Glu Glu Gln Ile Ala Glu Phe Lys Glu Ala Phe Ser Leu Phe
  1               5                  10                  15
Asp Lys Asp Gly Asp Gly Thr Ile Thr Thr Lys Glu Leu Gly Thr Val
             20                  25                  30
Met Arg Ser Leu Gly Gln Asn Pro Thr Glu Ala Glu Leu Gln Asp Met
         35                  40                  45
Ile Asn Glu Val Asp Ala Asp Gly Asn Gly Thr Ile Asp Phe Pro Glu
 50                  55                  60
Phe Leu Thr Met Met Ala Arg Lys Met Lys Asp Thr Asp Ser Glu Glu
 65                  70                  75                  80
Glu Ile Arg Glu Ala Phe Arg Val Phe Asp Lys Asp Gly Asn Gly Tyr
                 85                  90                  95
Ile Ser Ala Ala Glu Leu Arg His Val Met Thr Asn Leu Gly Glu Lys
            100                 105                 110
Leu Thr Asp Glu Glu Val Asp Glu Met Ile Arg Glu Ala Asp Ile Asp
            115                 120                 125
Gly Asp Gly Gln Val Asn Tyr Glu Glu Phe Val Gln Met Met Thr Ala
        130                 135                 140
Lys Gly Gly Ser Gly Ala Asp Gln
145                 150

<210> SEQ ID NO 77
<211> LENGTH: 152
<212> TYPE: PRT
<213> ORGANISM: artificial sequence
<220> FEATURE:
<223> OTHER INFORMATION: permutated calmodulin-variant: 8-E

<400> SEQUENCE: 77

Glu Glu Gln Ile Ala Glu Phe Lys Glu Ala Phe Ser Leu Phe Asp Lys
  1               5                  10                  15
Asp Gly Asp Gly Thr Ile Thr Thr Lys Glu Leu Gly Thr Val Met Arg
             20                  25                  30
Ser Leu Gly Gln Asn Pro Thr Glu Ala Glu Leu Gln Asp Met Ile Asn
         35                  40                  45
Glu Val Asp Ala Asp Gly Asn Gly Thr Ile Asp Phe Pro Glu Phe Leu
 50                  55                  60
Thr Met Met Ala Arg Lys Met Lys Asp Thr Asp Ser Glu Glu Glu Ile
 65                  70                  75                  80
Arg Glu Ala Phe Arg Val Phe Asp Lys Asp Gly Asn Gly Tyr Ile Ser
                 85                  90                  95
Ala Ala Glu Leu Arg His Val Met Thr Asn Leu Gly Glu Lys Leu Thr
            100                 105                 110
Asp Glu Glu Val Asp Glu Met Ile Arg Glu Ala Asp Ile Asp Gly Asp
            115                 120                 125
```

Gly Gln Val Asn Tyr Glu Glu Phe Val Gln Met Met Thr Ala Lys Gly
            130                 135                 140

Gly Ser Gly Ala Asp Gln Leu Thr
145                 150

<210> SEQ ID NO 78
<211> LENGTH: 152
<212> TYPE: PRT
<213> ORGANISM: artificial sequence
<220> FEATURE:
<223> OTHER INFORMATION: permutated calmodulin-variant: 9-E

<400> SEQUENCE: 78

Glu Gln Ile Ala Glu Phe Lys Glu Ala Phe Ser Leu Phe Asp Lys Asp
1               5                   10                  15

Gly Asp Gly Thr Ile Thr Thr Lys Glu Leu Gly Thr Val Met Arg Ser
            20                  25                  30

Leu Gly Gln Asn Pro Thr Glu Ala Glu Leu Gln Asp Met Ile Asn Glu
        35                  40                  45

Val Asp Ala Asp Gly Asn Gly Thr Ile Asp Phe Pro Glu Phe Leu Thr
    50                  55                  60

Met Met Ala Arg Lys Met Lys Asp Thr Asp Ser Glu Glu Glu Ile Arg
65                  70                  75                  80

Glu Ala Phe Arg Val Phe Asp Lys Asp Gly Asn Gly Tyr Ile Ser Ala
                85                  90                  95

Ala Glu Leu Arg His Val Met Thr Asn Leu Gly Glu Lys Leu Thr Asp
            100                 105                 110

Glu Glu Val Asp Glu Met Ile Arg Glu Ala Asp Ile Asp Gly Asp Gly
        115                 120                 125

Gln Val Asn Tyr Glu Glu Phe Val Gln Met Met Thr Ala Lys Gly Gly
    130                 135                 140

Ser Gly Ala Asp Gln Leu Thr Glu
145                 150

<210> SEQ ID NO 79
<211> LENGTH: 152
<212> TYPE: PRT
<213> ORGANISM: artificial sequence
<220> FEATURE:
<223> OTHER INFORMATION: permutated calmodulin-variant: 10-Q

<400> SEQUENCE: 79

Gln Ile Ala Glu Phe Lys Glu Ala Phe Ser Leu Phe Asp Lys Asp Gly
1               5                   10                  15

Asp Gly Thr Ile Thr Thr Lys Glu Leu Gly Thr Val Met Arg Ser Leu
            20                  25                  30

Gly Gln Asn Pro Thr Glu Ala Glu Leu Gln Asp Met Ile Asn Glu Val
        35                  40                  45

Asp Ala Asp Gly Asn Gly Thr Ile Asp Phe Pro Glu Phe Leu Thr Met
    50                  55                  60

Met Ala Arg Lys Met Lys Asp Thr Asp Ser Glu Glu Glu Ile Arg Glu
65                  70                  75                  80

Ala Phe Arg Val Phe Asp Lys Asp Gly Asn Gly Tyr Ile Ser Ala Ala
                85                  90                  95

Glu Leu Arg His Val Met Thr Asn Leu Gly Glu Lys Leu Thr Asp Glu
            100                 105                 110

Glu Val Asp Glu Met Ile Arg Glu Ala Asp Ile Asp Gly Asp Gly Gln

```
            115                 120                 125
Val Asn Tyr Glu Glu Phe Val Gln Met Met Thr Ala Lys Gly Gly Ser
            130                 135                 140

Gly Ala Asp Gln Leu Thr Glu Glu
145                 150

<210> SEQ ID NO 80
<211> LENGTH: 152
<212> TYPE: PRT
<213> ORGANISM: artificial sequence
<220> FEATURE:
<223> OTHER INFORMATION: permutated calmodulin-variant: 11-I

<400> SEQUENCE: 80

Ile Ala Glu Phe Lys Glu Ala Phe Ser Leu Phe Asp Lys Asp Gly Asp
1               5                   10                  15

Gly Thr Ile Thr Thr Lys Glu Leu Gly Thr Val Met Arg Ser Leu Gly
                20                  25                  30

Gln Asn Pro Thr Glu Ala Glu Leu Gln Asp Met Ile Asn Glu Val Asp
            35                  40                  45

Ala Asp Gly Asn Gly Thr Ile Asp Phe Pro Glu Phe Leu Thr Met Met
50                  55                  60

Ala Arg Lys Met Lys Asp Thr Asp Ser Glu Glu Glu Ile Arg Glu Ala
65                  70                  75                  80

Phe Arg Val Phe Asp Lys Asp Gly Asn Gly Tyr Ile Ser Ala Ala Glu
                85                  90                  95

Leu Arg His Val Met Thr Asn Leu Gly Glu Lys Leu Thr Asp Glu Glu
            100                 105                 110

Val Asp Glu Met Ile Arg Glu Ala Asp Ile Asp Gly Asp Gly Gln Val
        115                 120                 125

Asn Tyr Glu Glu Phe Val Gln Met Met Thr Ala Lys Gly Gly Ser Gly
        130                 135                 140

Ala Asp Gln Leu Thr Glu Glu Gln
145                 150

<210> SEQ ID NO 81
<211> LENGTH: 152
<212> TYPE: PRT
<213> ORGANISM: artificial sequence
<220> FEATURE:
<223> OTHER INFORMATION: permutated calmodulin-variant: 13-E

<400> SEQUENCE: 81

Glu Phe Lys Glu Ala Phe Ser Leu Phe Asp Lys Asp Gly Asp Gly Thr
1               5                   10                  15

Ile Thr Thr Lys Glu Leu Gly Thr Val Met Arg Ser Leu Gly Gln Asn
                20                  25                  30

Pro Thr Glu Ala Glu Leu Gln Asp Met Ile Asn Glu Val Asp Ala Asp
            35                  40                  45

Gly Asn Gly Thr Ile Asp Phe Pro Glu Phe Leu Thr Met Met Ala Arg
50                  55                  60

Lys Met Lys Asp Thr Asp Ser Glu Glu Glu Ile Arg Glu Ala Phe Arg
65                  70                  75                  80

Val Phe Asp Lys Asp Gly Asn Gly Tyr Ile Ser Ala Ala Glu Leu Arg
                85                  90                  95

His Val Met Thr Asn Leu Gly Glu Lys Leu Thr Asp Glu Glu Val Asp
            100                 105                 110
```

```
Glu Met Ile Arg Glu Ala Asp Ile Asp Gly Asp Gly Gln Val Asn Tyr
            115                 120                 125

Glu Glu Phe Val Gln Met Met Thr Ala Lys Gly Gly Ser Gly Ala Asp
        130                 135                 140

Gln Leu Thr Glu Glu Gln Ile Ala
145                 150

<210> SEQ ID NO 82
<211> LENGTH: 152
<212> TYPE: PRT
<213> ORGANISM: artificial sequence
<220> FEATURE:
<223> OTHER INFORMATION: permutated calmodulin-variant: 14-F

<400> SEQUENCE: 82

Phe Lys Glu Ala Phe Ser Leu Phe Asp Lys Asp Gly Asp Gly Thr Ile
1               5                   10                  15

Thr Thr Lys Glu Leu Gly Thr Val Met Arg Ser Leu Gly Gln Asn Pro
            20                  25                  30

Thr Glu Ala Glu Leu Gln Asp Met Ile Asn Glu Val Asp Ala Asp Gly
        35                  40                  45

Asn Gly Thr Ile Asp Phe Pro Glu Phe Leu Thr Met Met Ala Arg Lys
50                  55                  60

Met Lys Asp Thr Asp Ser Glu Glu Ile Arg Glu Ala Phe Arg Val
65                  70                  75                  80

Phe Asp Lys Asp Gly Asn Gly Tyr Ile Ser Ala Ala Glu Leu Arg His
                85                  90                  95

Val Met Thr Asn Leu Gly Glu Lys Leu Thr Asp Glu Glu Val Asp Glu
            100                 105                 110

Met Ile Arg Glu Ala Asp Ile Asp Gly Asp Gly Gln Val Asn Tyr Glu
        115                 120                 125

Glu Phe Val Gln Met Met Thr Ala Lys Gly Gly Ser Gly Ala Asp Gln
    130                 135                 140

Leu Thr Glu Glu Gln Ile Ala Glu
145                 150

<210> SEQ ID NO 83
<211> LENGTH: 152
<212> TYPE: PRT
<213> ORGANISM: artificial sequence
<220> FEATURE:
<223> OTHER INFORMATION: permutated calmodulin-variant: 16-E

<400> SEQUENCE: 83

Glu Ala Phe Ser Leu Phe Asp Lys Asp Gly Asp Gly Thr Ile Thr Thr
1               5                   10                  15

Lys Glu Leu Gly Thr Val Met Arg Ser Leu Gly Gln Asn Pro Thr Glu
            20                  25                  30

Ala Glu Leu Gln Asp Met Ile Asn Glu Val Asp Ala Asp Gly Asn Gly
        35                  40                  45

Thr Ile Asp Phe Pro Glu Phe Leu Thr Met Met Ala Arg Lys Met Lys
    50                  55                  60

Asp Thr Asp Ser Glu Glu Ile Arg Glu Ala Phe Arg Val Phe Asp
65                  70                  75                  80

Lys Asp Gly Asn Gly Tyr Ile Ser Ala Ala Glu Leu Arg His Val Met
                85                  90                  95

Thr Asn Leu Gly Glu Lys Leu Thr Asp Glu Glu Val Asp Glu Met Ile
            100                 105                 110
```

Arg Glu Ala Asp Ile Asp Gly Asp Gly Gln Val Asn Tyr Glu Glu Phe
            115                 120                 125

Val Gln Met Met Thr Ala Lys Gly Gly Ser Gly Ala Asp Gln Leu Thr
        130                 135                 140

Glu Glu Gln Ile Ala Glu Phe Lys
145                 150

<210> SEQ ID NO 84
<211> LENGTH: 152
<212> TYPE: PRT
<213> ORGANISM: artificial sequence
<220> FEATURE:
<223> OTHER INFORMATION: permutated calmodulin-variant: 26-D

<400> SEQUENCE: 84

Asp Gly Thr Ile Thr Thr Lys Glu Leu Gly Thr Val Met Arg Ser Leu
1               5                   10                  15

Gly Gln Asn Pro Thr Glu Ala Glu Leu Gln Asp Met Ile Asn Glu Val
            20                  25                  30

Asp Ala Asp Gly Asn Gly Thr Ile Asp Phe Pro Glu Phe Leu Thr Met
        35                  40                  45

Met Ala Arg Lys Met Lys Asp Thr Asp Ser Glu Glu Glu Ile Arg Glu
    50                  55                  60

Ala Phe Arg Val Phe Asp Lys Asp Gly Asn Gly Tyr Ile Ser Ala Ala
65                  70                  75                  80

Glu Leu Arg His Val Met Thr Asn Leu Gly Glu Lys Leu Thr Asp Glu
                85                  90                  95

Glu Val Asp Glu Met Ile Arg Glu Ala Asp Ile Asp Gly Asp Gly Gln
            100                 105                 110

Val Asn Tyr Glu Glu Phe Val Gln Met Met Thr Ala Lys Gly Gly Ser
        115                 120                 125

Gly Ala Asp Gln Leu Thr Glu Glu Gln Ile Ala Glu Phe Lys Glu Ala
    130                 135                 140

Phe Ser Leu Phe Asp Lys Asp Gly
145                 150

<210> SEQ ID NO 85
<211> LENGTH: 152
<212> TYPE: PRT
<213> ORGANISM: artificial sequence
<220> FEATURE:
<223> OTHER INFORMATION: permutated calmodulin-variant: 40-S

<400> SEQUENCE: 85

Ser Leu Gly Gln Asn Pro Thr Glu Ala Glu Leu Gln Asp Met Ile Asn
1               5                   10                  15

Glu Val Asp Ala Asp Gly Asn Gly Thr Ile Asp Phe Pro Glu Phe Leu
            20                  25                  30

Thr Met Met Ala Arg Lys Met Lys Asp Thr Asp Ser Glu Glu Glu Ile
        35                  40                  45

Arg Glu Ala Phe Arg Val Phe Asp Lys Asp Gly Asn Gly Tyr Ile Ser
    50                  55                  60

Ala Ala Glu Leu Arg His Val Met Thr Asn Leu Gly Glu Lys Leu Thr
65                  70                  75                  80

Asp Glu Glu Val Asp Glu Met Ile Arg Glu Ala Asp Ile Asp Gly Asp
                85                  90                  95

Gly Gln Val Asn Tyr Glu Glu Phe Val Gln Met Met Thr Ala Lys Gly

Gly Ser Gly Ala Asp Gln Leu Thr Glu Glu Gln Ile Ala Glu Phe Lys
                100                 105                 110
Glu Ala Phe Ser Leu Phe Asp Lys Asp Gly Asp Gly Thr Ile Thr Thr
        115                 120                 125
Lys Glu Leu Gly Thr Val Met Arg
130                 135                 140

145                 150

<210> SEQ ID NO 86
<211> LENGTH: 152
<212> TYPE: PRT
<213> ORGANISM: artificial sequence
<220> FEATURE:
<223> OTHER INFORMATION: permutated calmodulin-variant: 45-P

<400> SEQUENCE: 86

Pro Thr Glu Ala Glu Leu Gln Asp Met Ile Asn Glu Val Asp Ala Asp
1               5                   10                  15
Gly Asn Gly Thr Ile Asp Phe Pro Glu Phe Leu Thr Met Met Ala Arg
                20                  25                  30
Lys Met Lys Asp Thr Asp Ser Glu Glu Glu Ile Arg Glu Ala Phe Arg
            35                  40                  45
Val Phe Asp Lys Asp Gly Asn Gly Tyr Ile Ser Ala Ala Glu Leu Arg
        50                  55                  60
His Val Met Thr Asn Leu Gly Glu Lys Leu Thr Asp Glu Glu Val Asp
65                  70                  75                  80
Glu Met Ile Arg Glu Ala Asp Ile Asp Gly Asp Gly Gln Val Asn Tyr
                85                  90                  95
Glu Glu Phe Val Gln Met Met Thr Ala Lys Gly Gly Ser Gly Ala Asp
                100                 105                 110
Gln Leu Thr Glu Glu Gln Ile Ala Glu Phe Lys Glu Ala Phe Ser Leu
        115                 120                 125
Phe Asp Lys Asp Gly Asp Gly Thr Ile Thr Thr Lys Glu Leu Gly Thr
    130                 135                 140
Val Met Arg Ser Leu Gly Gln Asn
145                 150

<210> SEQ ID NO 87
<211> LENGTH: 152
<212> TYPE: PRT
<213> ORGANISM: artificial sequence
<220> FEATURE:
<223> OTHER INFORMATION: permutated calmodulin-variant: 46-T

<400> SEQUENCE: 87

Thr Glu Ala Glu Leu Gln Asp Met Ile Asn Glu Val Asp Ala Asp Gly
1               5                   10                  15
Asn Gly Thr Ile Asp Phe Pro Glu Phe Leu Thr Met Met Ala Arg Lys
                20                  25                  30
Met Lys Asp Thr Asp Ser Glu Glu Glu Ile Arg Glu Ala Phe Arg Val
            35                  40                  45
Phe Asp Lys Asp Gly Asn Gly Tyr Ile Ser Ala Ala Glu Leu Arg His
        50                  55                  60
Val Met Thr Asn Leu Gly Glu Lys Leu Thr Asp Glu Glu Val Asp Glu
65                  70                  75                  80
Met Ile Arg Glu Ala Asp Ile Asp Gly Asp Gly Gln Val Asn Tyr Glu
                85                  90                  95

Glu Phe Val Gln Met Met Thr Ala Lys Gly Gly Ser Gly Ala Asp Gln
                100                 105                 110

Leu Thr Glu Glu Gln Ile Ala Glu Phe Lys Glu Ala Phe Ser Leu Phe
        115                 120                 125

Asp Lys Asp Gly Asp Gly Thr Ile Thr Thr Lys Glu Leu Gly Thr Val
        130                 135                 140

Met Arg Ser Leu Gly Gln Asn Pro
145                 150

<210> SEQ ID NO 88
<211> LENGTH: 152
<212> TYPE: PRT
<213> ORGANISM: artificial sequence
<220> FEATURE:
<223> OTHER INFORMATION: permutated calmodulin-variant: 56-E

<400> SEQUENCE: 88

Glu Val Asp Ala Asp Gly Asn Gly Thr Ile Asp Phe Pro Glu Phe Leu
1               5                   10                  15

Thr Met Met Ala Arg Lys Met Lys Asp Thr Asp Ser Glu Glu Glu Ile
                20                  25                  30

Arg Glu Ala Phe Arg Val Phe Asp Lys Asp Gly Asn Gly Tyr Ile Ser
            35                  40                  45

Ala Ala Glu Leu Arg His Val Met Thr Asn Leu Gly Glu Lys Leu Thr
50                  55                  60

Asp Glu Glu Val Asp Glu Met Ile Arg Glu Ala Asp Ile Asp Gly Asp
65                  70                  75                  80

Gly Gln Val Asn Tyr Glu Glu Phe Val Gln Met Met Thr Ala Lys Gly
                85                  90                  95

Gly Ser Gly Ala Asp Gln Leu Thr Glu Glu Gln Ile Ala Glu Phe Lys
                100                 105                 110

Glu Ala Phe Ser Leu Phe Asp Lys Asp Gly Asp Gly Thr Ile Thr Thr
            115                 120                 125

Lys Glu Leu Gly Thr Val Met Arg Ser Leu Gly Gln Asn Pro Thr Glu
        130                 135                 140

Ala Glu Leu Gln Asp Met Ile Asn
145                 150

<210> SEQ ID NO 89
<211> LENGTH: 152
<212> TYPE: PRT
<213> ORGANISM: artificial sequence
<220> FEATURE:
<223> OTHER INFORMATION: permutated calmodulin-variant: 59-A

<400> SEQUENCE: 89

Ala Asp Gly Asn Gly Thr Ile Asp Phe Pro Glu Phe Leu Thr Met Met
1               5                   10                  15

Ala Arg Lys Met Lys Asp Thr Asp Ser Glu Glu Glu Ile Arg Glu Ala
                20                  25                  30

Phe Arg Val Phe Asp Lys Asp Gly Asn Gly Tyr Ile Ser Ala Ala Glu
            35                  40                  45

Leu Arg His Val Met Thr Asn Leu Gly Glu Lys Leu Thr Asp Glu Glu
        50                  55                  60

Val Asp Glu Met Ile Arg Glu Ala Asp Ile Asp Gly Asp Gly Gln Val
65                  70                  75                  80

Asn Tyr Glu Glu Phe Val Gln Met Met Thr Ala Lys Gly Gly Ser Gly
                85                  90                  95

Ala Asp Gln Leu Thr Glu Glu Gln Ile Ala Glu Phe Lys Glu Ala Phe
                100                 105                 110

Ser Leu Phe Asp Lys Asp Gly Asp Gly Thr Ile Thr Thr Lys Glu Leu
            115                 120                 125

Gly Thr Val Met Arg Ser Leu Gly Gln Asn Pro Thr Glu Ala Glu Leu
130                 135                 140

Gln Asp Met Ile Asn Glu Val Asp
145                 150

<210> SEQ ID NO 90
<211> LENGTH: 152
<212> TYPE: PRT
<213> ORGANISM: artificial sequence
<220> FEATURE:
<223> OTHER INFORMATION: permutated calmodulin-variant: 60-D

<400> SEQUENCE: 90

Asp Gly Asn Gly Thr Ile Asp Phe Pro Glu Phe Leu Thr Met Met Ala
1               5                   10                  15

Arg Lys Met Lys Asp Thr Asp Ser Glu Glu Glu Ile Arg Glu Ala Phe
            20                  25                  30

Arg Val Phe Asp Lys Asp Gly Asn Gly Tyr Ile Ser Ala Ala Glu Leu
        35                  40                  45

Arg His Val Met Thr Asn Leu Gly Glu Lys Leu Thr Asp Glu Glu Val
    50                  55                  60

Asp Glu Met Ile Arg Glu Ala Asp Ile Asp Gly Asp Gly Gln Val Asn
65                  70                  75                  80

Tyr Glu Glu Phe Val Gln Met Met Thr Ala Lys Gly Gly Ser Gly Ala
                85                  90                  95

Asp Gln Leu Thr Glu Glu Gln Ile Ala Glu Phe Lys Glu Ala Phe Ser
            100                 105                 110

Leu Phe Asp Lys Asp Gly Asp Gly Thr Ile Thr Thr Lys Glu Leu Gly
        115                 120                 125

Thr Val Met Arg Ser Leu Gly Gln Asn Pro Thr Glu Ala Glu Leu Gln
    130                 135                 140

Asp Met Ile Asn Glu Val Asp Ala
145                 150

<210> SEQ ID NO 91
<211> LENGTH: 152
<212> TYPE: PRT
<213> ORGANISM: artificial sequence
<220> FEATURE:
<223> OTHER INFORMATION: permutated calmodulin-variant: 61-G

<400> SEQUENCE: 91

Gly Asn Gly Thr Ile Asp Phe Pro Glu Phe Leu Thr Met Met Ala Arg
1               5                   10                  15

Lys Met Lys Asp Thr Asp Ser Glu Glu Glu Ile Arg Glu Ala Phe Arg
            20                  25                  30

Val Phe Asp Lys Asp Gly Asn Gly Tyr Ile Ser Ala Ala Glu Leu Arg
        35                  40                  45

His Val Met Thr Asn Leu Gly Glu Lys Leu Thr Asp Glu Glu Val Asp
    50                  55                  60

Glu Met Ile Arg Glu Ala Asp Ile Asp Gly Asp Gly Gln Val Asn Tyr
65                  70                  75                  80

Glu Glu Phe Val Gln Met Met Thr Ala Lys Gly Gly Ser Gly Ala Asp

```
                85                  90                  95

Gln Leu Thr Glu Glu Gln Ile Ala Glu Phe Lys Glu Ala Phe Ser Leu
            100                 105                 110

Phe Asp Lys Asp Gly Asp Gly Thr Ile Thr Thr Lys Glu Leu Gly Thr
            115                 120                 125

Val Met Arg Ser Leu Gly Gln Asn Pro Thr Glu Ala Glu Leu Gln Asp
    130                 135                 140

Met Ile Asn Glu Val Asp Ala Asp
145                 150

<210> SEQ ID NO 92
<211> LENGTH: 152
<212> TYPE: PRT
<213> ORGANISM: artificial sequence
<220> FEATURE:
<223> OTHER INFORMATION: permutated calmodulin-variant: 62-N

<400> SEQUENCE: 92

Asn Gly Thr Ile Asp Phe Pro Glu Phe Leu Thr Met Met Ala Arg Lys
1               5                   10                  15

Met Lys Asp Thr Asp Ser Glu Glu Glu Ile Arg Glu Ala Phe Arg Val
            20                  25                  30

Phe Asp Lys Asp Gly Asn Gly Tyr Ile Ser Ala Ala Glu Leu Arg His
        35                  40                  45

Val Met Thr Asn Leu Gly Glu Lys Leu Thr Asp Glu Glu Val Asp Glu
    50                  55                  60

Met Ile Arg Glu Ala Asp Ile Asp Gly Asp Gly Gln Val Asn Tyr Glu
65                  70                  75                  80

Glu Phe Val Gln Met Met Thr Ala Lys Gly Gly Ser Gly Ala Asp Gln
                85                  90                  95

Leu Thr Glu Glu Gln Ile Ala Glu Phe Lys Glu Ala Phe Ser Leu Phe
            100                 105                 110

Asp Lys Asp Gly Asp Gly Thr Ile Thr Thr Lys Glu Leu Gly Thr Val
            115                 120                 125

Met Arg Ser Leu Gly Gln Asn Pro Thr Glu Ala Glu Leu Gln Asp Met
    130                 135                 140

Ile Asn Glu Val Asp Ala Asp Gly
145                 150

<210> SEQ ID NO 93
<211> LENGTH: 152
<212> TYPE: PRT
<213> ORGANISM: artificial sequence
<220> FEATURE:
<223> OTHER INFORMATION: permutated calmodulin-variant: 65-I

<400> SEQUENCE: 93

Ile Asp Phe Pro Glu Phe Leu Thr Met Met Ala Arg Lys Met Lys Asp
1               5                   10                  15

Thr Asp Ser Glu Glu Glu Ile Arg Glu Ala Phe Arg Val Phe Asp Lys
            20                  25                  30

Asp Gly Asn Gly Tyr Ile Ser Ala Ala Glu Leu Arg His Val Met Thr
        35                  40                  45

Asn Leu Gly Glu Lys Leu Thr Asp Glu Glu Val Asp Glu Met Ile Arg
    50                  55                  60

Glu Ala Asp Ile Asp Gly Asp Gly Gln Val Asn Tyr Glu Glu Phe Val
65                  70                  75                  80
```

```
Gln Met Met Thr Ala Lys Gly Gly Ser Gly Ala Asp Gln Leu Thr Glu
                85                  90                  95

Glu Gln Ile Ala Glu Phe Lys Glu Ala Phe Ser Leu Phe Asp Lys Asp
            100                 105                 110

Gly Asp Gly Thr Ile Thr Thr Lys Glu Leu Gly Thr Val Met Arg Ser
        115                 120                 125

Leu Gly Gln Asn Pro Thr Glu Ala Glu Leu Gln Asp Met Ile Asn Glu
    130                 135                 140

Val Asp Ala Asp Gly Asn Gly Thr
145                 150

<210> SEQ ID NO 94
<211> LENGTH: 152
<212> TYPE: PRT
<213> ORGANISM: artificial sequence
<220> FEATURE:
<223> OTHER INFORMATION: permutated calmodulin-variant: 75-A

<400> SEQUENCE: 94

Ala Arg Lys Met Lys Asp Thr Asp Ser Glu Glu Ile Arg Glu Ala
1               5                   10                  15

Phe Arg Val Phe Asp Lys Asp Gly Asn Gly Tyr Ile Ser Ala Ala Glu
            20                  25                  30

Leu Arg His Val Met Thr Asn Leu Gly Glu Lys Leu Thr Asp Glu Glu
        35                  40                  45

Val Asp Glu Met Ile Arg Glu Ala Asp Ile Asp Gly Asp Gly Gln Val
    50                  55                  60

Asn Tyr Glu Glu Phe Val Gln Met Met Thr Ala Lys Gly Gly Ser Gly
65                  70                  75                  80

Ala Asp Gln Leu Thr Glu Glu Gln Ile Ala Glu Phe Lys Glu Ala Phe
                85                  90                  95

Ser Leu Phe Asp Lys Asp Gly Asp Gly Thr Ile Thr Thr Lys Glu Leu
            100                 105                 110

Gly Thr Val Met Arg Ser Leu Gly Gln Asn Pro Thr Glu Ala Glu Leu
        115                 120                 125

Gln Asp Met Ile Asn Glu Val Asp Ala Asp Gly Asn Gly Thr Ile Asp
    130                 135                 140

Phe Pro Glu Phe Leu Thr Met Met
145                 150

<210> SEQ ID NO 95
<211> LENGTH: 152
<212> TYPE: PRT
<213> ORGANISM: artificial sequence
<220> FEATURE:
<223> OTHER INFORMATION: permutated calmodulin-variant: 76-R

<400> SEQUENCE: 95

Arg Lys Met Lys Asp Thr Asp Ser Glu Glu Ile Arg Glu Ala Phe
1               5                   10                  15

Arg Val Phe Asp Lys Asp Gly Asn Gly Tyr Ile Ser Ala Ala Glu Leu
            20                  25                  30

Arg His Val Met Thr Asn Leu Gly Glu Lys Leu Thr Asp Glu Glu Val
        35                  40                  45

Asp Glu Met Ile Arg Glu Ala Asp Ile Asp Gly Asp Gly Gln Val Asn
    50                  55                  60

Tyr Glu Glu Phe Val Gln Met Met Thr Ala Lys Gly Gly Ser Gly Ala
65                  70                  75                  80
```

Asp Gln Leu Thr Glu Glu Gln Ile Ala Glu Phe Lys Glu Ala Phe Ser
                85                  90                  95

Leu Phe Asp Lys Asp Gly Asp Gly Thr Ile Thr Thr Lys Glu Leu Gly
            100                 105                 110

Thr Val Met Arg Ser Leu Gly Gln Asn Pro Thr Glu Ala Glu Leu Gln
        115                 120                 125

Asp Met Ile Asn Glu Val Asp Ala Asp Gly Asn Gly Thr Ile Asp Phe
    130                 135                 140

Pro Glu Phe Leu Thr Met Met Ala
145             150

<210> SEQ ID NO 96
<211> LENGTH: 152
<212> TYPE: PRT
<213> ORGANISM: artificial sequence
<220> FEATURE:
<223> OTHER INFORMATION: permutated calmodulin-variant: 77-K

<400> SEQUENCE: 96

Lys Met Lys Asp Thr Asp Ser Glu Glu Glu Ile Arg Glu Ala Phe Arg
1               5                   10                  15

Val Phe Asp Lys Asp Gly Asn Gly Tyr Ile Ser Ala Ala Glu Leu Arg
            20                  25                  30

His Val Met Thr Asn Leu Gly Glu Lys Leu Thr Asp Glu Glu Val Asp
        35                  40                  45

Glu Met Ile Arg Glu Ala Asp Ile Asp Gly Asp Gly Gln Val Asn Tyr
    50                  55                  60

Glu Glu Phe Val Gln Met Met Thr Ala Lys Gly Gly Ser Gly Ala Asp
65                  70                  75                  80

Gln Leu Thr Glu Glu Gln Ile Ala Glu Phe Lys Glu Ala Phe Ser Leu
                85                  90                  95

Phe Asp Lys Asp Gly Asp Gly Thr Ile Thr Thr Lys Glu Leu Gly Thr
            100                 105                 110

Val Met Arg Ser Leu Gly Gln Asn Pro Thr Glu Ala Glu Leu Gln Asp
        115                 120                 125

Met Ile Asn Glu Val Asp Ala Asp Gly Asn Gly Thr Ile Asp Phe Pro
    130                 135                 140

Glu Phe Leu Thr Met Met Ala Arg
145             150

<210> SEQ ID NO 97
<211> LENGTH: 152
<212> TYPE: PRT
<213> ORGANISM: artificial sequence
<220> FEATURE:
<223> OTHER INFORMATION: permutated calmodulin-variant: 79-K

<400> SEQUENCE: 97

Lys Asp Thr Asp Ser Glu Glu Glu Ile Arg Glu Ala Phe Arg Val Phe
1               5                   10                  15

Asp Lys Asp Gly Asn Gly Tyr Ile Ser Ala Ala Glu Leu Arg His Val
            20                  25                  30

Met Thr Asn Leu Gly Glu Lys Leu Thr Asp Glu Glu Val Asp Glu Met
        35                  40                  45

Ile Arg Glu Ala Asp Ile Asp Gly Asp Gly Gln Val Asn Tyr Glu Glu
    50                  55                  60

Phe Val Gln Met Met Thr Ala Lys Gly Gly Ser Gly Ala Asp Gln Leu

```
                65                  70                  75                  80
Thr Glu Gln Ile Ala Glu Phe Lys Glu Ala Phe Ser Leu Phe Asp
                    85                  90                  95

Lys Asp Gly Asp Gly Thr Ile Thr Thr Lys Glu Leu Gly Thr Val Met
                100                 105                 110

Arg Ser Leu Gly Gln Asn Pro Thr Glu Ala Glu Leu Gln Asp Met Ile
            115                 120                 125

Asn Glu Val Asp Ala Asp Gly Asn Gly Thr Ile Asp Phe Pro Glu Phe
        130                 135                 140

Leu Thr Met Met Ala Arg Lys Met
145                 150

<210> SEQ ID NO 98
<211> LENGTH: 152
<212> TYPE: PRT
<213> ORGANISM: artificial sequence
<220> FEATURE:
<223> OTHER INFORMATION: permutated calmodulin-variant: 80-D

<400> SEQUENCE: 98

Asp Thr Asp Ser Glu Glu Glu Ile Arg Glu Ala Phe Arg Val Phe Asp
1               5                   10                  15

Lys Asp Gly Asn Gly Tyr Ile Ser Ala Ala Glu Leu Arg His Val Met
                20                  25                  30

Thr Asn Leu Gly Glu Lys Leu Thr Asp Glu Glu Val Asp Glu Met Ile
            35                  40                  45

Arg Glu Ala Asp Ile Asp Gly Asp Gly Gln Val Asn Tyr Glu Glu Phe
        50                  55                  60

Val Gln Met Met Thr Ala Lys Gly Gly Ser Gly Ala Asp Gln Leu Thr
65                  70                  75                  80

Glu Glu Gln Ile Ala Glu Phe Lys Glu Ala Phe Ser Leu Phe Asp Lys
                85                  90                  95

Asp Gly Asp Gly Thr Ile Thr Thr Lys Glu Leu Gly Thr Val Met Arg
                100                 105                 110

Ser Leu Gly Gln Asn Pro Thr Glu Ala Glu Leu Gln Asp Met Ile Asn
            115                 120                 125

Glu Val Asp Ala Asp Gly Asn Gly Thr Ile Asp Phe Pro Glu Phe Leu
        130                 135                 140

Thr Met Met Ala Arg Lys Met Lys
145                 150

<210> SEQ ID NO 99
<211> LENGTH: 152
<212> TYPE: PRT
<213> ORGANISM: artificial sequence
<220> FEATURE:
<223> OTHER INFORMATION: permutated calmodulin-variant: 81-T

<400> SEQUENCE: 99

Thr Asp Ser Glu Glu Glu Ile Arg Glu Ala Phe Arg Val Phe Asp Lys
1               5                   10                  15

Asp Gly Asn Gly Tyr Ile Ser Ala Ala Glu Leu Arg His Val Met Thr
                20                  25                  30

Asn Leu Gly Glu Lys Leu Thr Asp Glu Glu Val Asp Glu Met Ile Arg
            35                  40                  45

Glu Ala Asp Ile Asp Gly Asp Gly Gln Val Asn Tyr Glu Glu Phe Val
        50                  55                  60
```

```
Gln Met Met Thr Ala Lys Gly Gly Ser Gly Ala Asp Gln Leu Thr Glu
 65                  70                  75                  80

Glu Gln Ile Ala Glu Phe Lys Glu Ala Phe Ser Leu Phe Asp Lys Asp
                 85                  90                  95

Gly Asp Gly Thr Ile Thr Thr Lys Glu Leu Gly Thr Val Met Arg Ser
            100                 105                 110

Leu Gly Gln Asn Pro Thr Glu Ala Glu Leu Gln Asp Met Ile Asn Glu
        115                 120                 125

Val Asp Ala Asp Gly Asn Gly Thr Ile Asp Phe Pro Glu Phe Leu Thr
    130                 135                 140

Met Met Ala Arg Lys Met Lys Asp
145                 150
```

<210> SEQ ID NO 100
<211> LENGTH: 152
<212> TYPE: PRT
<213> ORGANISM: artificial sequence
<220> FEATURE:
<223> OTHER INFORMATION: permutated calmodulin-variant: 82-D

<400> SEQUENCE: 100

```
Asp Ser Glu Glu Glu Ile Arg Glu Ala Phe Arg Val Phe Asp Lys Asp
  1               5                  10                  15

Gly Asn Gly Tyr Ile Ser Ala Ala Glu Leu Arg His Val Met Thr Asn
             20                  25                  30

Leu Gly Glu Lys Leu Thr Asp Glu Glu Val Asp Glu Met Ile Arg Glu
         35                  40                  45

Ala Asp Ile Asp Gly Asp Gly Gln Val Asn Tyr Glu Glu Phe Val Gln
 50                  55                  60

Met Met Thr Ala Lys Gly Gly Ser Gly Ala Asp Gln Leu Thr Glu Glu
 65                  70                  75                  80

Gln Ile Ala Glu Phe Lys Glu Ala Phe Ser Leu Phe Asp Lys Asp Gly
                 85                  90                  95

Asp Gly Thr Ile Thr Thr Lys Glu Leu Gly Thr Val Met Arg Ser Leu
            100                 105                 110

Gly Gln Asn Pro Thr Glu Ala Glu Leu Gln Asp Met Ile Asn Glu Val
        115                 120                 125

Asp Ala Asp Gly Asn Gly Thr Ile Asp Phe Pro Glu Phe Leu Thr Met
    130                 135                 140

Met Ala Arg Lys Met Lys Asp Thr
145                 150
```

<210> SEQ ID NO 101
<211> LENGTH: 152
<212> TYPE: PRT
<213> ORGANISM: artificial sequence
<220> FEATURE:
<223> OTHER INFORMATION: permutated calmodulin-variant: 85-E

<400> SEQUENCE: 101

```
Glu Glu Ile Arg Glu Ala Phe Arg Val Phe Asp Lys Asp Gly Asn Gly
  1               5                  10                  15

Tyr Ile Ser Ala Ala Glu Leu Arg His Val Met Thr Asn Leu Gly Glu
             20                  25                  30

Lys Leu Thr Asp Glu Glu Val Asp Glu Met Ile Arg Glu Ala Asp Ile
         35                  40                  45

Asp Gly Asp Gly Gln Val Asn Tyr Glu Glu Phe Val Gln Met Met Thr
 50                  55                  60
```

Ala Lys Gly Gly Ser Gly Ala Asp Gln Leu Thr Glu Gln Ile Ala
65                  70                  75                  80

Glu Phe Lys Glu Ala Phe Ser Leu Phe Asp Lys Asp Gly Asp Gly Thr
                85                  90                  95

Ile Thr Thr Lys Glu Leu Gly Thr Val Met Arg Ser Leu Gly Gln Asn
            100                 105                 110

Pro Thr Glu Ala Glu Leu Gln Asp Met Ile Asn Glu Val Asp Ala Asp
                115                 120                 125

Gly Asn Gly Thr Ile Asp Phe Pro Glu Phe Leu Thr Met Met Ala Arg
130                 135                 140

Lys Met Lys Asp Thr Asp Ser Glu
145                 150

<210> SEQ ID NO 102
<211> LENGTH: 152
<212> TYPE: PRT
<213> ORGANISM: artificial sequence
<220> FEATURE:
<223> OTHER INFORMATION: permutated calmodulin-variant: 98-G

<400> SEQUENCE: 102

Gly Asn Gly Tyr Ile Ser Ala Ala Glu Leu Arg His Val Met Thr Asn
1               5                   10                  15

Leu Gly Glu Lys Leu Thr Asp Glu Glu Val Asp Glu Met Ile Arg Glu
            20                  25                  30

Ala Asp Ile Asp Gly Asp Gly Gln Val Asn Tyr Glu Glu Phe Val Gln
        35                  40                  45

Met Met Thr Ala Lys Gly Gly Ser Gly Ala Asp Gln Leu Thr Glu Glu
    50                  55                  60

Gln Ile Ala Glu Phe Lys Glu Ala Phe Ser Leu Phe Asp Lys Asp Gly
65                  70                  75                  80

Asp Gly Thr Ile Thr Thr Lys Glu Leu Gly Thr Val Met Arg Ser Leu
                85                  90                  95

Gly Gln Asn Pro Thr Glu Ala Glu Leu Gln Asp Met Ile Asn Glu Val
            100                 105                 110

Asp Ala Asp Gly Asn Gly Thr Ile Asp Phe Pro Glu Phe Leu Thr Met
        115                 120                 125

Met Ala Arg Lys Met Lys Asp Thr Asp Ser Glu Glu Glu Ile Arg Glu
    130                 135                 140

Ala Phe Arg Val Phe Asp Lys Asp
145                 150

<210> SEQ ID NO 103
<211> LENGTH: 152
<212> TYPE: PRT
<213> ORGANISM: artificial sequence
<220> FEATURE:
<223> OTHER INFORMATION: permutated calmodulin-variant: 99-N

<400> SEQUENCE: 103

Asn Gly Tyr Ile Ser Ala Ala Glu Leu Arg His Val Met Thr Asn Leu
1               5                   10                  15

Gly Glu Lys Leu Thr Asp Glu Glu Val Asp Glu Met Ile Arg Glu Ala
            20                  25                  30

Asp Ile Asp Gly Asp Gly Gln Val Asn Tyr Glu Glu Phe Val Gln Met
        35                  40                  45

Met Thr Ala Lys Gly Gly Ser Gly Ala Asp Gln Leu Thr Glu Glu Gln

```
                    50                  55                  60
Ile Ala Glu Phe Lys Glu Ala Phe Ser Leu Phe Asp Lys Asp Gly Asp
 65                  70                  75                  80

Gly Thr Ile Thr Thr Lys Glu Leu Gly Thr Val Met Arg Ser Leu Gly
                     85                  90                  95

Gln Asn Pro Thr Glu Ala Glu Leu Gln Asp Met Ile Asn Glu Val Asp
                    100                 105                 110

Ala Asp Gly Asn Gly Thr Ile Asp Phe Pro Glu Phe Leu Thr Met Met
                115                 120                 125

Ala Arg Lys Met Lys Asp Thr Asp Ser Glu Glu Glu Ile Arg Glu Ala
            130                 135                 140

Phe Arg Val Phe Asp Lys Asp Gly
145                 150

<210> SEQ ID NO 104
<211> LENGTH: 152
<212> TYPE: PRT
<213> ORGANISM: artificial sequence
<220> FEATURE:
<223> OTHER INFORMATION: permutated calmodulin-variant: 103-S

<400> SEQUENCE: 104

Ser Ala Ala Glu Leu Arg His Val Met Thr Asn Leu Gly Glu Lys Leu
 1               5                  10                  15

Thr Asp Glu Glu Val Asp Glu Met Ile Arg Glu Ala Asp Ile Asp Gly
                    20                  25                  30

Asp Gly Gln Val Asn Tyr Glu Glu Phe Val Gln Met Met Thr Ala Lys
                35                  40                  45

Gly Gly Ser Gly Ala Asp Gln Leu Thr Glu Glu Gln Ile Ala Glu Phe
             50                  55                  60

Lys Glu Ala Phe Ser Leu Phe Asp Lys Asp Gly Asp Gly Thr Ile Thr
 65                  70                  75                  80

Thr Lys Glu Leu Gly Thr Val Met Arg Ser Leu Gly Gln Asn Pro Thr
                    85                  90                  95

Glu Ala Glu Leu Gln Asp Met Ile Asn Glu Val Asp Ala Asp Gly Asn
                100                 105                 110

Gly Thr Ile Asp Phe Pro Glu Phe Leu Thr Met Met Ala Arg Lys Met
            115                 120                 125

Lys Asp Thr Asp Ser Glu Glu Glu Ile Arg Glu Ala Phe Arg Val Phe
        130                 135                 140

Asp Lys Asp Gly Asn Gly Tyr Ile
145                 150

<210> SEQ ID NO 105
<211> LENGTH: 152
<212> TYPE: PRT
<213> ORGANISM: artificial sequence
<220> FEATURE:
<223> OTHER INFORMATION: permutated calmodulin-variant: 104-A

<400> SEQUENCE: 105

Ala Ala Glu Leu Arg His Val Met Thr Asn Leu Gly Glu Lys Leu Thr
 1               5                  10                  15

Asp Glu Glu Val Asp Glu Met Ile Arg Glu Ala Asp Ile Asp Gly Asp
                    20                  25                  30

Gly Gln Val Asn Tyr Glu Glu Phe Val Gln Met Met Thr Ala Lys Gly
                35                  40                  45
```

Gly Ser Gly Ala Asp Gln Leu Thr Glu Glu Gln Ile Ala Glu Phe Lys
        50                  55                  60

Glu Ala Phe Ser Leu Phe Asp Lys Asp Gly Asp Gly Thr Ile Thr Thr
65                  70                  75                  80

Lys Glu Leu Gly Thr Val Met Arg Ser Leu Gly Gln Asn Pro Thr Glu
                85                  90                  95

Ala Glu Leu Gln Asp Met Ile Asn Glu Val Asp Ala Asp Gly Asn Gly
                100                 105                 110

Thr Ile Asp Phe Pro Glu Phe Leu Thr Met Met Ala Arg Lys Met Lys
                115                 120                 125

Asp Thr Asp Ser Glu Glu Glu Ile Arg Glu Ala Phe Arg Val Phe Asp
        130                 135                 140

Lys Asp Gly Asn Gly Tyr Ile Ser
145                 150

<210> SEQ ID NO 106
<211> LENGTH: 152
<212> TYPE: PRT
<213> ORGANISM: artificial sequence
<220> FEATURE:
<223> OTHER INFORMATION: permutated calmodulin-variant: 110-V

<400> SEQUENCE: 106

Val Met Thr Asn Leu Gly Glu Lys Leu Thr Asp Glu Glu Val Asp Glu
1               5                   10                  15

Met Ile Arg Glu Ala Asp Ile Asp Gly Asp Gly Gln Val Asn Tyr Glu
                20                  25                  30

Glu Phe Val Gln Met Met Thr Ala Lys Gly Gly Ser Gly Ala Asp Gln
                35                  40                  45

Leu Thr Glu Glu Gln Ile Ala Glu Phe Lys Glu Ala Phe Ser Leu Phe
        50                  55                  60

Asp Lys Asp Gly Asp Gly Thr Ile Thr Thr Lys Glu Leu Gly Thr Val
65                  70                  75                  80

Met Arg Ser Leu Gly Gln Asn Pro Thr Glu Ala Glu Leu Gln Asp Met
                85                  90                  95

Ile Asn Glu Val Asp Ala Asp Gly Asn Gly Thr Ile Asp Phe Pro Glu
                100                 105                 110

Phe Leu Thr Met Met Ala Arg Lys Met Lys Asp Thr Asp Ser Glu Glu
                115                 120                 125

Glu Ile Arg Glu Ala Phe Arg Val Phe Asp Lys Asp Gly Asn Gly Tyr
        130                 135                 140

Ile Ser Ala Ala Glu Leu Arg His
145                 150

<210> SEQ ID NO 107
<211> LENGTH: 152
<212> TYPE: PRT
<213> ORGANISM: artificial sequence
<220> FEATURE:
<223> OTHER INFORMATION: permutated calmodulin-variant: 111-M

<400> SEQUENCE: 107

Met Thr Asn Leu Gly Glu Lys Leu Thr Asp Glu Glu Val Asp Glu Met
1               5                   10                  15

Ile Arg Glu Ala Asp Ile Asp Gly Asp Gly Gln Val Asn Tyr Glu Glu
                20                  25                  30

Phe Val Gln Met Met Thr Ala Lys Gly Gly Ser Gly Ala Asp Gln Leu
                35                  40                  45

Thr Glu Glu Gln Ile Ala Glu Phe Lys Glu Ala Phe Ser Leu Phe Asp
            50                  55                  60

Lys Asp Gly Asp Gly Thr Ile Thr Thr Lys Glu Leu Gly Thr Val Met
 65                  70                  75                  80

Arg Ser Leu Gly Gln Asn Pro Thr Glu Ala Glu Leu Gln Asp Met Ile
                85                  90                  95

Asn Glu Val Asp Ala Asp Gly Asn Gly Thr Ile Asp Phe Pro Glu Phe
                100                 105                 110

Leu Thr Met Met Ala Arg Lys Met Lys Asp Thr Asp Ser Glu Glu Glu
            115                 120                 125

Ile Arg Glu Ala Phe Arg Val Phe Asp Lys Asp Gly Asn Gly Tyr Ile
130                 135                 140

Ser Ala Ala Glu Leu Arg His Val
145                 150

<210> SEQ ID NO 108
<211> LENGTH: 152
<212> TYPE: PRT
<213> ORGANISM: artificial sequence
<220> FEATURE:
<223> OTHER INFORMATION: permutated calmodulin-variant: 112-T

<400> SEQUENCE: 108

Thr Asn Leu Gly Glu Lys Leu Thr Asp Glu Glu Val Asp Glu Met Ile
 1               5                  10                  15

Arg Glu Ala Asp Ile Asp Gly Asp Gly Gln Val Asn Tyr Glu Glu Phe
                20                  25                  30

Val Gln Met Met Thr Ala Lys Gly Gly Ser Gly Ala Asp Gln Leu Thr
            35                  40                  45

Glu Glu Gln Ile Ala Glu Phe Lys Glu Ala Phe Ser Leu Phe Asp Lys
        50                  55                  60

Asp Gly Asp Gly Thr Ile Thr Thr Lys Glu Leu Gly Thr Val Met Arg
 65                  70                  75                  80

Ser Leu Gly Gln Asn Pro Thr Glu Ala Glu Leu Gln Asp Met Ile Asn
                85                  90                  95

Glu Val Asp Ala Asp Gly Asn Gly Thr Ile Asp Phe Pro Glu Phe Leu
                100                 105                 110

Thr Met Met Ala Arg Lys Met Lys Asp Thr Asp Ser Glu Glu Glu Ile
            115                 120                 125

Arg Glu Ala Phe Arg Val Phe Asp Lys Asp Gly Asn Gly Tyr Ile Ser
        130                 135                 140

Ala Ala Glu Leu Arg His Val Met
145                 150

<210> SEQ ID NO 109
<211> LENGTH: 152
<212> TYPE: PRT
<213> ORGANISM: artificial sequence
<220> FEATURE:
<223> OTHER INFORMATION: permutated calmodulin-variant: 113-N

<400> SEQUENCE: 109

Asn Leu Gly Glu Lys Leu Thr Asp Glu Glu Val Asp Glu Met Ile Arg
 1               5                  10                  15

Glu Ala Asp Ile Asp Gly Asp Gly Gln Val Asn Tyr Glu Glu Phe Val
                20                  25                  30

Gln Met Met Thr Ala Lys Gly Gly Ser Gly Ala Asp Gln Leu Thr Glu

```
                35                  40                  45
Glu Gln Ile Ala Glu Phe Lys Glu Ala Phe Ser Leu Phe Asp Lys Asp
         50                  55                  60
Gly Asp Gly Thr Ile Thr Thr Lys Glu Leu Gly Thr Val Met Arg Ser
 65                  70                  75                  80
Leu Gly Gln Asn Pro Thr Glu Ala Glu Leu Gln Asp Met Ile Asn Glu
                 85                  90                  95
Val Asp Ala Asp Gly Asn Gly Thr Ile Asp Phe Pro Glu Phe Leu Thr
            100                 105                 110
Met Met Ala Arg Lys Met Lys Asp Thr Asp Ser Glu Glu Glu Ile Arg
        115                 120                 125
Glu Ala Phe Arg Val Phe Asp Lys Asp Gly Asn Gly Tyr Ile Ser Ala
    130                 135                 140
Ala Glu Leu Arg His Val Met Thr
145                 150

<210> SEQ ID NO 110
<211> LENGTH: 152
<212> TYPE: PRT
<213> ORGANISM: artificial sequence
<220> FEATURE:
<223> OTHER INFORMATION: permutated calmodulin-variant: 117-K

<400> SEQUENCE: 110

Lys Leu Thr Asp Glu Glu Val Asp Glu Met Ile Arg Glu Ala Asp Ile
1               5                   10                  15
Asp Gly Asp Gly Gln Val Asn Tyr Glu Glu Phe Val Gln Met Met Thr
            20                  25                  30
Ala Lys Gly Gly Ser Gly Ala Asp Gln Leu Thr Glu Glu Gln Ile Ala
        35                  40                  45
Glu Phe Lys Glu Ala Phe Ser Leu Phe Asp Lys Asp Gly Asp Gly Thr
    50                  55                  60
Ile Thr Thr Lys Glu Leu Gly Thr Val Met Arg Ser Leu Gly Gln Asn
 65                 70                  75                  80
Pro Thr Glu Ala Glu Leu Gln Asp Met Ile Asn Glu Val Asp Ala Asp
                85                  90                  95
Gly Asn Gly Thr Ile Asp Phe Pro Glu Phe Leu Thr Met Met Ala Arg
            100                 105                 110
Lys Met Lys Asp Thr Asp Ser Glu Glu Glu Ile Arg Glu Ala Phe Arg
        115                 120                 125
Val Phe Asp Lys Asp Gly Asn Gly Tyr Ile Ser Ala Ala Glu Leu Arg
    130                 135                 140
His Val Met Thr Asn Leu Gly Glu
145                 150

<210> SEQ ID NO 111
<211> LENGTH: 152
<212> TYPE: PRT
<213> ORGANISM: artificial sequence
<220> FEATURE:
<223> OTHER INFORMATION: permutated calmodulin-variant: 118-L

<400> SEQUENCE: 111

Leu Thr Asp Glu Glu Val Asp Glu Met Ile Arg Glu Ala Asp Ile Asp
1               5                   10                  15
Gly Asp Gly Gln Val Asn Tyr Glu Glu Phe Val Gln Met Met Thr Ala
            20                  25                  30
```

```
Lys Gly Gly Ser Gly Ala Asp Gln Leu Thr Glu Gln Ile Ala Glu
            35                  40                  45

Phe Lys Glu Ala Phe Ser Leu Phe Asp Lys Asp Gly Asp Gly Thr Ile
 50                  55                  60

Thr Thr Lys Glu Leu Gly Thr Val Met Arg Ser Leu Gly Gln Asn Pro
 65                  70                  75                  80

Thr Glu Ala Glu Leu Gln Asp Met Ile Asn Glu Val Asp Ala Asp Gly
                 85                  90                  95

Asn Gly Thr Ile Asp Phe Pro Glu Phe Leu Thr Met Met Ala Arg Lys
            100                 105                 110

Met Lys Asp Thr Asp Ser Glu Glu Glu Ile Arg Glu Ala Phe Arg Val
            115                 120                 125

Phe Asp Lys Asp Gly Asn Gly Tyr Ile Ser Ala Ala Glu Leu Arg His
130                 135                 140

Val Met Thr Asn Leu Gly Glu Lys
145                 150
```

<210> SEQ ID NO 112
<211> LENGTH: 152
<212> TYPE: PRT
<213> ORGANISM: artificial sequence
<220> FEATURE:
<223> OTHER INFORMATION: permutated calmodulin-variant: 119-T

<400> SEQUENCE: 112

```
Thr Asp Glu Glu Val Asp Glu Met Ile Arg Glu Ala Asp Ile Asp Gly
 1               5                  10                  15

Asp Gly Gln Val Asn Tyr Glu Glu Phe Val Gln Met Met Thr Ala Lys
                 20                  25                  30

Gly Gly Ser Gly Ala Asp Gln Leu Thr Glu Gln Ile Ala Glu Phe
            35                  40                  45

Lys Glu Ala Phe Ser Leu Phe Asp Lys Asp Gly Asp Gly Thr Ile Thr
 50                  55                  60

Thr Lys Glu Leu Gly Thr Val Met Arg Ser Leu Gly Gln Asn Pro Thr
 65                  70                  75                  80

Glu Ala Glu Leu Gln Asp Met Ile Asn Glu Val Asp Ala Asp Gly Asn
                 85                  90                  95

Gly Thr Ile Asp Phe Pro Glu Phe Leu Thr Met Met Ala Arg Lys Met
            100                 105                 110

Lys Asp Thr Asp Ser Glu Glu Glu Ile Arg Glu Ala Phe Arg Val Phe
            115                 120                 125

Asp Lys Asp Gly Asn Gly Tyr Ile Ser Ala Ala Glu Leu Arg His Val
130                 135                 140

Met Thr Asn Leu Gly Glu Lys Leu
145                 150
```

<210> SEQ ID NO 113
<211> LENGTH: 152
<212> TYPE: PRT
<213> ORGANISM: artificial sequence
<220> FEATURE:
<223> OTHER INFORMATION: permutated calmodulin-variant: 120-D

<400> SEQUENCE: 113

```
Asp Glu Glu Val Asp Glu Met Ile Arg Glu Ala Asp Ile Asp Gly Asp
 1               5                  10                  15

Gly Gln Val Asn Tyr Glu Glu Phe Val Gln Met Met Thr Ala Lys Gly
                 20                  25                  30
```

```
Gly Ser Gly Ala Asp Gln Leu Thr Glu Glu Gln Ile Ala Glu Phe Lys
        35                  40                  45

Glu Ala Phe Ser Leu Phe Asp Lys Asp Gly Asp Gly Thr Ile Thr Thr
 50                  55                  60

Lys Glu Leu Gly Thr Val Met Arg Ser Leu Gly Gln Asn Pro Thr Glu
 65                  70                  75                  80

Ala Glu Leu Gln Asp Met Ile Asn Glu Val Asp Ala Asp Gly Asn Gly
                 85                  90                  95

Thr Ile Asp Phe Pro Glu Phe Leu Thr Met Met Ala Arg Lys Met Lys
                100                 105                 110

Asp Thr Asp Ser Glu Glu Glu Ile Arg Glu Ala Phe Arg Val Phe Asp
                115                 120                 125

Lys Asp Gly Asn Gly Tyr Ile Ser Ala Ala Glu Leu Arg His Val Met
            130                 135                 140

Thr Asn Leu Gly Glu Lys Leu Thr
145                 150

<210> SEQ ID NO 114
<211> LENGTH: 152
<212> TYPE: PRT
<213> ORGANISM: artificial sequence
<220> FEATURE:
<223> OTHER INFORMATION: permutated calmodulin-variant: 123-V

<400> SEQUENCE: 114

Val Asp Glu Met Ile Arg Glu Ala Asp Ile Asp Gly Asp Gly Gln Val
 1               5                  10                  15

Asn Tyr Glu Glu Phe Val Gln Met Met Thr Ala Lys Gly Gly Ser Gly
                 20                  25                  30

Ala Asp Gln Leu Thr Glu Glu Gln Ile Ala Glu Phe Lys Glu Ala Phe
             35                  40                  45

Ser Leu Phe Asp Lys Asp Gly Asp Gly Thr Ile Thr Thr Lys Glu Leu
 50                  55                  60

Gly Thr Val Met Arg Ser Leu Gly Gln Asn Pro Thr Glu Ala Glu Leu
 65                  70                  75                  80

Gln Asp Met Ile Asn Glu Val Asp Ala Asp Gly Asn Gly Thr Ile Asp
                 85                  90                  95

Phe Pro Glu Phe Leu Thr Met Met Ala Arg Lys Met Lys Asp Thr Asp
                100                 105                 110

Ser Glu Glu Glu Ile Arg Glu Ala Phe Arg Val Phe Asp Lys Asp Gly
            115                 120                 125

Asn Gly Tyr Ile Ser Ala Ala Glu Leu Arg His Val Met Thr Asn Leu
        130                 135                 140

Gly Glu Lys Leu Thr Asp Glu Glu
145                 150

<210> SEQ ID NO 115
<211> LENGTH: 152
<212> TYPE: PRT
<213> ORGANISM: artificial sequence
<220> FEATURE:
<223> OTHER INFORMATION: permutated calmodulin-variant: 124-D

<400> SEQUENCE: 115

Asp Glu Met Ile Arg Glu Ala Asp Ile Asp Gly Asp Gly Gln Val Asn
 1               5                  10                  15

Tyr Glu Glu Phe Val Gln Met Met Thr Ala Lys Gly Gly Ser Gly Ala
```

```
                 20                  25                  30

Asp Gln Leu Thr Glu Glu Gln Ile Ala Glu Phe Lys Glu Ala Phe Ser
         35                  40                  45

Leu Phe Asp Lys Asp Gly Asp Gly Thr Ile Thr Thr Lys Glu Leu Gly
 50                  55                  60

Thr Val Met Arg Ser Leu Gly Gln Asn Pro Thr Glu Ala Glu Leu Gln
 65                  70                  75                  80

Asp Met Ile Asn Glu Val Asp Ala Asp Gly Asn Gly Thr Ile Asp Phe
                 85                  90                  95

Pro Glu Phe Leu Thr Met Met Ala Arg Lys Met Lys Asp Thr Asp Ser
             100                 105                 110

Glu Glu Glu Ile Arg Glu Ala Phe Arg Val Phe Asp Lys Asp Gly Asn
         115                 120                 125

Gly Tyr Ile Ser Ala Ala Glu Leu Arg His Val Met Thr Asn Leu Gly
     130                 135                 140

Glu Lys Leu Thr Asp Glu Glu Val
145                 150

<210> SEQ ID NO 116
<211> LENGTH: 152
<212> TYPE: PRT
<213> ORGANISM: artificial sequence
<220> FEATURE:
<223> OTHER INFORMATION: permutated calmodulin-variant: 125-E

<400> SEQUENCE: 116

Glu Met Ile Arg Glu Ala Asp Ile Asp Gly Asp Gly Gln Val Asn Tyr
 1               5                  10                  15

Glu Glu Phe Val Gln Met Met Thr Ala Lys Gly Gly Ser Gly Ala Asp
                 20                  25                  30

Gln Leu Thr Glu Glu Gln Ile Ala Glu Phe Lys Glu Ala Phe Ser Leu
         35                  40                  45

Phe Asp Lys Asp Gly Asp Gly Thr Ile Thr Thr Lys Glu Leu Gly Thr
 50                  55                  60

Val Met Arg Ser Leu Gly Gln Asn Pro Thr Glu Ala Glu Leu Gln Asp
 65                  70                  75                  80

Met Ile Asn Glu Val Asp Ala Asp Gly Asn Gly Thr Ile Asp Phe Pro
                 85                  90                  95

Glu Phe Leu Thr Met Met Ala Arg Lys Met Lys Asp Thr Asp Ser Glu
             100                 105                 110

Glu Glu Ile Arg Glu Ala Phe Arg Val Phe Asp Lys Asp Gly Asn Gly
         115                 120                 125

Tyr Ile Ser Ala Ala Glu Leu Arg His Val Met Thr Asn Leu Gly Glu
     130                 135                 140

Lys Leu Thr Asp Glu Glu Val Asp
145                 150

<210> SEQ ID NO 117
<211> LENGTH: 152
<212> TYPE: PRT
<213> ORGANISM: artificial sequence
<220> FEATURE:
<223> OTHER INFORMATION: permutated calmodulin-variant: 130-A

<400> SEQUENCE: 117

Ala Asp Ile Asp Gly Asp Gly Gln Val Asn Tyr Glu Glu Phe Val Gln
 1               5                  10                  15
```

Met Met Thr Ala Lys Gly Gly Ser Gly Ala Asp Gln Leu Thr Glu Glu
            20                  25                  30

Gln Ile Ala Glu Phe Lys Glu Ala Phe Ser Leu Phe Asp Lys Asp Gly
        35                  40                  45

Asp Gly Thr Ile Thr Thr Lys Glu Leu Gly Thr Val Met Arg Ser Leu
 50                  55                  60

Gly Gln Asn Pro Thr Glu Ala Glu Leu Gln Asp Met Ile Asn Glu Val
 65                  70                  75                  80

Asp Ala Asp Gly Asn Gly Thr Ile Asp Phe Pro Glu Phe Leu Thr Met
                85                  90                  95

Met Ala Arg Lys Met Lys Asp Thr Asp Ser Glu Glu Glu Ile Arg Glu
            100                 105                 110

Ala Phe Arg Val Phe Asp Lys Asp Gly Asn Gly Tyr Ile Ser Ala Ala
        115                 120                 125

Glu Leu Arg His Val Met Thr Asn Leu Gly Glu Lys Leu Thr Asp Glu
130                 135                 140

Glu Val Asp Glu Met Ile Arg Glu
145                 150

<210> SEQ ID NO 118
<211> LENGTH: 152
<212> TYPE: PRT
<213> ORGANISM: artificial sequence
<220> FEATURE:
<223> OTHER INFORMATION: permutated calmodulin-variant: 134-G

<400> SEQUENCE: 118

Gly Asp Gly Gln Val Asn Tyr Glu Glu Phe Val Gln Met Met Thr Ala
1               5                   10                  15

Lys Gly Gly Ser Gly Ala Asp Gln Leu Thr Glu Glu Gln Ile Ala Glu
            20                  25                  30

Phe Lys Glu Ala Phe Ser Leu Phe Asp Lys Asp Gly Asp Gly Thr Ile
        35                  40                  45

Thr Thr Lys Glu Leu Gly Thr Val Met Arg Ser Leu Gly Gln Asn Pro
 50                  55                  60

Thr Glu Ala Glu Leu Gln Asp Met Ile Asn Glu Val Asp Ala Asp Gly
 65                  70                  75                  80

Asn Gly Thr Ile Asp Phe Pro Glu Phe Leu Thr Met Met Ala Arg Lys
                85                  90                  95

Met Lys Asp Thr Asp Ser Glu Glu Glu Ile Arg Glu Ala Phe Arg Val
            100                 105                 110

Phe Asp Lys Asp Gly Asn Gly Tyr Ile Ser Ala Ala Glu Leu Arg His
        115                 120                 125

Val Met Thr Asn Leu Gly Glu Lys Leu Thr Asp Glu Glu Val Asp Glu
130                 135                 140

Met Ile Arg Glu Ala Asp Ile Asp
145                 150

<210> SEQ ID NO 119
<211> LENGTH: 152
<212> TYPE: PRT
<213> ORGANISM: artificial sequence
<220> FEATURE:
<223> OTHER INFORMATION: permutated calmodulin-variant: 135-D

<400> SEQUENCE: 119

Asp Gly Gln Val Asn Tyr Glu Glu Phe Val Gln Met Met Thr Ala Lys
1               5                   10                  15

```
Gly Gly Ser Gly Ala Asp Gln Leu Thr Glu Glu Gln Ile Ala Glu Phe
            20                  25                  30

Lys Glu Ala Phe Ser Leu Phe Asp Lys Asp Gly Asp Gly Thr Ile Thr
        35                  40                  45

Thr Lys Glu Leu Gly Thr Val Met Arg Ser Leu Gly Gln Asn Pro Thr
 50                  55                  60

Glu Ala Glu Leu Gln Asp Met Ile Asn Glu Val Asp Ala Asp Gly Asn
 65                  70                  75                  80

Gly Thr Ile Asp Phe Pro Glu Phe Leu Thr Met Met Ala Arg Lys Met
                85                  90                  95

Lys Asp Thr Asp Ser Glu Glu Glu Ile Arg Glu Ala Phe Arg Val Phe
            100                 105                 110

Asp Lys Asp Gly Asn Gly Tyr Ile Ser Ala Ala Glu Leu Arg His Val
            115                 120                 125

Met Thr Asn Leu Gly Glu Lys Leu Thr Asp Glu Glu Val Asp Glu Met
130                 135                 140

Ile Arg Glu Ala Asp Ile Asp Gly
145                 150
```

<210> SEQ ID NO 120
<211> LENGTH: 152
<212> TYPE: PRT
<213> ORGANISM: artificial sequence
<220> FEATURE:
<223> OTHER INFORMATION: permutated calmodulin-variant: 144-V

<400> SEQUENCE: 120

```
Val Gln Met Met Thr Ala Lys Gly Gly Ser Gly Ala Asp Gln Leu Thr
 1               5                  10                  15

Glu Glu Gln Ile Ala Glu Phe Lys Glu Ala Phe Ser Leu Phe Asp Lys
            20                  25                  30

Asp Gly Asp Gly Thr Ile Thr Thr Lys Glu Leu Gly Thr Val Met Arg
        35                  40                  45

Ser Leu Gly Gln Asn Pro Thr Glu Ala Glu Leu Gln Asp Met Ile Asn
 50                  55                  60

Glu Val Asp Ala Asp Gly Asn Gly Thr Ile Asp Phe Pro Glu Phe Leu
 65                  70                  75                  80

Thr Met Met Ala Arg Lys Met Lys Asp Thr Asp Ser Glu Glu Glu Ile
                85                  90                  95

Arg Glu Ala Phe Arg Val Phe Asp Lys Asp Gly Asn Gly Tyr Ile Ser
            100                 105                 110

Ala Ala Glu Leu Arg His Val Met Thr Asn Leu Gly Glu Lys Leu Thr
            115                 120                 125

Asp Glu Glu Val Asp Glu Met Ile Arg Glu Ala Asp Ile Asp Gly Asp
        130                 135                 140

Gly Gln Val Asn Tyr Glu Glu Phe
145                 150
```

<210> SEQ ID NO 121
<211> LENGTH: 152
<212> TYPE: PRT
<213> ORGANISM: artificial sequence
<220> FEATURE:
<223> OTHER INFORMATION: permutated calmodulin-variant: 148-T

<400> SEQUENCE: 121

Thr Ala Lys Gly Gly Ser Gly Ala Asp Gln Leu Thr Glu Glu Gln Ile

```
                1               5                    10                   15
            Ala Glu Phe Lys Glu Ala Phe Ser Leu Phe Asp Lys Asp Gly Asp Gly
                           20                   25                   30

Thr Ile Thr Thr Lys Glu Leu Gly Thr Val Met Arg Ser Leu Gly Gln
                           35                   40                   45

Asn Pro Thr Glu Ala Glu Leu Gln Asp Met Ile Asn Glu Val Asp Ala
                           50                   55                   60

Asp Gly Asn Gly Thr Ile Asp Phe Pro Glu Phe Leu Thr Met Met Ala
            65                      70                   75                   80

Arg Lys Met Lys Asp Thr Asp Ser Glu Glu Glu Ile Arg Glu Ala Phe
                                85                   90                   95

Arg Val Phe Asp Lys Asp Gly Asn Gly Tyr Ile Ser Ala Ala Glu Leu
                                100                  105                  110

Arg His Val Met Thr Asn Leu Gly Glu Lys Leu Thr Asp Glu Glu Val
                           115                  120                  125

Asp Glu Met Ile Arg Glu Ala Asp Ile Asp Gly Asp Gly Gln Val Asn
                           130                  135                  140

Tyr Glu Glu Phe Val Gln Met Met
            145                 150

<210> SEQ ID NO 122
<211> LENGTH: 152
<212> TYPE: PRT
<213> ORGANISM: artificial sequence
<220> FEATURE:
<223> OTHER INFORMATION: permutated calmodulin-variant: 151-G

<400> SEQUENCE: 122

Gly Gly Ser Gly Ala Asp Gln Leu Thr Glu Glu Gln Ile Ala Glu Phe
1               5                   10                  15

Lys Glu Ala Phe Ser Leu Phe Asp Lys Asp Gly Asp Gly Thr Ile Thr
                20                  25                  30

Thr Lys Glu Leu Gly Thr Val Met Arg Ser Leu Gly Gln Asn Pro Thr
            35                  40                  45

Glu Ala Glu Leu Gln Asp Met Ile Asn Glu Val Asp Ala Asp Gly Asn
        50                  55                  60

Gly Thr Ile Asp Phe Pro Glu Phe Leu Thr Met Met Ala Arg Lys Met
65                  70                  75                  80

Lys Asp Thr Asp Ser Glu Glu Glu Ile Arg Glu Ala Phe Arg Val Phe
                85                  90                  95

Asp Lys Asp Gly Asn Gly Tyr Ile Ser Ala Ala Glu Leu Arg His Val
            100                 105                 110

Met Thr Asn Leu Gly Glu Lys Leu Thr Asp Glu Glu Val Asp Glu Met
        115                 120                 125

Ile Arg Glu Ala Asp Ile Asp Gly Asp Gly Gln Val Asn Tyr Glu Glu
    130                 135                 140

Phe Val Gln Met Met Thr Ala Lys
145                 150

<210> SEQ ID NO 123
<211> LENGTH: 152
<212> TYPE: PRT
<213> ORGANISM: artificial sequence
<220> FEATURE:
<223> OTHER INFORMATION: permutated calmodulin-variant: 152-G

<400> SEQUENCE: 123
```

Gly Ser Gly Ala Asp Gln Leu Thr Glu Glu Gln Ile Ala Glu Phe Lys
1               5                   10                  15

Glu Ala Phe Ser Leu Phe Asp Lys Asp Gly Asp Gly Thr Ile Thr Thr
                20                  25                  30

Lys Glu Leu Gly Thr Val Met Arg Ser Leu Gly Gln Asn Pro Thr Glu
            35                  40                  45

Ala Glu Leu Gln Asp Met Ile Asn Glu Val Asp Ala Asp Gly Asn Gly
        50                  55                  60

Thr Ile Asp Phe Pro Glu Phe Leu Thr Met Met Ala Arg Lys Met Lys
65                  70                  75                  80

Asp Thr Asp Ser Glu Glu Glu Ile Arg Glu Ala Phe Arg Val Phe Asp
                85                  90                  95

Lys Asp Gly Asn Gly Tyr Ile Ser Ala Ala Glu Leu Arg His Val Met
                100                 105                 110

Thr Asn Leu Gly Glu Lys Leu Thr Asp Glu Glu Val Asp Glu Met Ile
            115                 120                 125

Arg Glu Ala Asp Ile Asp Gly Asp Gly Gln Val Asn Tyr Glu Glu Phe
        130                 135                 140

Val Gln Met Met Thr Ala Lys Gly
145                 150

<210> SEQ ID NO 124
<211> LENGTH: 409
<212> TYPE: PRT
<213> ORGANISM: artificial sequence
<220> FEATURE:
<223> OTHER INFORMATION: anti-CD14 scFv (TUEK4)_M-1

<400> SEQUENCE: 124

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Phe Asn Asp Gly Thr Lys Phe Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Ala Asp Ser Ala Val Tyr Tyr Cys
                85                  90                  95

Ala Arg Glu Asp Asp Tyr Tyr Ala Met Asp Tyr Trp Gly Gln Gly
                100                 105                 110

Thr Ser Val Thr Val Ser Ser Ala Ser Met Lys Asp Thr Asp Ser Glu
            115                 120                 125

Glu Glu Ile Arg Glu Ala Phe Arg Val Phe Asp Lys Asp Gly Asn Gly
        130                 135                 140

Tyr Ile Ser Ala Ala Glu Leu Arg His Val Met Thr Asn Leu Gly Glu
145                 150                 155                 160

Lys Leu Thr Asp Glu Glu Val Asp Glu Met Ile Arg Glu Ala Asp Ile
                165                 170                 175

Asp Gly Asp Gly Gln Val Asn Tyr Glu Glu Phe Val Gln Met Met Thr
            180                 185                 190

Ala Lys Gly Gly Ser Gly Ala Asp Gln Leu Thr Glu Glu Gln Ile Ala
        195                 200                 205

-continued

```
Glu Phe Lys Glu Ala Phe Ser Leu Phe Asp Lys Asp Gly Asp Gly Thr
            210                 215                 220
Ile Thr Thr Lys Glu Leu Gly Thr Val Met Arg Ser Leu Gly Gln Asn
225                 230                 235                 240
Pro Thr Glu Ala Glu Leu Gln Asp Met Ile Asn Glu Val Asp Ala Asp
                245                 250                 255
Gly Asn Gly Thr Ile Asp Phe Pro Glu Phe Leu Thr Met Met Ala Arg
            260                 265                 270
Lys Asp Ile Val Leu Thr Gln Ser Pro Ala Ser Leu Ala Val Ser Leu
                275                 280                 285
Gly Gln Arg Ala Thr Ile Ser Cys Arg Ala Ser Glu Ser Val Asp Asn
290                 295                 300
Tyr Gly Ile Ser Phe Met Asn Trp Phe Gln Gln Lys Pro Gly Gln Pro
305                 310                 315                 320
Pro Arg Leu Leu Ile Leu Ala Ala Ser Asn Gln Gly Ser Gly Val Pro
                325                 330                 335
Ala Arg Phe Ser Gly Ser Gly Ser Gly Thr Asp Phe Ser Leu Asn Ile
            340                 345                 350
His Pro Met Glu Glu Asp Asp Thr Ala Met Tyr Phe Cys Gln Gln Ser
                355                 360                 365
Lys Glu Val Pro Trp Thr Phe Gly Gly Gly Thr Lys Leu Glu Ile Lys
370                 375                 380
Arg Thr Ala Ala Ala His His His His His Ser Ser Gly Gly Gly
385                 390                 395                 400
Arg Gly Ser His His His His His
            405
```

<210> SEQ ID NO 125
<211> LENGTH: 409
<212> TYPE: PRT
<213> ORGANISM: artificial sequence
<220> FEATURE:
<223> OTHER INFORMATION: anti-CD14 scFv (TUEK4)_M-2

<400> SEQUENCE: 125

```
Glu Val Gln Leu Gln Gln Ser Gly Pro Glu Leu Val Lys Pro Gly Ala
1               5                   10                  15
Ser Val Lys Met Ser Cys Lys Ala Ser Gly Tyr Thr Phe Thr Ser Tyr
            20                  25                  30
Val Met His Trp Val Lys Gln Lys Pro Gly Gln Gly Leu Glu Trp Ile
        35                  40                  45
Gly Tyr Ile Asn Pro Phe Asn Asp Gly Thr Lys Phe Asn Glu Lys Phe
    50                  55                  60
Lys Gly Lys Ala Thr Leu Thr Ser Asp Lys Ser Ser Ser Thr Ala Tyr
65                  70                  75                  80
Met Glu Leu Ser Ser Leu Thr Ser Ala Asp Ser Ala Val Tyr Tyr Cys
                85                  90                  95
Ala Arg Glu Asp Asp Tyr Tyr Ala Met Asp Tyr Trp Gly Gln Gly
            100                 105                 110
Thr Ser Val Thr Val Ser Ser Ala Ser Ser Glu Glu Glu Ile Arg Glu
        115                 120                 125
Ala Phe Arg Val Phe Asp Lys Asp Gly Asn Gly Tyr Ile Ser Ala Ala
    130                 135                 140
Glu Leu Arg His Val Met Thr Asn Leu Gly Glu Lys Leu Thr Asp Glu
145                 150                 155                 160
```

```
Glu Val Asp Glu Met Ile Arg Glu Ala Asp Ile Asp Gly Asp Gly Gln
                165                 170                 175

Val Asn Tyr Glu Glu Phe Val Gln Met Met Thr Ala Lys Gly Gly Ser
            180                 185                 190

Gly Ala Asp Gln Leu Thr Glu Glu Gln Ile Ala Glu Phe Lys Glu Ala
        195                 200                 205

Phe Ser Leu Phe Asp Lys Asp Gly Asp Gly Thr Ile Thr Thr Lys Glu
    210                 215                 220

Leu Gly Thr Val Met Arg Ser Leu Gly Gln Asn Pro Thr Glu Ala Glu
225                 230                 235                 240

Leu Gln Asp Met Ile Asn Glu Val Asp Ala Asp Gly Asn Gly Thr Ile
                245                 250                 255

Asp Phe Pro Glu Phe Leu Thr Met Met Ala Arg Lys Met Lys Asp Thr
            260                 265                 270

Asp Asp Ile Val Leu Thr Gln Ser Pro Ala Ser Leu Ala Val Ser Leu
        275                 280                 285

Gly Gln Arg Ala Thr Ile Ser Cys Arg Ala Ser Glu Ser Val Asp Asn
    290                 295                 300

Tyr Gly Ile Ser Phe Met Asn Trp Phe Gln Gln Lys Pro Gly Gln Pro
305                 310                 315                 320

Pro Arg Leu Leu Ile Leu Ala Ala Ser Asn Gln Gly Ser Gly Val Pro
                325                 330                 335

Ala Arg Phe Ser Gly Ser Gly Ser Gly Thr Asp Phe Ser Leu Asn Ile
            340                 345                 350

His Pro Met Glu Glu Asp Asp Thr Ala Met Tyr Phe Cys Gln Gln Ser
        355                 360                 365

Lys Glu Val Pro Trp Thr Phe Gly Gly Gly Thr Lys Leu Glu Ile Lys
    370                 375                 380

Arg Thr Ala Ala Ala His His His His His Ser Ser Gly Gly
385                 390                 395                 400

Arg Gly Ser His His His His His
                405

<210> SEQ ID NO 126
<211> LENGTH: 409
<212> TYPE: PRT
<213> ORGANISM: artificial sequence
<220> FEATURE:
<223> OTHER INFORMATION: anti-CD14 scFv (TUEK4)_C-1

<400> SEQUENCE: 126

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Phe Asn Asp Gly Thr Lys Phe Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Ala Asp Ser Ala Val Tyr Tyr Cys
                85                  90                  95

Ala Arg Glu Asp Asp Tyr Tyr Ala Met Asp Tyr Trp Gly Gln Gly
            100                 105                 110
```

Thr Ser Val Thr Val Ser Ser Ala Ser Lys Gly Gly Ser Gly Ala Asp
            115                 120                 125

Gln Leu Thr Glu Glu Gln Ile Ala Glu Phe Lys Glu Ala Phe Ser Leu
    130                 135                 140

Phe Asp Lys Asp Gly Asp Gly Thr Ile Thr Thr Lys Glu Leu Gly Thr
145                 150                 155                 160

Val Met Arg Ser Leu Gly Gln Asn Pro Thr Glu Ala Glu Leu Gln Asp
                165                 170                 175

Met Ile Asn Glu Val Asp Ala Asp Gly Asn Gly Thr Ile Asp Phe Pro
                180                 185                 190

Glu Phe Leu Thr Met Met Ala Arg Lys Met Lys Asp Thr Asp Ser Glu
            195                 200                 205

Glu Glu Ile Arg Glu Ala Phe Arg Val Phe Asp Lys Asp Gly Asn Gly
        210                 215                 220

Tyr Ile Ser Ala Ala Glu Leu Arg His Val Met Thr Asn Leu Gly Glu
225                 230                 235                 240

Lys Leu Thr Asp Glu Glu Val Asp Glu Met Ile Arg Glu Ala Asp Ile
                245                 250                 255

Asp Gly Asp Gly Gln Val Asn Tyr Glu Glu Phe Val Gln Met Met Thr
                260                 265                 270

Ala Asp Ile Val Leu Thr Gln Ser Pro Ala Ser Leu Ala Val Ser Leu
            275                 280                 285

Gly Gln Arg Ala Thr Ile Ser Cys Arg Ala Ser Glu Ser Val Asp Asn
        290                 295                 300

Tyr Gly Ile Ser Phe Met Asn Trp Phe Gln Gln Lys Pro Gly Gln Pro
305                 310                 315                 320

Pro Arg Leu Leu Ile Leu Ala Ala Ser Asn Gln Gly Ser Gly Val Pro
                325                 330                 335

Ala Arg Phe Ser Gly Ser Gly Ser Gly Thr Asp Phe Ser Leu Asn Ile
            340                 345                 350

His Pro Met Glu Glu Asp Asp Thr Ala Met Tyr Phe Cys Gln Gln Ser
        355                 360                 365

Lys Glu Val Pro Trp Thr Phe Gly Gly Gly Thr Lys Leu Glu Ile Lys
370                 375                 380

Arg Thr Ala Ala Ala His His His His His His Ser Ser Gly Gly Gly
385                 390                 395                 400

Arg Gly Ser His His His His His His
                405

<210> SEQ ID NO 127
<211> LENGTH: 409
<212> TYPE: PRT
<213> ORGANISM: artificial sequence
<220> FEATURE:
<223> OTHER INFORMATION: anti-CD14 scFv (TUEK4)_C-2

<400> SEQUENCE: 127

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Phe Asn Asp Gly Thr Lys Phe Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Ala Asp Ser Ala Val Tyr Tyr Cys
                85                  90                  95

Ala Arg Glu Asp Asp Tyr Tyr Tyr Ala Met Asp Tyr Trp Gly Gln Gly
            100                 105                 110

Thr Ser Val Thr Val Ser Ser Ala Ser Ala Lys Gly Gly Ser Gly Ala
        115                 120                 125

Asp Gln Leu Thr Glu Glu Gln Ile Ala Glu Phe Lys Glu Ala Phe Ser
    130                 135                 140

Leu Phe Asp Lys Asp Gly Asp Gly Thr Ile Thr Thr Lys Glu Leu Gly
145                 150                 155                 160

Thr Val Met Arg Ser Leu Gly Gln Asn Pro Thr Glu Ala Glu Leu Gln
                165                 170                 175

Asp Met Ile Asn Glu Val Asp Ala Asp Gly Asn Gly Thr Ile Asp Phe
            180                 185                 190

Pro Glu Phe Leu Thr Met Met Ala Arg Lys Met Lys Asp Thr Asp Ser
        195                 200                 205

Glu Glu Glu Ile Arg Glu Ala Phe Arg Val Phe Asp Lys Asp Gly Asn
    210                 215                 220

Gly Tyr Ile Ser Ala Ala Glu Leu Arg His Val Met Thr Asn Leu Gly
225                 230                 235                 240

Glu Lys Leu Thr Asp Glu Glu Val Asp Glu Met Ile Arg Glu Ala Asp
                245                 250                 255

Ile Asp Gly Asp Gly Gln Val Asn Tyr Glu Glu Phe Val Gln Met Met
            260                 265                 270

Thr Asp Ile Val Leu Thr Gln Ser Pro Ala Ser Leu Ala Val Ser Leu
        275                 280                 285

Gly Gln Arg Ala Thr Ile Ser Cys Arg Ala Ser Glu Ser Val Asp Asn
    290                 295                 300

Tyr Gly Ile Ser Phe Met Asn Trp Phe Gln Gln Lys Pro Gly Gln Pro
305                 310                 315                 320

Pro Arg Leu Leu Ile Leu Ala Ala Ser Asn Gln Gly Ser Gly Val Pro
                325                 330                 335

Ala Arg Phe Ser Gly Ser Gly Ser Gly Thr Asp Phe Ser Leu Asn Ile
            340                 345                 350

His Pro Met Glu Glu Asp Asp Thr Ala Met Tyr Phe Cys Gln Gln Ser
        355                 360                 365

Lys Glu Val Pro Trp Thr Phe Gly Gly Gly Thr Lys Leu Glu Ile Lys
    370                 375                 380

Arg Thr Ala Ala Ala His His His His His Ser Ser Gly Gly Gly
385                 390                 395                 400

Arg Gly Ser His His His His His His
                405

<210> SEQ ID NO 128
<211> LENGTH: 413
<212> TYPE: PRT
<213> ORGANISM: artificial sequence
<220> FEATURE:
<223> OTHER INFORMATION: anti-Biotin scFv (18E7.2)_M-1

<400> SEQUENCE: 128

Glu Val Gln Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Asn Tyr
            20                  25                  30

Ala Met Ser Trp Val Arg Gln Thr Pro Glu Thr Arg Leu Asn Trp Val
        35                  40                  45

Ala Thr Ile Thr Gly Gly Ser Tyr Thr Tyr Tyr Pro Asp Ser Val
    50                  55                  60

Lys Gly Arg Phe Thr Ile Ser Arg Asp Asn Ala Lys Asp Thr Leu Tyr
65                  70                  75                  80

Leu Gln Met Ser Ser Leu Arg Ser Glu Asp Thr Ala Met Tyr Tyr Cys
            85                  90                  95

Val Arg Gln Arg Val Gly Asp Tyr Val Ser Ser Leu Leu Gly Tyr Trp
        100                 105                 110

Gly Gln Gly Thr Leu Val Thr Val Ser Ala Ala Ser Met Lys Asp Thr
    115                 120                 125

Asp Ser Glu Glu Glu Ile Arg Glu Ala Phe Arg Val Phe Asp Lys Asp
    130                 135                 140

Gly Asn Gly Tyr Ile Ser Ala Ala Glu Leu Arg His Val Met Thr Asn
145                 150                 155                 160

Leu Gly Glu Lys Leu Thr Asp Glu Glu Val Asp Glu Met Ile Arg Glu
                165                 170                 175

Ala Asp Ile Asp Gly Asp Gly Gln Val Asn Tyr Glu Glu Phe Val Gln
            180                 185                 190

Met Met Thr Ala Lys Gly Gly Ser Gly Ala Asp Gln Leu Thr Glu Glu
        195                 200                 205

Gln Ile Ala Glu Phe Lys Glu Ala Phe Ser Leu Phe Asp Lys Asp Gly
    210                 215                 220

Asp Gly Thr Ile Thr Thr Lys Glu Leu Gly Thr Val Met Arg Ser Leu
225                 230                 235                 240

Gly Gln Asn Pro Thr Glu Ala Glu Leu Gln Asp Met Ile Asn Glu Val
                245                 250                 255

Asp Ala Asp Gly Asn Gly Thr Ile Asp Phe Pro Glu Phe Leu Thr Met
            260                 265                 270

Met Ala Arg Lys Asp Ile Asp Val Val Met Thr Gln Thr Pro Leu Ser
        275                 280                 285

Leu Pro Val Ser Leu Gly Asp Gln Ala Ser Ile Ser Cys Arg Ser Ser
    290                 295                 300

Gln Ser Leu Val His Ser Asn Gly Asn Thr Tyr Leu His Trp Phe Leu
305                 310                 315                 320

Gln Lys Pro Gly Gln Ser Pro Asn Leu Leu Ile Tyr Lys Val Ser Asn
                325                 330                 335

Arg Phe Ser Gly Val Pro Asp Arg Phe Ser Gly Ser Gly Ser Gly Thr
            340                 345                 350

Asp Phe Thr Leu Lys Ile Ser Arg Val Glu Ala Glu Asp Leu Gly Val
        355                 360                 365

Tyr Phe Cys Ser Gln Ser Thr His Val Pro Tyr Thr Phe Gly Gly Gly
    370                 375                 380

Thr Lys Leu Glu Ile Lys Ala Ala Ala His His His His His His Ser
385                 390                 395                 400

Ser Gly Gly Gly Arg Gly Ser His His His His His
            405                 410

<210> SEQ ID NO 129
<211> LENGTH: 413
<212> TYPE: PRT

<213> ORGANISM: artificial sequence
<220> FEATURE:
<223> OTHER INFORMATION: anti-Biotin scFv (18E7.2)_M-2

<400> SEQUENCE: 129

Glu Val Gln Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Asn Tyr
            20                  25                  30

Ala Met Ser Trp Val Arg Gln Thr Pro Glu Thr Arg Leu Asn Trp Val
        35                  40                  45

Ala Thr Ile Thr Gly Gly Ser Tyr Thr Tyr Tyr Pro Asp Ser Val
    50                  55                  60

Lys Gly Arg Phe Thr Ile Ser Arg Asp Asn Ala Lys Asp Thr Leu Tyr
65                  70                  75                  80

Leu Gln Met Ser Ser Leu Arg Ser Glu Asp Thr Ala Met Tyr Tyr Cys
                85                  90                  95

Val Arg Gln Arg Val Gly Asp Tyr Val Ser Ser Leu Leu Gly Tyr Trp
            100                 105                 110

Gly Gln Gly Thr Leu Val Thr Val Ser Ala Ala Ser Ser Glu Glu Glu
        115                 120                 125

Ile Arg Glu Ala Phe Arg Val Phe Asp Lys Asp Gly Asn Gly Tyr Ile
    130                 135                 140

Ser Ala Ala Glu Leu Arg His Val Met Thr Asn Leu Gly Glu Lys Leu
145                 150                 155                 160

Thr Asp Glu Glu Val Asp Glu Met Ile Arg Glu Ala Asp Ile Asp Gly
                165                 170                 175

Asp Gly Gln Val Asn Tyr Glu Glu Phe Val Gln Met Met Thr Ala Lys
            180                 185                 190

Gly Gly Ser Gly Ala Asp Gln Leu Thr Glu Glu Gln Ile Ala Glu Phe
        195                 200                 205

Lys Glu Ala Phe Ser Leu Phe Asp Lys Asp Gly Asp Gly Thr Ile Thr
    210                 215                 220

Thr Lys Glu Leu Gly Thr Val Met Arg Ser Leu Gly Gln Asn Pro Thr
225                 230                 235                 240

Glu Ala Glu Leu Gln Asp Met Ile Asn Glu Val Asp Ala Asp Gly Asn
                245                 250                 255

Gly Thr Ile Asp Phe Pro Glu Phe Leu Thr Met Met Ala Arg Lys Met
            260                 265                 270

Lys Asp Thr Asp Ser Asp Ile Asp Val Val Met Thr Gln Thr Pro Leu Ser
    275                 280                 285

Leu Pro Val Ser Leu Gly Asp Gln Ala Ser Ile Ser Cys Arg Ser Ser
290                 295                 300

Gln Ser Leu Val His Ser Asn Gly Asn Thr Tyr Leu His Trp Phe Leu
305                 310                 315                 320

Gln Lys Pro Gly Gln Ser Pro Asn Leu Leu Ile Tyr Lys Val Ser Asn
                325                 330                 335

Arg Phe Ser Gly Val Pro Asp Arg Phe Ser Gly Ser Gly Ser Gly Thr
            340                 345                 350

Asp Phe Thr Leu Lys Ile Ser Arg Val Glu Ala Glu Asp Leu Gly Val
        355                 360                 365

Tyr Phe Cys Ser Gln Ser Thr His Val Pro Tyr Thr Phe Gly Gly Gly
    370                 375                 380

Thr Lys Leu Glu Ile Lys Ala Ala Ala His His His His His His Ser

```
                385                 390                 395                 400
Ser Gly Gly Gly Arg Gly Ser His His His His His
                    405                 410

<210> SEQ ID NO 130
<211> LENGTH: 413
<212> TYPE: PRT
<213> ORGANISM: artificial sequence
<220> FEATURE:
<223> OTHER INFORMATION: anti-Biotin scFv (18E7.2)_C-1

<400> SEQUENCE: 130

Glu Val Gln Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Asn Tyr
            20                  25                  30

Ala Met Ser Trp Val Arg Gln Thr Pro Glu Thr Arg Leu Asn Trp Val
        35                  40                  45

Ala Thr Ile Thr Gly Gly Ser Tyr Thr Tyr Tyr Pro Asp Ser Val
    50                  55                  60

Lys Gly Arg Phe Thr Ile Ser Arg Asp Asn Ala Lys Asp Thr Leu Tyr
65                  70                  75                  80

Leu Gln Met Ser Ser Leu Arg Ser Glu Asp Thr Ala Met Tyr Tyr Cys
                85                  90                  95

Val Arg Gln Arg Val Gly Asp Tyr Val Ser Ser Leu Leu Gly Tyr Trp
            100                 105                 110

Gly Gln Gly Thr Leu Val Thr Val Ser Ala Ala Ser Lys Gly Gly Ser
        115                 120                 125

Gly Ala Asp Gln Leu Thr Glu Glu Gln Ile Ala Glu Phe Lys Glu Ala
    130                 135                 140

Phe Ser Leu Phe Asp Lys Asp Gly Asp Gly Thr Ile Thr Thr Lys Glu
145                 150                 155                 160

Leu Gly Thr Val Met Arg Ser Leu Gly Gln Asn Pro Thr Glu Ala Glu
                165                 170                 175

Leu Gln Asp Met Ile Asn Glu Val Asp Ala Asp Gly Asn Gly Thr Ile
            180                 185                 190

Asp Phe Pro Glu Phe Leu Thr Met Met Ala Arg Lys Met Lys Asp Thr
        195                 200                 205

Asp Ser Glu Glu Glu Ile Arg Glu Ala Phe Arg Val Phe Asp Lys Asp
    210                 215                 220

Gly Asn Gly Tyr Ile Ser Ala Ala Glu Leu Arg His Val Met Thr Asn
225                 230                 235                 240

Leu Gly Glu Lys Leu Thr Asp Glu Glu Val Asp Glu Met Ile Arg Glu
                245                 250                 255

Ala Asp Ile Asp Gly Asp Gly Gln Val Asn Tyr Glu Glu Phe Val Gln
            260                 265                 270

Met Met Thr Ala Asp Ile Asp Val Val Met Thr Gln Thr Pro Leu Ser
        275                 280                 285

Leu Pro Val Ser Leu Gly Asp Gln Ala Ser Ile Ser Cys Arg Ser Ser
    290                 295                 300

Gln Ser Leu Val His Ser Asn Gly Asn Thr Tyr Leu His Trp Phe Leu
305                 310                 315                 320

Gln Lys Pro Gly Gln Ser Pro Asn Leu Leu Ile Tyr Lys Val Ser Asn
                325                 330                 335

Arg Phe Ser Gly Val Pro Asp Arg Phe Ser Gly Ser Gly Ser Gly Thr
```

```
            340                 345                 350
Asp Phe Thr Leu Lys Ile Ser Arg Val Glu Ala Glu Asp Leu Gly Val
            355                 360                 365

Tyr Phe Cys Ser Gln Ser Thr His Val Pro Tyr Thr Phe Gly Gly Gly
            370                 375                 380

Thr Lys Leu Glu Ile Lys Ala Ala Ala His His His His His His Ser
385                 390                 395                 400

Ser Gly Gly Gly Arg Gly Ser His His His His His His
            405                 410
```

<210> SEQ ID NO 131
<211> LENGTH: 406
<212> TYPE: PRT
<213> ORGANISM: artificial sequence
<220> FEATURE:
<223> OTHER INFORMATION: anti-CD4 scFv (Q425)_M-1

<400> SEQUENCE: 131

```
Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Gly Leu Glu Trp Val
        35                  40                  45

Ala Thr Ile Ser Ser Gly Gly Ser Tyr Thr Tyr Tyr Pro Asp Asn Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95

Ala Arg His Glu Asp Gly Asn Trp Asn Tyr Phe Asp Tyr Trp Gly Gln
        100                 105                 110

Gly Thr Thr Leu Thr Val Ser Ser Ala Ser Met Lys Asp Thr Asp Ser
    115                 120                 125

Glu Glu Glu Ile Arg Glu Ala Phe Arg Val Phe Asp Lys Asp Gly Asn
130                 135                 140

Gly Tyr Ile Ser Ala Ala Glu Leu Arg His Val Met Thr Asn Leu Gly
145                 150                 155                 160

Glu Lys Leu Thr Asp Glu Glu Val Asp Glu Met Ile Arg Glu Ala Asp
            165                 170                 175

Ile Asp Gly Asp Gly Gln Val Asn Tyr Glu Glu Phe Val Gln Met Met
        180                 185                 190

Thr Ala Lys Gly Gly Ser Gly Ala Asp Gln Leu Thr Glu Glu Gln Ile
    195                 200                 205

Ala Glu Phe Lys Glu Ala Phe Ser Leu Phe Asp Lys Asp Gly Asp Gly
210                 215                 220

Thr Ile Thr Thr Lys Glu Leu Gly Thr Val Met Arg Ser Leu Gly Gln
225                 230                 235                 240

Asn Pro Thr Glu Ala Glu Leu Gln Asp Met Ile Asn Glu Val Asp Ala
            245                 250                 255

Asp Gly Asn Gly Thr Ile Asp Phe Pro Glu Phe Leu Thr Met Met Ala
        260                 265                 270

Arg Lys Asp Ile Glu Thr Thr Val Thr Gln Ser Pro Ala Ser Leu Ser
    275                 280                 285

Val Ala Ile Gly Glu Lys Val Thr Ile Arg Cys Ile Thr Ser Thr Asp
```

```
                290                 295                 300
Ile Asp Asp Met Asn Trp Tyr Gln Gln Lys Pro Gly Glu Pro Pro
305                 310                 315                 320

Lys Phe Phe Ile Ser Glu Gly Asn Thr Leu Arg Pro Gly Val Pro Ser
                325                 330                 335

Arg Phe Ser Ser Ser Gly Tyr Gly Thr Asp Phe Val Phe Thr Ile Glu
                340                 345                 350

Asn Met Leu Ser Glu Asp Val Ala Asp Tyr Tyr Cys Leu Gln Ser Asp
                355                 360                 365

Thr Leu Pro Leu Thr Phe Gly Ser Gly Thr Lys Leu Glu Ile Lys Ala
                370                 375                 380

Ala Ala His His His His His His Ser Ser Gly Gly Arg Gly Ser
385                 390                 395                 400

His His His His His His
                405

<210> SEQ ID NO 132
<211> LENGTH: 406
<212> TYPE: PRT
<213> ORGANISM: artificial sequence
<220> FEATURE:
<223> OTHER INFORMATION: anti-CD4 scFv (Q425)_M-2

<400> SEQUENCE: 132

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Asp Lys Gly Leu Glu Trp Val
                35                  40                  45

Ala Thr Ile Ser Ser Gly Gly Ser Tyr Thr Tyr Tyr Pro Asp Asn Val
            50                  55                  60

Lys Gly Arg Phe Thr Ile Ser Arg Asp Asn Ala Lys Asn Thr Leu Tyr
65              70                  75                  80

Leu Gln Met Ser Ser Leu Lys Ser Glu Asp Thr Ala Met Tyr Tyr Cys
                85                  90                  95

Ala Arg His Glu Asp Gly Asn Trp Asn Tyr Phe Asp Tyr Trp Gly Gln
                100                 105                 110

Gly Thr Thr Leu Thr Val Ser Ser Ala Ser Ser Glu Glu Glu Ile Arg
                115                 120                 125

Glu Ala Phe Arg Val Phe Asp Lys Asp Gly Asn Gly Tyr Ile Ser Ala
            130                 135                 140

Ala Glu Leu Arg His Val Met Thr Asn Leu Gly Glu Lys Leu Thr Asp
145                 150                 155                 160

Glu Glu Val Asp Glu Met Ile Arg Glu Ala Asp Ile Asp Gly Asp Gly
                165                 170                 175

Gln Val Asn Tyr Glu Glu Phe Val Gln Met Met Thr Ala Lys Gly Gly
                180                 185                 190

Ser Gly Ala Asp Gln Leu Thr Glu Glu Gln Ile Ala Glu Phe Lys Glu
                195                 200                 205

Ala Phe Ser Leu Phe Asp Lys Asp Gly Asp Gly Thr Ile Thr Thr Lys
            210                 215                 220

Glu Leu Gly Thr Val Met Arg Ser Leu Gly Gln Asn Pro Thr Glu Ala
225                 230                 235                 240

Glu Leu Gln Asp Met Ile Asn Glu Val Asp Ala Asp Gly Asn Gly Thr
```

```
                    245                 250                 255
Ile Asp Phe Pro Glu Phe Leu Thr Met Met Ala Arg Lys Met Lys Asp
                260                 265                 270

Thr Asp Asp Ile Glu Thr Thr Val Thr Gln Ser Pro Ala Ser Leu Ser
            275                 280                 285

Val Ala Ile Gly Glu Lys Val Thr Ile Arg Cys Ile Thr Ser Thr Asp
        290                 295                 300

Ile Asp Asp Asp Met Asn Trp Tyr Gln Gln Lys Pro Gly Glu Pro Pro
305                 310                 315                 320

Lys Phe Phe Ile Ser Glu Gly Asn Thr Leu Arg Pro Gly Val Pro Ser
                325                 330                 335

Arg Phe Ser Ser Gly Tyr Gly Thr Asp Phe Val Phe Thr Ile Glu
            340                 345                 350

Asn Met Leu Ser Glu Asp Val Ala Asp Tyr Tyr Cys Leu Gln Ser Asp
                355                 360                 365

Thr Leu Pro Leu Thr Phe Gly Ser Gly Thr Lys Leu Glu Ile Lys Ala
            370                 375                 380

Ala Ala His His His His His Ser Ser Gly Gly Arg Gly Ser
385                 390                 395                 400

His His His His His His
            405

<210> SEQ ID NO 133
<211> LENGTH: 406
<212> TYPE: PRT
<213> ORGANISM: artificial sequence
<220> FEATURE:
<223> OTHER INFORMATION: anti-CD4 scFv (Q425)_C-1

<400> SEQUENCE: 133

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Gly Leu Glu Trp Val
        35                  40                  45

Ala Thr Ile Ser Ser Gly Gly Ser Tyr Thr Tyr Tyr Pro Asp Asn Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Glu Asp Gly Asn Trp Asn Tyr Phe Asp Tyr Trp Gly Gln
            100                 105                 110

Gly Thr Thr Leu Thr Val Ser Ser Ala Ser Lys Gly Gly Ser Gly Ala
        115                 120                 125

Asp Gln Leu Thr Glu Glu Gln Ile Ala Glu Phe Lys Glu Ala Phe Ser
    130                 135                 140

Leu Phe Asp Lys Asp Gly Asp Gly Thr Ile Thr Thr Lys Glu Leu Gly
145                 150                 155                 160

Thr Val Met Arg Ser Leu Gly Gln Asn Pro Thr Glu Ala Glu Leu Gln
                165                 170                 175

Asp Met Ile Asn Glu Val Asp Ala Asp Gly Asn Gly Thr Ile Asp Phe
            180                 185                 190

Pro Glu Phe Leu Thr Met Met Ala Arg Lys Met Lys Asp Thr Asp Ser
```

```
                    195                 200                 205
Glu Glu Glu Ile Arg Glu Ala Phe Arg Val Phe Asp Lys Asp Gly Asn
            210                 215                 220

Gly Tyr Ile Ser Ala Ala Glu Leu Arg His Val Met Thr Asn Leu Gly
225                 230                 235                 240

Glu Lys Leu Thr Asp Glu Val Asp Glu Met Ile Arg Glu Ala Asp
                245                 250                 255

Ile Asp Gly Asp Gly Gln Val Asn Tyr Glu Glu Phe Val Gln Met Met
            260                 265                 270

Thr Ala Asp Ile Glu Thr Thr Val Thr Gln Ser Pro Ala Ser Leu Ser
        275                 280                 285

Val Ala Ile Gly Glu Lys Val Thr Ile Arg Cys Ile Thr Ser Thr Asp
290                 295                 300

Ile Asp Asp Asp Met Asn Trp Tyr Gln Gln Lys Pro Gly Glu Pro Pro
305                 310                 315                 320

Lys Phe Phe Ile Ser Glu Gly Asn Thr Leu Arg Pro Gly Val Pro Ser
                325                 330                 335

Arg Phe Ser Ser Ser Gly Tyr Gly Thr Asp Phe Val Phe Thr Ile Glu
            340                 345                 350

Asn Met Leu Ser Glu Asp Val Ala Asp Tyr Tyr Cys Leu Gln Ser Asp
                355                 360                 365

Thr Leu Pro Leu Thr Phe Gly Ser Gly Thr Lys Leu Glu Ile Lys Ala
        370                 375                 380

Ala Ala His His His His His His Ser Ser Gly Gly Arg Gly Ser
385                 390                 395                 400

His His His His His His
                405

<210> SEQ ID NO 134
<211> LENGTH: 406
<212> TYPE: PRT
<213> ORGANISM: artificial sequence
<220> FEATURE:
<223> OTHER INFORMATION: anti-CD4 scFv (Q425)_C-2

<400> SEQUENCE: 134

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Asp Lys Gly Leu Glu Trp Val
            35                  40                  45

Ala Thr Ile Ser Ser Gly Gly Ser Tyr Thr Tyr Tyr Pro Asp Asn Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Glu Asp Gly Asn Trp Asn Tyr Phe Asp Tyr Trp Gly Gln
            100                 105                 110

Gly Thr Thr Leu Thr Val Ser Ser Ala Ser Ala Lys Gly Gly Ser Gly
        115                 120                 125

Ala Asp Gln Leu Thr Glu Glu Gln Ile Ala Glu Phe Lys Glu Ala Phe
    130                 135                 140

Ser Leu Phe Asp Lys Asp Gly Asp Gly Thr Ile Thr Thr Lys Glu Leu
```

```
                    145                 150                 155                 160
Gly Thr Val Met Arg Ser Leu Gly Gln Asn Pro Thr Glu Ala Glu Leu
                165                 170                 175
Gln Asp Met Ile Asn Glu Val Asp Ala Asp Gly Asn Gly Thr Ile Asp
            180                 185                 190
Phe Pro Glu Phe Leu Thr Met Met Ala Arg Lys Met Lys Asp Thr Asp
        195                 200                 205
Ser Glu Glu Glu Ile Arg Glu Ala Phe Arg Val Phe Asp Lys Asp Gly
    210                 215                 220
Asn Gly Tyr Ile Ser Ala Ala Glu Leu Arg His Val Met Thr Asn Leu
225                 230                 235                 240
Gly Glu Lys Leu Thr Asp Glu Glu Val Asp Glu Met Ile Arg Glu Ala
                245                 250                 255
Asp Ile Asp Gly Asp Gly Gln Val Asn Tyr Glu Glu Phe Val Gln Met
            260                 265                 270
Met Thr Asp Ile Glu Thr Thr Val Thr Gln Ser Pro Ala Ser Leu Ser
        275                 280                 285
Val Ala Ile Gly Glu Lys Val Thr Ile Arg Cys Ile Thr Ser Thr Asp
    290                 295                 300
Ile Asp Asp Asp Met Asn Trp Tyr Gln Gln Lys Pro Gly Glu Pro Pro
305                 310                 315                 320
Lys Phe Phe Ile Ser Glu Gly Asn Thr Leu Arg Pro Gly Val Pro Ser
                325                 330                 335
Arg Phe Ser Ser Ser Gly Tyr Gly Thr Asp Phe Val Phe Thr Ile Glu
            340                 345                 350
Asn Met Leu Ser Glu Asp Val Ala Asp Tyr Tyr Cys Leu Gln Ser Asp
        355                 360                 365
Thr Leu Pro Leu Thr Phe Gly Ser Gly Thr Lys Leu Glu Ile Lys Ala
    370                 375                 380
Ala Ala His His His His His His Ser Ser Gly Gly Gly Arg Gly Ser
385                 390                 395                 400
His His His His His His
                405

<210> SEQ ID NO 135
<211> LENGTH: 263
<212> TYPE: PRT
<213> ORGANISM: artificial sequence
<220> FEATURE:
<223> OTHER INFORMATION: clone D1.3 (WT); scFv derived from murine
      antibody against hen egg white lysozyme

<400> SEQUENCE: 135

Glu Val Lys Leu Gln Glu Ser Gly Pro Gly Leu Val Ala Pro Ser Gln
1               5                   10                  15
Ser Leu Ser Ile Thr Cys Thr Val Ser Gly Phe Ser Leu Thr Gly Tyr
            20                  25                  30
Gly Val Asn Trp Val Arg Gln Pro Pro Gly Lys Gly Leu Glu Trp Leu
        35                  40                  45
Gly Met Ile Trp Gly Asp Gly Asn Thr Asp Tyr Asn Ser Ala Leu Lys
    50                  55                  60
Ser Arg Leu Ser Ile Ser Lys Asp Asn Ser Lys Ser Gln Val Phe Leu
65                  70                  75                  80
Lys Met Asn Ser Leu His Thr Asp Asp Thr Ala Arg Tyr Tyr Cys Ala
                85                  90                  95
```

```
Arg Glu Arg Asp Tyr Arg Leu Asp Tyr Trp Gly Gln Gly Thr Thr Val
            100                 105                 110

Thr Val Ser Ser Ala Ser Gly Gly Gly Ser Gly Gly Gly Gly Ser
        115                 120                 125

Gly Gly Gly Gly Ala Asp Ile Glu Leu Thr Gln Ser Pro Ala Ser Leu
    130                 135                 140

Ser Ala Ser Val Gly Glu Thr Val Thr Ile Thr Cys Arg Ala Ser Gly
145                 150                 155                 160

Asn Ile His Asn Tyr Leu Ala Trp Tyr Gln Gln Lys Gln Gly Lys Ser
                165                 170                 175

Pro Gln Leu Leu Val Tyr Tyr Thr Thr Thr Leu Ala Asp Gly Val Pro
            180                 185                 190

Ser Arg Phe Ser Gly Ser Gly Ser Gly Thr Gln Tyr Ser Leu Lys Ile
        195                 200                 205

Asn Ser Leu Gln Pro Glu Asp Phe Gly Ser Tyr Tyr Cys Gln His Phe
    210                 215                 220

Trp Ser Thr Pro Arg Thr Phe Gly Gly Gly Thr Lys Leu Glu Leu Lys
225                 230                 235                 240

Ala Ala Ala His His His His His His Ser Ser Gly Gly Gly Arg Gly
                245                 250                 255

Ser His His His His His His
            260

<210> SEQ ID NO 136
<211> LENGTH: 5
<212> TYPE: PRT
<213> ORGANISM: Artificial Sequence
<220> FEATURE:
<223> OTHER INFORMATION: Synthetic Construct

<400> SEQUENCE: 136

Gly Gly Gly Gly Ser
1               5

<210> SEQ ID NO 137
<211> LENGTH: 15
<212> TYPE: PRT
<213> ORGANISM: Artificial Sequence
<220> FEATURE:
<223> OTHER INFORMATION: Synthetic Construct

<400> SEQUENCE: 137

Gly Gly Gly Gly Ser Gly Gly Gly Gly Ser Gly Gly Gly Gly Ser
1               5                   10                  15
```